US010611800B2

(12) United States Patent
Yang et al.

(10) Patent No.: US 10,611,800 B2
(45) Date of Patent: Apr. 7, 2020

(54) HUMAN CYTOMEGALOVIRUS GB POLYPEPTIDE

(71) Applicant: Pfizer Inc., New York, NY (US)

(72) Inventors: Xinzhen Yang, Woodcliff Lake, NJ (US); Xiaoyuan Sherry Chi, Tenafly, NJ (US)

(73) Assignee: Pfizer Inc., New York, NY (US)

( * ) Notice: Subject to any disclaimer, the term of this patent is extended or adjusted under 35 U.S.C. 154(b) by 11 days.

(21) Appl. No.: 16/082,177

(22) PCT Filed: Mar. 9, 2017

(86) PCT No.: PCT/IB2017/051401
§ 371 (c)(1),
(2) Date: Sep. 4, 2018

(87) PCT Pub. No.: WO2017/153954
PCT Pub. Date: Sep. 14, 2017

(65) Prior Publication Data
US 2019/0127422 A1     May 2, 2019

Related U.S. Application Data

(60) Provisional application No. 62/463,982, filed on Feb. 27, 2017, provisional application No. 62/307,423, filed on Mar. 11, 2016.

(51) Int. Cl.
*C07K 14/005* (2006.01)
*A61K 39/245* (2006.01)
*A61P 31/20* (2006.01)

(52) U.S. Cl.
CPC .......... *C07K 14/005* (2013.01); *A61K 39/245* (2013.01); *A61P 31/20* (2018.01); *C12N 2710/16122* (2013.01); *C12N 2710/16134* (2013.01); *C12N 2710/16171* (2013.01)

(58) Field of Classification Search
None
See application file for complete search history.

(56) References Cited

U.S. PATENT DOCUMENTS

| | | | |
|---|---|---|---|
| 5,244,805 A | 9/1993 | Miller | |
| 8,716,257 B2 | 5/2014 | Cobbs et al. | |
| 2002/0076813 A1 | 6/2002 | Steaffens et al. | |
| 2011/0200633 A1 | 8/2011 | Shenk et al. | |
| 2015/0359879 A1 | 12/2015 | Wellnitz et al. | |

FOREIGN PATENT DOCUMENTS

| | | |
|---|---|---|
| EP | 3031822 A1 | 6/2016 |
| WO | 1989/007143 A1 | 8/1989 |
| WO | 1991/015586 A1 | 10/1991 |
| WO | 1994/000150 A1 | 1/1994 |
| WO | 1994/003620 A2 | 2/1994 |
| WO | 1994/017810 A1 | 8/1994 |
| WO | 1995/028941 A1 | 11/1995 |
| WO | 1995/031555 A1 | 11/1995 |
| WO | 1995/032213 A1 | 11/1995 |
| WO | 1996/004383 A1 | 2/1996 |
| WO | 1996/004384 A1 | 2/1996 |
| WO | 1996/039491 A1 | 12/1996 |
| WO | 1997/005262 A1 | 2/1997 |
| WO | 1997/031117 A2 | 8/1997 |
| WO | 1997/033992 A1 | 9/1997 |
| WO | 1997/040165 A1 | 10/1997 |
| WO | 1998/002746 A1 | 1/1998 |
| WO | 1998/021233 A2 | 5/1998 |
| WO | 1998/026074 A1 | 6/1998 |
| WO | 1998/045314 A1 | 10/1998 |
| WO | 1999/013075 A2 | 3/1999 |
| WO | 1999/019349 A1 | 4/1999 |
| WO | 2000/053729 A2 | 9/2000 |
| WO | 2000/075180 A2 | 12/2000 |
| WO | 2001/016153 A1 | 3/2001 |
| WO | 2011/119920 A2 | 9/2001 |
| WO | 2001/072782 A2 | 10/2001 |
| WO | 2002/018954 A2 | 3/2002 |
| WO | 2002/034769 A2 | 5/2002 |
| WO | 2002/062296 A2 | 8/2002 |
| WO | 2002/062956 A2 | 8/2002 |
| WO | 2002/066629 A2 | 8/2002 |
| WO | 2003/000720 A1 | 1/2003 |
| WO | 2003/035835 A2 | 5/2003 |
| WO | 2004/000873 A2 | 12/2003 |
| WO | 2004/055166 A2 | 7/2004 |
| WO | 2004/058166 A2 | 7/2004 |
| WO | 2004/076645 A2 | 9/2004 |
| WO | 2004/093905 A1 | 11/2004 |
| WO | 2004/111080 A1 | 12/2004 |

(Continued)

OTHER PUBLICATIONS deVries, et al., "Cytomegalovirus DNA Detection in Dried Blood Spots and Perilymphatic Fluids From Pediatric and Adult Cochlear Implant Recipients With Prelingual Deafness", Journal of Clinical Virology, 56(2):113-117 (2013).
Digel, et al., Determinants of Endothelial Cell Tropism of Human Cytomegalovirus, Molecular Biolgy and Immunolgy, 445-464 (2006).
Dolan, et al., "Genetic Content of Wild-Type Human Cytomegalovirus", Journal of General Virology, 85:1301-1312 (2004).
Douvas, A., et al., "Multiple Overlapping Homologies Between Two Rheumatoid Antigens and Immunosuppressive Viruses", Proc. Natl. Acad. Sci., 88(14):6328-6332 (1991).
Eggers, M., et al., "Use of Recombinant Glycoprotein Antigens gB and gH for Diagnosis of Primary Human Cytomegalovirus Infection During Pregnancy", Journal of Medical Virology, 63(2):135-142 (2001).
Eisenberg, R., et al., "Herpes Virus Fusion and Entry: A Story with Many Characters", Viruses 4(5):800-832 (2012).

(Continued)

*Primary Examiner* — Stacy B Chen
(74) *Attorney, Agent, or Firm* — Anna C. Chau

(57) ABSTRACT

The present invention relates to a polypeptide that includes at least one mutation in the fusion loop 1 region and/or in the fusion loop 2 region and/or in the furin-like cleavage site of a human cytomegalovirus gB polypeptide. In one embodiment, the polypeptide undergoes a structural conformation change in response to pH change.

8 Claims, 19 Drawing Sheets

Specification includes a Sequence Listing.

(56) References Cited

FOREIGN PATENT DOCUMENTS

| | | |
|---|---|---|
| WO | 2005/007689 A1 | 1/2005 |
| WO | 2005/012545 A2 | 2/2005 |
| WO | 2005/035771 A2 | 4/2005 |
| WO | 2005/085456 A1 | 9/2005 |
| WO | 2006/004661 A1 | 1/2006 |
| WO | 2006/056027 A1 | 6/2006 |
| WO | 2006/110728 A2 | 10/2006 |
| WO | 2007/054250 A1 | 5/2007 |
| WO | 2007/068758 A1 | 6/2007 |
| WO | 2007/068907 A2 | 6/2007 |
| WO | 2007062832 A2 | 6/2007 |
| WO | 2007/106404 A1 | 9/2007 |
| WO | 2007/130470 A2 | 11/2007 |
| WO | 2007/146024 A2 | 12/2007 |
| WO | 2008/003327 A1 | 1/2008 |
| WO | 2008/071806 A1 | 6/2008 |
| WO | 2008/084410 A2 | 7/2008 |
| WO | 2008/095677 A1 | 8/2008 |
| WO | 2008/120203 A2 | 10/2008 |
| WO | 2008/138590 A1 | 11/2008 |
| WO | 2009/037359 A1 | 3/2009 |
| WO | 2009/049138 A1 | 4/2009 |
| WO | 2009/114560 A2 | 9/2009 |
| WO | 2009/155535 A2 | 12/2009 |
| WO | 2010/007463 A2 | 1/2010 |
| WO | 2010/007533 A2 | 1/2010 |
| WO | 2010/014567 A2 | 2/2010 |
| WO | 2010/114106 A1 | 10/2010 |
| WO | 2010/125201 A1 | 11/2010 |
| WO | 2010/128338 A2 | 11/2010 |
| WO | 2010/148541 A1 | 12/2010 |
| WO | 2011/053798 A2 | 5/2011 |
| WO | 2011/076883 A1 | 6/2011 |
| WO | 2011/093858 A1 | 8/2011 |
| WO | 2011/124371 A1 | 10/2011 |
| WO | 2011/143653 A2 | 11/2011 |
| WO | 2011/159938 A2 | 12/2011 |
| WO | 2012/034025 A2 | 3/2012 |
| WO | 2012/049317 A2 | 4/2012 |
| WO | 2012051211 A2 | 4/2012 |
| WO | 2012/097105 A1 | 7/2012 |
| WO | 2012/135177 A2 | 10/2012 |
| WO | 2012/141653 A2 | 10/2012 |
| WO | 2012/152644 A1 | 11/2012 |
| WO | 2012/170765 A2 | 12/2012 |
| WO | 2013/006838 A1 | 1/2013 |
| WO | 2013/006842 A2 | 1/2013 |
| WO | 2013/036465 A2 | 3/2013 |
| WO | 2013/054199 A2 | 4/2013 |
| WO | 2013/068847 A2 | 5/2013 |
| WO | 2013144722 A2 | 10/2013 |
| WO | 2013/165982 A2 | 11/2013 |
| WO | 2014/018117 A1 | 1/2014 |
| WO | 2014005959 A1 | 1/2014 |
| WO | 2014/060594 A1 | 4/2014 |
| WO | 2014/068001 A1 | 5/2014 |
| WO | 2014/138086 A1 | 9/2014 |
| WO | 2014/138209 A1 | 9/2014 |
| WO | 2014145932 A2 | 9/2014 |
| WO | 2014/200898 A2 | 12/2014 |
| WO | 2015181142 A1 | 12/2015 |
| WO | 2016092460 A1 | 6/2016 |

OTHER PUBLICATIONS

Elkington, R., et al., "Cross-Reactive Recognition of Human and Primate Cytomegalovirus Sequences by Human CD4 Cytotoxic T Lymphocytes Specific for Glycoprotein B and H", Eur. J. Immunol, 34(11):3216-3226 (2004).

Engel, P., et al., "Viral Immunomodulatory Proteins: Usurping Host Genes as a Survival Strategy", Self and Nonself Advances in Experimental Medicine and Biology, 738:256-276 (2012).

English, et al., "Foldamer-Based Inhibitors of Cytomegalovirus Entry", Antiviral Research, 70(1):A32 (2006).

English, et al., "Rational Development of Beta-Peptide Inhibitors of Human Cytomegalovirus Entry", 281(5):2661-2667 (2006).

Fornara, O., et al., "Human Cytomegalovirus Particles Directly Suppress CD4 T-Lymphocyte Activation and Proliferation", Immunobiology, 218(8):1034-1040 (2013).

Fouts, A. et al., "Antibodies Against the gH/ gL/ UL128/UL130/ UL131 Complex Comprise the Majority of the Anti-Cytomegalovirus (anti-CMV) Neutralizing Antibody Response in CMV Hyperimmune Globulin", Journal of Virology, 86(13):7444-7447 (2012).

Fouts, A., et al., "Mechanism for neutralizing activity by the anti-CMV gH/ gLmonoclonal antibody MSL-109", PNAS, 111(22):8209-8214 (2014).

Freed, D.C., et al., "Pentameric complex of viral glycoprotein H is the primary target for potent neutralization by a human cytomegalovirus vaccine", Proceedings of the National Academy of Scienes, 110(51):E4997-E5005 (2013).

Fu, T.M., et al., "Progress on pursuit of human cytomegalovirus vaccines for prevention of congenital infection and disease", Vaccine, 32(22):2525-2533 (2014).

Fu, T.M., et al., "Restoration of Viral Epithelial Tropism improves immunogenicity in rabbits and rhesus macaques for a whole virion vaccine of human Cytomegalovirus", Vaccine, 30(52):7469-7474 (2012).

Fukushima, E., et al., "Identification of a Highly Conserved Region in the Human Cytomegalovirus Glycoprotein H Gene and Design of Molecular Diagnostic Methods Targeting the Region", Journal of Virological Methods, 151(1):55-60 (2008).

Ge, X., et al., "CD134-Allodepletion Allows Selective Elimination of Alloreactive Human T Cells Without Loss of Virus-Specific and Leukemia-Specific Effectors", Biology of Blood & Marrow Transplatation 14(5):518-530 (2008).

Genini, E., et al., Serum Antibody Response to the gH/ gL/ pUL128-131 Five-Protein Complex of Human Cytomegalovirus (HCMV) in Primary and Reactivated HCMV Infections, Journal of Clinical Virology, 52(2):113-118 (2011).

Gerna, G., et al., Dendritic-Cell Infection by Human Cytomegalovirus is Restricted to Strains Carrying Functional UL131-128 Genes and Mediates Efficient Viral Antigen Presentation to CD8+ T Cells, Journal of General Virology, 86:275-284 (2005).

Gerna, G., et al., Human Cytomegalovirus Serum Neutralizing Antibodies Block Virus Infection of Endothelial/Epithelial Cells, but Not Fibroblasts, Early During Primary Infection, Journal of General Virology, 89:853-865 (2008).

Gerna, G., et al., "Differential Kinetics of Human Cytomegalovirus Load and Antibody Responses in Primary Infection of the Immunocompetent and Immunocompromised Host", Journal of General Virology, 96:360-369 (2015).

Gill, T., et al.,"Replication-Defective Mutants of Mouse Cytomegalovirus Protect Against Wild-Type Virus Challenge", Journal of Medical Virology, 62(2):127-139 (2000).

Gnanandarajah, J., et al., Identification by Mass Spectrometry and Immune Response Analysis of Guinea Pig Cytomegalovirus (GPCMV) Pentameric Complex Proteins GP129, 131 and 133, Viruses, 6(2):727-751 (2014).

Gonczol, E., et al., "Development of a Cytomegalovirus Vaccine: Lessons From Recent Clinical Trials", Expert Opinion on Biological Therapy, 1(3):401-412 (2001).

Gorzer, I., et al., "Virus Load Dynamics of Individual CMV-Genotypes in Lung Transplant Recipients with Mixed-Genotype Infections", Journal of Medical Virology, 80(8):1405-1414 (2008).

Gorzer, I., et al., "Analysis of Human Cytomegalovirus Strain Populations in Urine Samples of Newborns by Ultra Deep Sequencing", Journal of Clinical Virology, 73:101-104 (2015).

Gredmark, S., et al., "Human Cytomegalovirus Induces Inhibition of Macrophage Differentiation by Binding to Human Aminopeptidase N/CD13", Journal of Immunology, 173(8):4897-48907 (2004).

Griesenbach, U., et al., "Gene Therapy Progress and Prospects: Cystic Fibrosis", Gene Therapy, 13(14):1061-1067 (2006).

Grosjean, J., et al., "Human Cytomegalovirus Quantification in Toddlers Saliva from Day Care Centers and Emergency Unit: A Feasibility Study", 61(3):371-377 (2014).

(56) References Cited

OTHER PUBLICATIONS

Hahn, G., et al., "Human Cytomegalovirus UL131-128 Genes are Indispensable for Virus Growth in Endothelial Cells and Virus Transfer to Leukocytes", Journal of Virology, 78(18):10023-10033 (2004).
Halwachs-Baumann, G., et al., "Virus-Host Interaction for Defence and Transmission", BIOSIS Previews Congenital Cytomegalovirus Infection: Epidemiology, Diagnosis, Therapy, 11-51 (2011).
Hansen, S., et al., "Cytomegalovirus Vectors Violate CD8+ T Cell Epitope Recognition Paradigms", Science, 340:1237874-1-1237874-17 (2013).
Hobom, U., et al., "Fast Screening Procedures for Random Transposon Libraries of Cloned Herpesvirus Genomes: Mutational Analysis of Human Cytomegalovirus Envelope Glycoprotein Genes", Journal of Virology, 74(17):7720-7729 (2000).
Hofmann, I., et al., "Expression of the Human Cytomegalovirus Pentamer Complex for Vaccine Use in a CHO System", Biotechnology & Bioengineering, 112(12):2505-2515 (2015).
Hui-Hui, G., et al., "Recombinant HCMV UL128 Expression and Functional Identification of PBMC-Attracting Activity In Vitro", Archives of Virology, 158(1):173-177 (2013).
Ibig-Rehm, Y., et al., "High-Content Screening to Distinguish Between Attachment and Post-Attachment Steps of Human Cytomegalovirus Entry into Fibroblasts and Epithelial Cells", Anivural Research, 89(3):246-256 (2011).
Ikuta, K., et al., "Cytomegalovirus (CMV) Glycoprotein H-Based Serological Analysis in Japanese Healthy Pregnant Women, and in Neonates With Congenital CMV Infection and Their Mothers", Journal of Clinical Virology, 58(2):474-478 (2013).
Ishibashi, K., et al., "Strain-Specific Seroepidemiology and Reinfection of Cytomegalovirus", Microbes & Infection 10(12-13):1363-1369 (2008).
Ishibashi, K., et al., "Lack of Antibodies Against the Antigen Domain 2 Epitope of Cytomegalovirus (CMV) Glycoprotein B is Associated With CMV Disease After Renal Transplantation in Recipients Having the Same Glycoprotein H Serotypes as Their Donors", Transplant Infectious Disease, 13(3):318-323 (2011).
Jacob, C., et al., "Neutralizing Antibodies are Unable to Inhibit Direct Viral Cell-to-Cell Spread of Human Cytomegalovirus", Virology 444(1-2):140-147 (2013).
Jarvis, M., et al., "Human Cytomegalovirus Infection of Caco-2 Cells Occurs at the Basolateral Membrane and is Differentiation State Dependent", Journal of Virology 73(6):4552-4560 (1999).
Jaskula, E., et a., "Severe CMV Load Post HSCT is Inversely Correlated With a Proportion of CD8high+Pro5 Pentamer HLA-A*0201/NLVPMVATV (CMV pp65)+ Cells and Associates With a Risk of Fatal Complications", Biosis Previews Bone Marrow Transplantation, 39(1):S163 (2007).
Jiang, X., et al., "UL74 of Human Cytomegalovirus Reduces the Inhibitory Effect of gH-Specific and gB-Specific Antibodies", Archives of Virology, 156(2):2145-255 (2011).
Kabanova, A., et al., "Antibody-Driven Design of a Human Cytomegalovirus gHgLpUL128L Subunit Vaccine That Selectively Elicits Potent Neutralizing Antibodies", PNAS, 111(50):17965-17970 (2014).
Karlsson, H., et al., Generation of Trispecific Cytotoxic T Cells Recognizing Cytomegalovirus, Adenovirus, and Epstein-Barr Virus: An Approach for Adoptive Immunotherapy of Multiple Pathogens, Journal of Immunotherapy, 30(5):544-556 (2007).
Kinzler, et al., "Characterization of Human Cytomegalovirus Glycoprotein-Induced Cell-Cell Fusion", Journal of Virology, 79(12):7827-7837 (2005).
Klein, M., et al., "Strain-Specific Neutralization of Human Cytomegalovirus Isolates by Human Sera", Journal Virology, 73(2):878-886 (1999).
Klinger, M., et al., "Combining Next-Generation Sequencing and Immune Assays: A Novel Method for Identification of Antigen-Specific T Cells", PLOS ONE, 8(9):e74231 1-9 (2013).
Klupp, B., et al., "Pseudorabies Virus Glycoprotein M Inhibits Membrane Fusion", Journal of Virology, 74(15):6760-6768 (2000).

Achour, A., et al., "Variability of gB and gH Genes of Human Herpesvirus-6 Among Clinical Specimens", Journal of Medical Virology, 80:1211-1221 (2008).
Adler, B., et al., "Role of Human Cytomegalovirus UL131A in Cell Type-Specific Virus Entry and Release", Journal of General Virology, 87:2451-2460 (2006).
Adler, B., et al., Endothelial Cells in Human Cytomegalovirus Infection: One Host Cell Out of Many or a Crucial Target for Virus Spread?, Thrombosis & Haemostasis, 102(6): 1057-1063 (2009).
Adler, S., "Immunization to Prevent Congenital Cytomegalovirus Infection", British Medical Bulletin, 107:57-68 (2013).
Akter, et al., "Two Novel Spliced Genes in Human Cytomegalovirus", Journal of General Virology 84: 1117-1122 (2003).
Al-Ahadal, et al., "Typing of Human Cytomegalovirus Clinical Isolates from Saudi Patients by PCR-RFLP", Infection, 33(2):73-76 (2005).
Albon, et al., "Optimization of Methodology for Production of CD25/CD71 Allodepleted Donor T Cells for Clinical Use", Cytotherapy 15: 109-121 (2013).
Almehmadi, M., et al., "Increased Number and Functional Activity of CD56+ T Cells in Healthy Cytomegalovirus Positive Subjects", Immunology, 142(2):258-268 (2014).
Angelini, D., et al., "Increased CD8+ T Cell Response to Epstein-Barr Virus Lytic Antigens in the Active Phase of Multiple Sclerosis", PLOS Pathogens, 9(4):1-16, (2013).
Aquino, V., et al., "Cytomegalovirus Infection in Renal Transplant Recipients Diagnosed by Nested-PCR", Brazilian Journal of Medical and Biological Research, 34(1):93-101 (2001).
Arav-Boger, "Strain Variation and Disease Severity in Congenital Cytomegalovirus Infection: In Search of a Viral Marker", Infectious Disease Clinics of North America, 29(3):401-414 (2015).
Assaf, B., et al., "Limited Dissemination and Shedding of the UL128 Complex-Intact, UL/b'-Defective Rhesus Cytomegalovirus Strain 180.92", Journal of Virology, 88(16):9310-9320 (2014).
Auerbach, et al., "Characterization of the Guinea Pig CMV gH/gL/GP129/GP131/GP133 Complex in Infection and Spread", Virology, 441(1):75-84 (2013).
Baldanti, S., et al., "Human Cytomegalovirus UL131A, UL130 and UL128 Genes are Highly Conserved Among Field Isolates", Archives of Virology, 151(6): 1225-1233 (2006).
Baldwin, J., et al., "A Role of 3-O-Sulfated Heparan Sulfate in Promoting Human Cytomegalovirus Infection in Human Iris Cells", Journal of Virology, 89(9):5185-5192 (2015).
Barry, P., "Exploiting Viral Natural History for Vaccine Development", Medical Microbiology Immunology, 204(3):255-262 (2015).
Beloki, L., et al. "The Abrogation of TCR-Independent Interactions With Human Serum Ensures a Selective Capture of Therapeutic Virus-Specific CD8+ T-Cells by Multimer Technology in Adoptive Immunotherapy", Journal of Immunological Methods, 396(1-2):168-172 (2013).
Beloki, L., et al. "Manufacturing of CMV-Specific T Cells From G-CSF Mobilised Donors for Adoptive Immunotherapy That Preserve Strong Anti-Viral and Cytotoxic Activity", 16(4):S20 (2014).
Beloki, L., et al. "CMV-Specific T Cell Isolation From G-CSF Mobilized Peripheral Blood: Depletion of Myeloid Progenitors Eliminates Non-Specific Binding of MHC-Multimers, Journal of Translational Medicine", 12:317 (2014).
Beninga, Comparative Analysis of Fourteen Individual Human Cytomegalovirus Proteins for Helper T Cell Response, Journal of General Virology 76:153-160 (1995).
Berger, I., et al., "Baculovirus Expression System for Heterologous Multiprotein Complexes", Nat Biotechnol, 22(12):1583-7 (2004).
Bevan, L., et al., "Investigation of Murine Cytomegalovirus Latency and Reactivation in Mice Using Viral Mutants and the Polymerase Chain Reaction", Journal of Medical Virology, 48(4):308-320 (1996).
Binder, T., et al., "Identification of Human Cytomegalovirus Variants by Analysis of Single Strand Conformation Polymorphism and DNA Sequencing of the Envelope Glycoprotein B Gene Region-Distribution Frequency in Liver Transplant Recipients", Journal of Virological Methods 78:153-162 (1999).
Biotechnet: "The Vaccine-Factory in the Box—from vision to reality", Swissinnovate, Retrieved from the Internet, http://webcache.

(56) References Cited

OTHER PUBLICATIONS goofleusercontent.com/search?q=cache:PtrCZH9byBkJ:www.biotechnet.com, 1, 19, 20 (2013).
Boccuni, M., et al., "Human Cytomegalovirus Product UL44 Downregulates the Transactivation of HIV-1 Long Terminal Repeat", AIDS 12(4):365-372 (1998).
Boechk, M., et al., "Randomized, Placebo-Controlled, Double-Blind Study of a Cytomegalovirus-Specific Monoclonal Antibody (MSL-109) for Prevention of Cytomegalovirus Infection After Allogeneic Hematopoietic Stem Cell Transplantation", Biology of Blood & Marrow Transplantation, 7(6):343-351 (2001).
Boehme, KW., et al., Human Cytomegalovirus Envelope Glycoproteins B and H are Necessary for TLR2 Activation in Permissive Cells, Journal of Immunology, 177:(10)7094-7102 (2006).
Boppana, S. et al., "Transplacentally Acquired Antiviral Antibodies and Outcome in Congenital Human Cytomegalovirus Infection", Viral Immunology, 9(4):211-218 (1996).
Boppana, S. et al., "Recognition of Human Cytomegalovirus Gene Products by HCMV-Specific Cytotoxic T Cells", Virology, 222(1):293-296 (1996).
Borchers, S., "Multimer monitoring of CMV-Specific T Cells in Research and in Clinical Applications", Diagnostic Microbiolgoy & Infectious Disease, 78(3):201-212 (2014).
Bowman, J., et al., "Rhesus and Human Cytomegalovirus Glycoprotein L are Required for Infection and Cell-to-Cell Spread of Virus but Cannot Complement Each Other", Journal of Virology, 85(5):2089-2099 (2011).
Brady, R., et al., "Identification and Characterization of the Guinea-Pig Cytomegalovirus Glycoprotein H Gene", Archives of Virology, 141(12):2409-2424 (1996).
Britt, W., et al., "Human Cytomegalovirus Glycoproteins", Intervirology, 39(5-6):401-412 (1996).
Britt, W., et al., "Human Cytomegalovirus Virion Proteins", Human Immunology, 65(5):395-402 (2004).
Bueno, J., et al., "Current Management Strategies for the Prevention and Treatment of Cytomegalovirus Infection in Pediatric Transplant Recipients", Pediatic Drugs, 4(5): 279-290 (2002).
Buscher, N., et al., "The Proteome of Human Cytomegalovirus Virions and Dense Bodies is Conserved Across Differenct Strains", Medical Microbiology & Immunology, 204(3):285-293 (2015).
Butcher, S., et al., "Structure of the Human Cytomegalovirus B Capsid by Electron Cryomicroscopy and Image Reconstruction", Journal of Structural Biology, 124:70-76 (1998).
Cerutti, M., et al., "Lepidopteran cells, an alternative for the production of recombinant antibodies?", MAbs. May-Jun. 2012;4(3):294-309. Epub Apr. 26, 2012.
Chan, Y., et al., "Two Distinct Upstream Regulatory Domains Containing Multicopy Cellular Transcription Factor Binding Sites Provide Basal Repression and Inducible Enhancer Characteristics to the Immediate-Early IES (US3) Promoter From Human Cytomegalovirus", Journal of Virology, 70(8):5312-5328 (1996).
Chiuppesi, F., et al., "Vaccine-Derived Neutralizing Antibodies to the Human Cytomegalovirus gH/ gLPentamer Potently Block Primary Cytotrophoblast Infection", Journal of Virology, 89(23):11884-1198 (2015).
Chou, S., "Molecular Epidemiology of Envelope Glycoprotein H of Human Cytomegalovirus", Journal of Infectious Diseases, 166(3):604-607 (1992).
Ciferri, et al., "Antigenic Characterization of the HCMV gH/ gL/ gO and Pentamer Cell Entry Complexes Reveals Binding Sites for Potently Neutralizing Human Antibodies", PLOS Pathogens, 11(10):1-20 (2015).
Coleman, et al., "Viral Glycoprotein Complex Formation, Essential Function and Immunogenicity in the Guinea Pig Model for Cytomegalovirus", PLOS ONE, 10(8):1-33 (2015).
Compton, et al., "An Immortalized Human Fibroblast Cell Line is Permissive for Human Cytomegalovirus Infection", Journal of Virology, 67:(6):3644-3648 (1993).
Corti, D., et al., "Efficient Methods to Isolate Human Monoclonal Antibodies from Memory B Cells and Plasma Cells", Microbiology Spectrum, 2(5):1-9 (2014).
Cox, MM, Hashimoto Y. A fast track influenza virus vaccine produced in insect cells. J Invertebr Pathol. Jul. 2011;107 Suppl:S31-41.
Cruz Cosme, R., et al., "Functional Interaction of Nuclear Domain 10 and its Components with Cytomegalovirus after Infections: Cross-Species Host Cells versus Native Cells", PLOS ONE, 6(4):e19187 (2011).
Daniel, V., et al., "HIV-Specific CD8(+) T Lymphocytes in Blood of Long-Term HIV-Infected Hemophilia Patients", BioResearch Open Access, 2(6):399-411 (2013).
Decrion, A., et al., "A Subset of Functional Effector-Memory CD8+ T Lymphocytes in Human Immunodeficiency Virus-Infected Patients", Immunology, 121(3)405-415 (2007).
deVries, et al., Rapid Genotyping of Cytomegalovirus in Dried Blood Spots by Multiplex Real-Time PCR Assays Targeting the Envelope Glycoprotein gB and gH Genes, Journal of Clinical Microbiology, 50(2)232-237 (2012).
Kropff, B., et al., "Glycoprotein N of Human Cytomegalovirus Protects the Virus From Neutralizing Antibodies", PLOS Pathogens 8(10):e1002999 1-15 (2012).
Kuntz, M., et al., Analysis of Bulk and Virus-Specific CD8+ T Cells Reveals Advanced Differentiation of CD8+ T Cells in Patients With Common Variable Immunodeficiency, Clinical Immunology, 141(2):177-186 (2011).
Landais, I., et al., "Human Cytomegalovirus miR-UL112-3p Targets TLR2 and Modulates the TLR2/IRAK1/NFkappaB Signaling Pathway", PLOS Pathogens, 11(5):e1004881, 1-21 (2015).
Lauron, E., et al., "Human Cytomegalovirus Infection of Langerhans-Type Dendritic Cells does not Require the Presence of the gH/ gL/ UL128-131A Complex and is Blocked After Nuclear Deposition of Viral Genomes in Immature Cells", Journal of Virology, 88(1):403-416 (2014).
Lee, S., et al., "Monitoring of Cytomegalovirus-Specific CD8+ T-Cell Response with Major Histocompatibility Complex Pentamers in Kidney Transplant Recipients", Transplantation Proceedings, 43(7):2636-2640 (2011).
Li, L., et al., "Glycoprotein H-Related Complexes of Human Cytomegalovirus: Identification of a Third Protein in the gCIII Complex", Journal of Virology, 71(4):3090-3097 (1997).
Li, G., et al., "A Viral Regulator of Glycoprotein Complexes Contributes to Human Cytomegalovirus Cell Tropism", PNAS, 112(14):4471-4476 (2015).
Li, Q., et al., "THY-1 Cell Surface Antigen (CD90) has an Important Role in the Initial Stage of Human Cytomegalovirus Infection", PLOS Pathogens, 11(7):E1004999, 1-26 (2015).
Lilja, A., et al., "Efficient Replication of Rhesus Cytomegalovirus Variants in Multiple Rhesus and Human Cell Types", PNAS, 105(50): 19950-19955 (2008).
Lilleri, D., et al., "Antibodies Against Neutralization Epitopes of Human Cytomegalovirus gH/ gL/ pUL128-130-131 Complex and Virus Spreading may Correlate with Virus Control in Vivo", Journal of Clinical Immunology, 32 (6):1324-1331 (2012).
Lilleri, D., et al., "Fetal Human Cytomegalovirus Transmission Correlates with Delayed Maternal Antibodies to gH/ gL/ pUL128-130-131 Complex During Primary Infection", PLOS ONE, 8(3):e59863, 1-13 (2013).
Liu, A., et al., "Evaluation of Human Cytomegalovirus-Specific CD8+ T-Cells in Allogeneic Haematopoietic Stem Cell Transplant Recipients Using Pentamer and Interferon-Gamma-Enzyme-Linked Immunospot Assays", Journal of Clinical Virology, 58(2):427-431 (2013).
Liu, A., et al., "Preliminary Exploration of HLA-A 1101-Restricted human Cytomegalovirus Glycoprotein B-Specific CD8+ T Cells in Allogeneic Stem-Cell Transplant Recipients", Virus Research, 188:38-44 (2014).
Liu, G., et al., "Protective MCMV Immunity by Vaccination of the Salivary Gland via Wharton's Duct: Replication Deficient Recombinant Adenovirus Expressing Individual MCMV Genes Elicits Protection Similar to that of MCMV", FASEB Journal, 28(4):1698-710 (2014).

(56) References Cited

OTHER PUBLICATIONS

Lipira, G., et al., "A Sealed and Unbreached System for Purification, Stimulation, and Expansion of Cytomegalovirus-Specific Human CD4 and CD8 T Lymphocytes", Transfusion 46(12):2053-2062 (2006).
Loomis, R., et al., "Vectored Co-Delivery of Human Cytomegalovirus gH and gL Proteins Elicits Potent Complement-Independent Neutralizing Antibodies", Vaccine, 31(6):919-926 (2013).
Lopper, M., et al., "Coiled-Coil Domains in Glycoproteins B and H are Involved in Human Cytomegalovirus Membrane Fusion", Journal of Virology, 78(15):8333-8341 (2004).
Loughney, J., et al., "Soluble Human Cytomegalovirus gH/ gL/ pUL128-131 Pentameric Complex, but not gH/ gL, Inhibits Viral Entry to Epithelial Cells and Presents Dominant Native Neutralizing Epitopes", Journal of Biological Chemistry, 290(26):15985-15995 (2015).
Ma, Y., et al., "Novel Transcripts of Human Cytomegalovirus Clinical Strain Found by cDNA Library Screening", Genetics & Molecular Research, 10(2):566-575 (2011).
Macagno, A., et al., "Isolation of Human Monoclonal Antibodies that Potently Neutralize Human Cytomegalovirus Infection by Targeting Different Epitopes on the gH/gL/UL128-131A Complex", Journal of Virology, 84(2):1005-1013 (2010).
Madi, N., et al., "Cytomegalovirus genotypes gB 1 and gH1 are the most predominant genotypes among renal transplant recipients in Kuwait", Transplantation Proceedings, 43(5):1634-1637 (2011).
Manley, K., et al., ""Human Cytomegalovirus Escapes a Naturally Occurring NeutralizingAntibody by Incorporating it into Assembling Virions"", Cell Host & Microbe, 10(3):197-209 (2011).
Mattick, C., et al., Linkage of Human Cytomegalovirus Glycoprotein gO Variant Groups Identified from Worldwide Clinical Isolates with gN Genotypes, Implications for Disease Associations and Evidence for N-Terminal Sites of Positive Selection, Virology, 318(2):582-597 (2004).
McCormick, L., et al., "The Immunological Underpinnings of Vaccinations to Prevent Cytomegalovirus Disease", Cellular and Molecular Immunology, 12(2):170-179 (2015).
McSharry, B., et al., "Human Cytomegalovirus Encoded Homologs of Cytokines, Chemokines and their Receptors: Roles in Immunomodulation", Viruses-Basel 4(11):2448-2470 (2012).
McVoy, M. et al., "Cytomegalovirus Vaccines", Clinical Infectious Diseases, 57(4):S196-199 (2013).
McVoy, M. et al., "A Cytomegalovirus DNA Vaccine Induces Antibodies that Block Viral Entry into Fibroblasts and Epithelial Cells", Vaccine, 33(51):7328-7336 (2015).
Meyer, H., et al., "Glycoprotein gp116 of Human Cytomegalovirus Contains Epitopes for Strain-Common and Strain-Specific Antibodies", Journal of General Virology, 73:2375-2383 (1992).
Mochizuki, T., et al., "Cucumber Mosaic Virus: Viral Genes as Virulence Determinants", Molecular Plant Pathology, 13(3):217-225 (2012).
Muller, "Pattern and Persistence of the Epitope-Specific IgM Response Against Human Cytomegalovirus in Renal Transplant Patients", Journal of Clinical Virology, 24(1-2):45-56 (2002).
Murhammer, D., "Ed Baculovirus and Inspect Cell Expression Protocols" 2nd Ed. Methods Mol Biol. 388 (2007).
Murrell, I., et al., Impact of Sequence Variation in the UL128 Locus on Production of Human Cytomegalovirus in Fibroblast and Epithelial Cells, Journal of Virology, 87(19):10489-10500 (2013).
Nejatollahi, F., et al., "Neutralising Human Recombinant Antibodies to Human Cytomegalovirus Glycoproteins gB and gH", FEMS Immunology & Medical Microbiology, 34(3):237:244 (2002).
Nellore A., et al., The Cyclin Dependent Kinase Inhibitor (R)-Roscovitine Mediates Selective Suppression of Alloreactive Human T cells but Preserves Pathogen-Specific and Leukemia-Specific Effectors, Clinical Immunology, 152(1-2):48-57 (2014).
Nie, Y., et al., "Multiprotein Complex Production in Insect Cells by Using Polyproteins", Methods Mol Biol., 1091:131-141 (2014).
Nogalski, M., et al., "The Human Cytomegalovirus Virion Possesses an Activated Casein Kinase II that Allows for the Rapid Phosphorylation of the Inhibitor of NF-kappaB, IkappaBalpha", Journal of Virology, 81(10):5305-5314 (2007).
Nogalski, M., et al., "The HCMV gH/gL/UL128-131 Complex Triggers the Specific Cellular Activation Required for Efficient Viral Internalization into Target Monocytes", PLOS Pathogens, 9(7):e1003463 1-20 (2013).
Ohlin, M., et al., "Human Antibody Technology and the Development of Antibodies Against Cytomegalovirus", Molecular Immunology, 67:153-170 (2015).
Okada, T., Ihara H, Ito R, Nakano M, Matsumoto K, Yamaguchi Y, Taniguchi N, Ikeda Y. N-Glycosylation engineering of lepidopteraninsect cells by the introduction of the betal ,4-N-acetylglucosaminyltransferase III gene. Glycobiology. Sep. 2010;20(9):1147-59.Epub Jun. 16, 2010.
Omoto, S., et al., Transcription of True Late (gamma2) Cytomegalovirus Genes RequiresUL92 Function that is Conserved among Beta-andGammaherpesviruses, Journal of Virology, 88(1):120-130 (2014).
Pachnio, A., et al., "The Cellular Localization of Human Cytomegalovirus Glycoprotein Expression Greatly Influences the Frequency and Functional Phenotype of Specific CD4+ T Cell Responses", Journal of Immunology, 195(8):3803-3815, (2015).
Pati, S., et al., "Strain-Specific Neutralizing Antibody Responses Against Human Cytomegalovirus Envelope Glycoprotein N", Clinical & Vaccine Immunology, 19(6):909-913 (2012).
Pati, S., et al., Genotypic Diversity and Mixed Infection in Newborn Disease and Hearing Loss in Congenital Cytomegalovirus Infection, Pediatric Infectious Disease Journal, 32(10):1050-1054 (2013).
Patrone, M., et al., Cytomegalovirus UL131-128 Products Promote gB Conformational Transition and gB-gH Interaction During Entry into Endothelial Cells, Journal of Virology, 81(20):11479-11488 (2007).
Patrone, M., et al., "Palmitoylation Strengthens Cholesterol-Dependent Multimerization and Fusion Activity of Human Cytomegalovirus Glycoprotein B (gB)", Journal of Bilogical Chemistry, 291(9):4711-4722 (2016).
Peppenelli, M., et al., "Human Cytomegalovirus Stimulates the Synthesis of Select Akt-Dependent Antiapoptotic Proteins during Viral Entry to Promote Survival of Infected Monocytes", Journal of Virology, 90(6):3138-3147 (2016).
Pepperl S., et al., "Dense Bodies of Human Cytomegalovirus Induce Both Humoral and Cellular Immune Responses in the Absence of Viral Gene Expression", Journal of Virology, 74(13):6132-6146 (2000).
Plotkin, S., "Vaccination Against Cytomegalovirus, the Changeling Demon", Pediatric Infectious Disease Journal, 18(4):313-326 (1999).
Vogel, J. et al., "Role of human Cytomegalovirus genotype polymorphisms in AIDS patients with Cytomegalovirus retinitis", Medical Microbiology & Immunology 202(1):37-47 (2013).
Vomaske, J., et al., "Cytomegalovirus CC Chemokine Promotes Immune Cell Migration", Journal of Virology, 86(21):11833-11844 (2012).
Wallace, D., et al., "Human Cytomegalovirus-Specific CD8(+) T-Cell Expansions Contain Long-Lived Cells that Retain Functional Capacity in Both Young and Elderly Subjects", Immunology, 132(1):27-38 (2011).
Wang, D., et al., "Human Cytomegalovirus Virion Protein Complex Required for Epithelial and Endothelial Cell Tropism", PNAS, 102(50):18153-18158 (2005).
Wang, D., et al., "Progress on Human Cytomegalovirus Vaccines for Prevention of Congenital Infection and Disease", Current Opinion in Virology, 6(1):13-23 (2014).
Wang. X., et al., "Integrin $\alpha v\beta 3$ is a Coreceptor for Human Cytomegalovirus", Nature Medicine, 11(5):515-521 (2005).
Wen, Y., et al., Human Cytomegalovirus gH/ gL/ UL128/UL130/ UL131A Complex Elicits Potently Neutralizing Antibodies in Mice, Vaccine, 32(30):3796-37804 (2014).
Wilkinson, G., et al., "Human Cytomegalovirus: Taking the Strain", Medical Microbiology and Immunology, 204(3):273-284 (2015).
Wille, P., et al., "A Human Cytomegalovirus gO-null Mutant Fails to Incorporate gH/gL into the Virion Envelope and is Unable to Enter Fibroblasts and Epithelial and Endothelial Cells", Journal of Virology, 84(5):2585-2596 (2010).

(56) References Cited

OTHER PUBLICATIONS

Wille, P., et al., "Human Cytomegalovirus (HCMV) Glycoprotein gB Promotes Virus Entry in Trans Acting as the Viral Fusion Protein Rather than as a Receptor-Binding Protein", MBIO.ASM.ORG, 4(3): e00332-13 1-9 (2013).
Woo, P., et al., "Distinct Genotypic Distributions of Cytomegalovirus (CMV) Envelope Glycoprotein in Bone Marrow and Renal Transplant Recipients with CMV Disease", Clinical & Diagnostic Laboratory Immunology, 4(5):515-518 (1997).
Wreghitt, T., et al., "Differentiation of Human Cytomegalovirus (CMV) Glycoprotein B and Glycoprotein H Types by Restriction Fragment Length Polymorphism: Association of Glycoprotein Types with CMV Disease in Heart, Heart-Lung and Lung Transplant Recipients", Journal of Heart & Lung Transplantation, 18(1):82 (1999).
Wu, S., et al., "Synthetic DNA Approach to Cytomegalovirus Vaccine/Immune Therapy", Advances in Experimental Medicine and Biology, 848:131-148 (2015).
Wussow, F., et al., "A Vaccine Based on the Rhesus Cytomegalovirus UL128 Complex Induces Broadly Neutralizing Antibodies in Rhesus Macaques", Journal of Virology, 87(3):1322-1332 (2013).
Wussow, F., et al., "Human Cytomegalovirus Vaccine Based on the Envelope gH/ gLpentamer Complex", PLOS Pathogents, 10(11):e1004524 1-23, (2014).
Yamada, S., et al., "Characterization of the Guinea Pig Cytomegalovirus Genome Locus that Encodes Homologs of Human Cytomegalovirus Major Immediate-Early Genes, UL128, and UL130", Virology, 391(1):99-106 (2009).
Yamada, S., et al., "Guinea Pig Cytomegalovirus GP129/131/133, Homologues of Human Cytomegalovirus UL128/130/131A, are Necessary for Infection of Monocytes and Macrophages", Journal of General Virology, 95(Pt6):1376-1382 (2014).
Yamada, S., et al., "An Ex Vivo Culture Model for Placental Cytomegalovirus Infection Using Slices of Guinea Pig Placental Tissue", Placenta, 37:85-88 (2016).
Yamamoto, A., et al., "Diagnosis of Congenital and Perinatal Infection by Cytomegalovirus Using Polymerase Chain Reaction]. [Portuguese] Diagnostico de Infeccao Congenita e Perinatal Por Citomegalovirus Utilizando a Reacao em Cadeia da Polimerase" Revista Da Sociedade Brasileira de Medicina Tropical, 31(1):19-26 (1998), (abstract only).
Yao, J., "Multimer staining of Cytomegalovirus Phosphoprotein 65-specific T Cells for Diagnosis and Therapeutic Purposes: a Comparative Study", Clinical Infectious Diseases, 46(10):E96-105 (2008).
Yurochko, A., et al., "The Human Cytomegalovirus UL55 ( gB ) and UL75 (gH) Glycoprotein Ligands Initiate the Rapid Activation of Sp1 and NF-kappaB During Infection", Journal of Virology, 719(7):5051-5059 (1997).
Yurochko, A., et al., "Human Cytomegalovirus Binding to Human Monocytes Induces Immunoregulatory Gene Expression", Journal of Immunology, 162(8):4806-4816 (1999).
Zheng, Q., et al., "HCMV-Encoded UL128 Enhances TNF-alpha and IL-6 Expression and Promotes PBMC Proliferation Through the MAPK/ERK Pathway In Vitro", Viral Immunology, 25(2):98-105 (2012).
Zhou, L., et al., "Genetic Variation Within the Glycoprotein B and H Genes of Human Cytomegalovirus in Solid Organ Transplant Recipients", Transplant Infectious Disease, 9(1):73-77 (2007).
Zhou, M., et al., "Comparative Analysis of gO Isoforms Reveals that Strains of Human Cytomegalovirus Differ in the Ratio of gH/ gL/ gO and gH/ gL/ UL128-131 in the Virion Envelope", Journal of Virology, 87(17):9680-9690, (2013).
Zhou, M., et al., "Human Cytomegalovirus gH/ gL/ gO Promotes the Fusion Step of Entry into All Cell Types, whereas gH/ gL/ UL128-131 Broadens Virus Tropism through a Distinct Mechanism", Journal of Virology, 89(17):8999-9009 (2015).
Zipeto, D., et al., "Human Cytomegalovirus (CMV) DNA in plasma reflects quantity of CMV DNA present in leukocytes", Journal of Clinical Microbiology, 33(10):2607-2611 (1995).
Zydek, M., et al., "HCMV Infection of Human Trophoblast Progenitor Cells of the Placenta is Neutralized by a Human Monoclonal Antibody to Glycoprotein B and not by Antibodies to the Pentamer Complex", Viruses, 6(3):1346-1364 (2014).
Burke, H.G., et al.,"Crystal Structure of the Human Cytomegalovirus Glycoprotein B", PLOS, 11(10): e1005227 21 pages (2015).
Chadramouli, S., et al., "Structure of HCMV Glycoprotein B in the Postfusion Conformation Bound to a Neutralizing Human Antibody", Nature Communications, pp. 1-12 (2015).
Ciferri, C., et al., "Structural and Biochemical Studies of HCMV gH/gl/gO and Pentamer Reveal Mutually Exclusive Cell Entry Complexes", PNAS, 112(6) 1767-1772 (2015).
Hoffmann, I., et al., "Expression of the Human Cytomegalovirus Pentamer Complex for Vaccine Use in a CHO System," Biotechnology and Bioengineering, 112(12): 2505-2515 (2015).
Pass, R.F., et al., "A Subunit Cytomegalovirus Vaccine Based on Recombinant Envelope Glycoprotein B and a New Adjuvant" The Journal of Infectious Diseases 180:970-975 (1999).
Database Geneseq Online, "Cytomegalovirus Glygoprotein B (gB)-SLP12-Delta725 polypeptide, SEQ 10", XP002769687, Database accession No. AZV29616, Jun. 7, 2012.
Database Uniprot Online, "Envelope Glycoprotein B, Human Cytomegalovirus", XP002769688, Database accession No. V9LN55, Mar. 19, 2014.
Database Uniprot Online, "Envelope Glycoprotein B, Macanine Betaherpesvirus 3, Rhesus Cytomegalovirus" XP002769689, Database accession No. D5KB35, Jun. 15, 2010.
Sharma,S., et al., "HCMV gB Shares Structural and Functional Properties with gB Proteins from other Herpesvirus", Virology, 435: 239-249 (2013).
Smith, G., et al., "Respiratory Syncytial Virus Fusion Glycoprotein Expressed in Insect Cells Form Protien Nanoparticles that Induce Protective Immunity in Cotton Rats", PLOS, 7(11): e50852 12 pages (2012).
Zeev-Ben-Mordehai, T., et al., "Two Distinct Trimeric Conformations of Natively Membrane-Anchored Full-Length Herpes Simplex Virus 1 Glycoprotein B", PNAS, 17 pages (2016).
Plotkin, S., "The history of Vaccination Against Cytomegalovirus", Medical Microbiology & Immunology, 204(3):247-254 (2015).
Ramirez, N., et al., "Viral-Specific Adoptive Immunotherapy After allo-SCT: The role of Multimer-Based Selection Strategies", Bone Marrow Transplantation, 48(10):1265-1270 (2013).
Rasmussen, L., et al., "Cytomegalovirus gB Genotype Distribution Differs in Human Immunodeficiency Virus-Infected Patients and Immunocompromised Allograft Recipients", Journal of Infecious Diseases, 175(1):179-184 (1997).
Rasmussen, L., et al., "Inter- and Intragenic Variations Complicate the Molecular Epidemiology of Human Cytomegalovirus", Journal of Infectious Diseases, 187(5):809-819 (2003).
Rautenberg, P., et al., "Evaluation of the AmpliSensor PCR and the SHARP Signal Detection System for the Early Prediction of Symptomatic CMV Infection in Solid Transplant Recipients", Journal of Clinical Virology, 13(1-2):81-94 (1999).
Reschke, M., et al., "Constitutive Expression of Human Cytomegalovirus (HCMV) Glycoprotein gpUL75 (gH) in Astrocytoma Cells: a Study of the Specific Humoral Immune Response", Viral Immunology, 12(3):249-262 (1999).
Revello, M., et al., "Human Cytomegalovirus Tropism for Endothelial/ Epithelial Cells: Scientific Background and Clinical Implications", Reviews in Medical Virology, 20(3):136-155 (2010).
Rieder, F., "Cytomegalovirus Vaccine: Phase II Clinical Trial Results", Clinical Microbiology & Infection, 20(5):95-102 (2014).
Rivailler, P., "Genomic Sequence of Rhesus Cyomegalovirus 180. 92: Insights into the Coding Potential of Rhesus Cytomegalovirus", J Virol., 80(8):4179-4182 (2006).
Roubalova, K., "Genetic Variability of Cytomegalovirus Glycoprotein O in Hematopoietic Stem Cell Transplant Recipients", Transplant Infectious Disease, 13(3):237-243 (2011).
Ryckman, B.J., et al., "Characterization of the Human Cytomegalovirus gH/gL/UL128-131 Complex That Mediates Entry into Epithelial and Endothelial Cells", Journal of Virology, 81(1):60-70 (2008).

(56) References Cited

OTHER PUBLICATIONS

Ryckman, B., et al., "Human Cytomegalovirus Entry into Epithelial and Endothelial Cells Depends on Genes UL128 to UL150 and Occurs by Endocytosis and Low-pH Fusion", Journal of Virology, 80(2):710-722 (2006).

Ryckmann, B., et al., "HCMV gH/ gL/ UL128-131 Interferes with Virus Entry into Epithelial Cells: Evidence for Cell Type-Specific Receptors", PNAS, 105(37):14118-14123 (2008).

Saccoccio, F., et al., "Peptides From Cytomegalovirus UL130 and UL131 Proteins Induce High Titer Antibodies that Block Viral Entry into Mucosal Epithelial Cells", Vaccine, 29(15):2705-2711 (2011).

Sanchez, V. et al., "Accumulation of Virion Tegument and Envelope Proteins in a Stable Cytoplasmic Compartment During Human Cytomegalovirus Replication:Ccharacterization of a Potential Site of Virus Assembly", Journal of Virology, 74(2):975-986 (2000).

Sanchez, V. et al., "Viable Human Cytomegalovirus Recombinant Virus with an Internal Deletion of the IE2 86 Gene Affects Late Stages of Viral Replication", Journal of Virology, 76(6):2973-2989 (2002).

Sandalova, E., et al., Contribution of Herpesvirus Specific CD8 T Cells to Anti-Viral T Cell Response in Humans, PLOS Pathogens, 6(8): e1001051 1-12 (2010).

Satterwhite, T., et al., "Increased Expression of Cytotoxic Effector Molecules: Different Interpretations for Steroid-Based and Steroid-Free Immunosuppression", Pediatric Transplantation, 7(1) 53-58 (2003).

Schleiss, M., "Cytomegalovirus Vaccine Development", Current Topics in Microbiology and Immunology, 325:361-382 (2008).

Schleiss, M., "Cytomegalovirus Vaccine Strategies", Expert Opinion on Therapeutic Patents, 18(4): 375-385 (2008).

Schleiss, M., et al., "Cytomegalovirus Vaccines and Methods of Production (WO20009049138): the Emerging Recognition of the Importance of Virus Neutralization at the Epithelial/Endothelial Interface", Expert Opinion on Therapeutic Patents, 20(4):597-602 (2010).

Schleiss, M., et al., "Preventing Congenital Cytomegalovirus Infection: Protection to a 'T'", Trends in Microbiology, 24(3):170-172 (2016).

Schleiss, M., "Cytomegalovirus Vaccine Under Development", Journal of Virus Eradication, 2(4): 198-207 (2016).

Schuessler, A., et al., "Charge Cluster-to-Alanine Scanning of UL128 for Fine Tuning of the Endothelial Cell Tropism of Human Cytomegalovirus", Journal of Virology, 82(22):11239-11246 (2008).

Schuessler, A., et al., "Mutational Mapping of pUL131A of Human Cytomegalovirus Emphasizes its Central Role for Endothelial Cell Tropism", Journal of Virology, 86(1):504-512 (2012).

Schultz, E., et al., "Scanning Mutagenesis of Human Cytomegalovirus Glycoprotein gH/ gL", Journal of Virology, 90(5):2294-2305 (2015).

Scrivano, L. et al, "HCMV Spread and Cell Tropism are Determined by Distinct Virus Populations", PLOS Pathogen, 7(1)e1001256 1-12 (2011).

Seedah, E., et al., "Immunotherapeutic Approaches to Prevent Cytomegalovirus-Mediated Disease", Microbiology Spectrum, 2(1): 1-12 (2014).

Shi, X., Harrison RL, Hollister JR, Mohammed A, Fraser MJ Jr, Jarvis DL. Construction and characterization of new piggyBac vectorsfor constitutive or inducible expression of heterologous gene pairs and the identification of a previously unrecognized activatorsequence in piggyBac. BMC Biotechnol. 7:5 (2007).

Sindre, H., et al., "Human Cytomegalovirus Induced Inhibition of Hematopoietic Cell Line Growth is Initiated by Events Taking Place Before Translation of Viral Gene Products", Archives of Virology, 145(1):99-111 (2000).

Sinzger, C., et al., "Cytomegalovirus Cell Tropism", Current Topics in Microbiology & Immunology, 325:63-83 (2008).

Spear, P., et al., "Herpesvirus entry: An update", Journal of Virology, 77(19):10179-10185 (2003).

Spindler, N., et al., "Structural Basis for the Ecognition of Human Cytomegalovirus Glycoprotein B by a Neutralizing Human Antibody", PLOS Pathogens, 10(10): e1004377 1-15 (2014).

Steininger, C., et al., "Frequency Distribution and Genetic Distances of CMV Strains Found in Different Clinical Specimens from Immunocompetent and Inummocompromised Patients", Infection Genetics & Evolution, 5(3):305 (2005).

Stock, D., et al., "The Evolution of the Vertebrate D1x Gene Family", Proc. Natl. Acad. Sci, 93:10858-10863 (1996).

Straschewski, S., et al., "The Gene Region UL128-UL131A of Human Cytomegalovirus (HCMV) is Essential for Monocyte Infection and Block of Migration:Characterization of the Infection of Primary Human Monocytes", (2010).

Straschewski, S., et al., "Protein pUL128 of Human Cytomegalovirus is Necessary for Monocyte Infection and Blocking of Migration", Journal of Virology, 85(10):5150-5158 (2011).

Sung, H., et al., "Update on the Current Status of Cytomegalovirus Vaccines", Expert Review of Vaccines, 9(11):1303-1314 (2010).

Swanson, E., et al., "Comparison of Monovalent Glycoprotein B with Bivalent gB /pp65 (GP83) Vaccine for Congenital Cytomegalovirus Infection in a Guinea Pig Model: Inclusion of GP83 Reduces gB Antibody Response but Both Vaccine Approaches Provide Equivalent Protection Against Pup Mortality", Vaccine, 33(32):4013-4018 (2015).

Tang, X.C., et al., "Baculovirus-Produced Influenza Virus-Like Particles in Mammalian Cells Protect Mice from Lethal Influenza Challenge", Viral Immunology, 24(4):311-319 (2011).

Terpe, K., "Overview of Tag Protein Fusions: From Molecular and Biochemical Fundamentals to Commercial Systems", Appl Microbiol Biotechnol, 60(5):523-33 (2003).

Tischer, S., et al., "Heat Shock Protein 70/Peptide Complexes: Potent Mediators for the Generation of Antiviral T Cells Particularly with Regard to Low Precursor Frequencies", Journal of Translational Medicine 9(1): 1-14 (2011).

Vanarsdall, A., et al., "Human Cytomegalovirus Glycoproteins gB and gH/ gLmediate Epithelial Cell-Cell Fusion When Expressed Either in cis or in trans", Journal of Virology, 82(23):11837-11850 (2008).

Vanarsdall, A., et al., "Human Cytomegalovirus Glycoprotein gO Complexes with gH/ gL, Promoting Interference with Viral Entry into Human Fibroblasts but not Entry into Epithelial Cells", Journal of Virology, 85(22):11638-11645 (2011).

Vanarsdall, A., et al., "PDGF Receptor-Alpha does not Promote HCMV Entry into Epithelial and Endothelial Cells but Increased Quantities Stimulate Entry by an Abnormal Pathway", PLOS Pathogens, 8(9):e1002905 1-15 (2012).

Vanarsdall, A., et al., "Human Cytomegalovirus Entry into Cells", Current Opinion in Virology, 2(1):37-42 (2012).

Van Zanten, J., et al., "Humoral Immune Response Against Human Cytomegalovirus (HCMV)-Specific Proteins After HCMV Infection in Lung Transplantation as Detected With Recombinant and Naturally Occurring Proteins", Clinical & Diagnostic Laboratory Immunology, 2(2):214-218 (1995).

Vijayachandran, L., et al., "Gene Gymnastics: Synthetic Biology for Baculovirus Expression Vector System Engineering", Bioengineered, 4:(5):279-287 (2013).

Vogel, J. et al., "Model for the Evaluation of Novel antivirals to Prevent HCMV Dissemination", Antiviral Research, 50(1) A66 (2001).

FIG. 2

>HCMV VR1814 gB705
ESRIWCLVVCVNLCIVCLGAVVSSSSTSHATSSAHNGSHTSRTTSAQTRSVSSQHVTSS
EAVSHRANETIYNTTLKYGDVVGVNTTKYPYRVCSMAQGTDLIRFERNIVCTPMKPINED
LDEGIMVVYKRNIVAHTFKVRVYQKVLTFRRSYAGHRTTYLLGSNTEYVAPPMWEIHHIN
RHSQCYSSYSRVIAGTVFVAYHRDSYENKTMQLMLDDYSNTHSTRYVTVKDQWHSRGSTA
LYRETCNLNCMVTITTARSKYPYHFFATSTGDVVDISPFYNGTNRNTSYFGENADKFFIF
PNYTIVSDFGRANSAPETHRLVAFLERADSVISWDIQDEKNVTCQLTFWEASERTIRSEA
EDSYHFSSAKMTATFLSKKQEVNMSDPVLDCVRDQALNKLQQIFNASYNQTYEKYGNVSV
FETTGGLVVFWQGIKQKSLLELERLANSSGVNSTRATKASTGNTTTLSLESESVRNVLYA
QLQFTYDTLRSYINRALAQIAEAWCVDQRRTLEVFKELSKINPSAILSAIYNKPIAARFM
GDVLGLASCVTINQTSVKVLRDMNVKESPGRCYSRPVVIFNFVNSSYVQYGQLGEDNEIL
LGNHRTEECQFPSLKIFIAGNSAYEYVDYLFKRMIDLSSISTVDSMIALDIDPLENTDFR
VLELYSQKELRSSNVFDLEEIMREFNSYKQRVKYVEDKVVDPLPP (SEQ ID NO: 2)

FIG. 8C
gB705 pH5.2          gB705 pH8.7
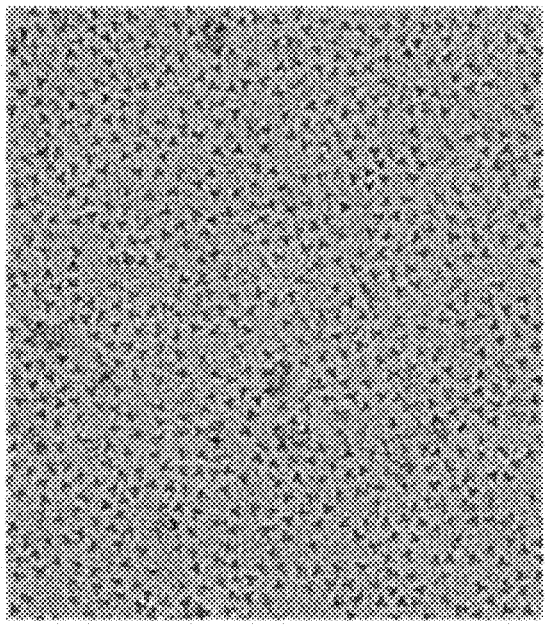 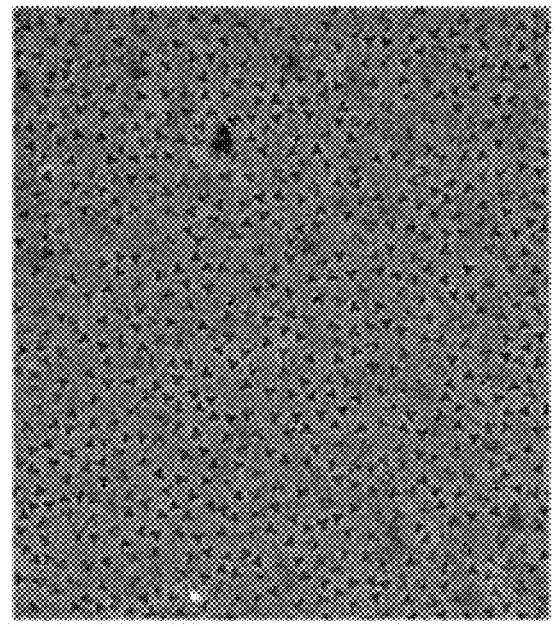

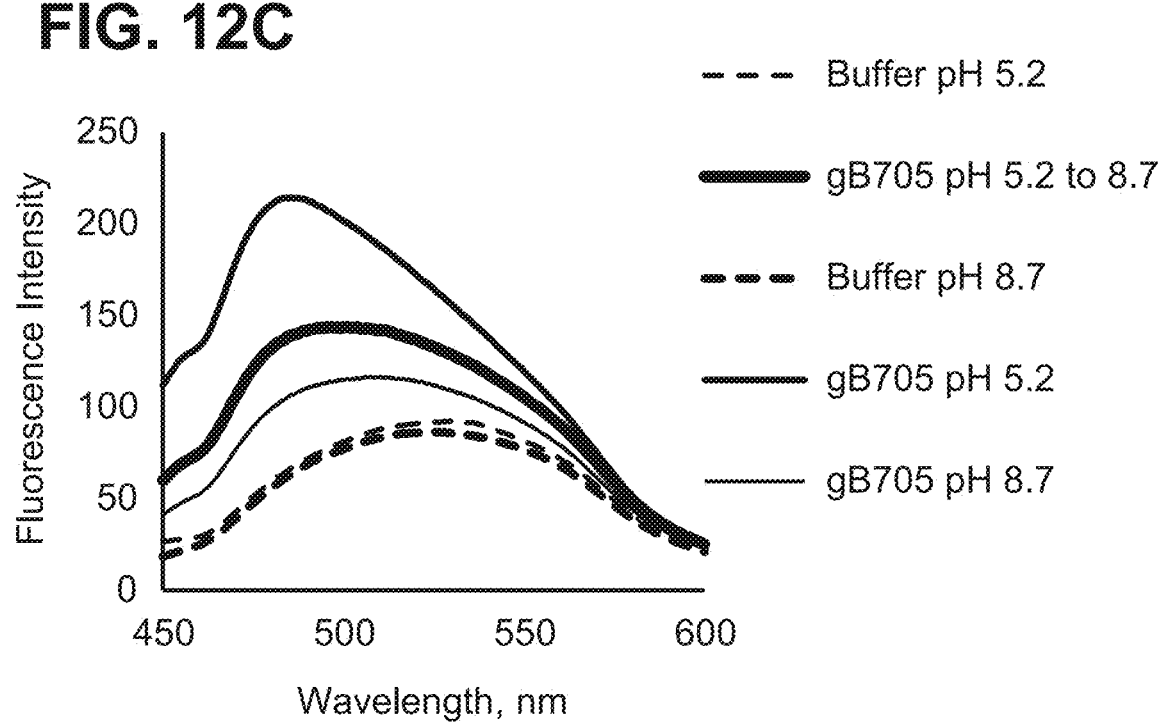

Pentamer + gB

HUMAN CYTOMEGALOVIRUS GB POLYPEPTIDE

CROSS REFERENCE TO RELATED APPLICATIONS

This application is a 35 U.S.C § 371 national stage application of International Patent Application PCT/IB2017/051401 filed on Mar. 9, 2017, which claims priority from U.S. provisional application No. 62/463,982, filed on Feb. 27, 2017, and U.S. provisional application No. 62/307,423, filed on Mar. 11, 2016, each of which is hereby incorporated by reference in its entirety.

FIELD OF THE INVENTION

The present invention relates to human cytomegalovirus (HCMV) compositions and methods thereof.

BACKGROUND

Human cytomegalovirus (HCMV) is a double stranded DNA virus of the β-herpesvirus family. HCMV is the leading cause of congenital and neonatal hearing loss resulting from vertical virus transmission following infection or reactivation of latent virus in pregnant women. In addition, HCMV is a common opportunistic pathogen affecting immunosuppressed transplant patients, such as solid organ/stem cell transplant patients, AIDS patients, etc. Though development of a vaccine against HCMV has been listed as a top priority by the Institute of Medicine, none has been licensed to date.

The HCMV genome encodes several envelope glycoproteins, one of which is glycoprotein B (gB). Glycoprotein B is an important surface target for neutralizing antibody (nAb) response in natural infection and is required for virus entry into cells by functioning as a fusogen.

HCMV subunit vaccines incorporating gB have been under development. Studies have suggested that gB subunit vaccines were safe and immunogenic, though further improvements in potency and durability of protection were desirable.

Accordingly, safe and effective immunogenic compositions against cytomegalovirus infections, as well as diagnostic reagents capable of detecting immunogenic stimuli resulting from CMV infections, guiding the design of gB-based HCMV vaccines, and/or supporting the development of therapeutic antibodies against this medically relevant human pathogen are needed.

SUMMARY OF THE INVENTION

To meet these and other needs, in one aspect, the present invention relates to a polypeptide that includes at least one mutation in the fusion loop 1 (FL1) region of an HCMV gB polypeptide.

In one aspect, the invention relates to a polypeptide that includes at least one mutation in the fusion loop 2 (FL2) region of an HCMV gB polypeptide.

In one aspect, the invention relates to a polypeptide that includes at least one mutation in the fusion loop 1 (FL1) region and the fusion loop 2 (FL2) region of an HCMV gB polypeptide.

In one aspect, the invention relates to a polypeptide that includes at least one mutation in the furin-like cleavage site of an HCMV gB polypeptide.

In one aspect, the invention relates to a polypeptide that includes at least two mutations in the fusion loop 2 (FL2) region of an HCMV gB polypeptide.

In one aspect, the invention relates to a polypeptide that includes at least two mutations in the fusion loop 1 (FL1) region and the fusion loop 2 (FL2) region of an HCMV gB polypeptide.

In one aspect, the invention relates to a polypeptide that includes at least two mutations in the furin-like cleavage site of an HCMV gB polypeptide.

In one aspect, the invention relates to a polypeptide that includes a mutation at position Y155, as compared to SEQ ID NO: 6.

In one aspect, the invention relates to a polypeptide that includes a mutation at positions Y155 and I156, as compared to SEQ ID NO: 6.

In one aspect, the invention relates to a polypeptide that includes a mutation at positions Y155, I156, and H157, as compared to SEQ ID NO: 6.

In one aspect, the invention relates to a polypeptide that includes a mutation at positions I156 and H157, as compared to SEQ ID NO: 6.

In one aspect, the invention relates to a polypeptide that includes a mutation at positions Y155, I156, H157, and W240, as compared to SEQ ID NO: 6.

In one aspect, the invention relates to a polypeptide that includes a mutation at positions Y155 and W240, as compared to SEQ ID NO: 6.

In one aspect, the invention relates to a polypeptide that includes a mutation at positions Y155, H157, and W240, as compared to SEQ ID NO: 6.

In one aspect, the invention relates to a polypeptide that includes a mutation at positions Y155 and H157, as compared to SEQ ID NO: 6.

In one aspect, the invention relates to a polypeptide that includes the mutation Y155G, as compared to SEQ ID NO: 6.

In one aspect, the invention relates to a polypeptide that includes the mutations Y155G and I156H, as compared to SEQ ID NO: 6.

In one aspect, the invention relates to a polypeptide that includes the mutations Y155G, I156H, and H157R, as compared to SEQ ID NO: 6.

In one aspect, the invention relates to a polypeptide that includes the mutations I156H and H157R, as compared to SEQ ID NO: 6.

In one aspect, the invention relates to a polypeptide that includes the mutations Y155G, I156H, H157R, and W240A, as compared to SEQ ID NO: 6.

In one aspect, the invention relates to a polypeptide that includes the mutations Y155G and W240A, as compared to SEQ ID NO: 6.

In one aspect, the invention relates to a polypeptide that includes the mutations Y155G, H157R, and W240A, as compared to SEQ ID NO: 6.

In one aspect, the invention relates to a polypeptide that includes the mutations Y155G and H157R, as compared to SEQ ID NO: 6.

In one aspect, the invention relates to a polypeptide that includes an amino acid sequence that is at least about 60% identical to SEQ ID NO: 1.

In one aspect, the invention relates to a polypeptide that includes an amino acid sequence that is at least about 60% identical to SEQ ID NO: 2.

In one aspect, the invention relates to a polypeptide that includes an amino acid sequence that is at least about 60% identical to SEQ ID NO: 3.

In one aspect, the invention relates to a polypeptide that includes an amino acid sequence that is at least about 60% identical to SEQ ID NO: 5.

In one aspect, the invention relates to a polypeptide that includes an amino acid sequence that is at least about 60% identical to SEQ ID NO: 7.

In one aspect, the invention relates to a polypeptide that includes an amino acid sequence that is at least about 60% identical to SEQ ID NO: 8.

In one aspect, the invention relates to a polypeptide that includes the amino acid sequence set forth in SEQ ID NO: 1.

In one aspect, the invention relates to a polypeptide that includes the amino acid sequence set forth in SEQ ID NO: 2.

In one aspect, the invention relates to a polypeptide that includes the amino acid sequence set forth in SEQ ID NO: 3.

In one aspect, the invention relates to a polypeptide that includes the amino acid sequence set forth in SEQ ID NO: 5.

In one aspect, the invention relates to a polypeptide that includes the amino acid sequence set forth in SEQ ID NO: 7.

In one aspect, the invention relates to a polypeptide that includes the amino acid sequence set forth in SEQ ID NO: 8.

In one embodiment, the polypeptide does not include a mutation at any one of the following positions: (i) R236, (ii) G237, (iii) T158; (iv) Y242. In one embodiment, the polypeptide does not include any one of the following mutations: (i) R236N, (ii) G237N, (iii) T158N; (iv) Y242T, (v) Y242S; (vi) Y242C. In one embodiment, the amino acid sequence SEQ ID NO: 9 is a part of the polypeptide sequence. In one embodiment, the amino acid sequence SEQ ID NO: 10 is a part of the polypeptide sequence. In one embodiment, the amino acid sequences of SEQ ID NO: 9 and SEQ ID NO: 10 is a part of the polypeptide sequence. In one embodiment, the polypeptide does not include a protease cleavage site. In one embodiment, the polypeptide does not include a wild-type CMV protease cleavage site. In one embodiment, the polypeptide does not include a non-naturally occurring protease cleavage site that replaces the wild-type CMV protease cleavage site. In one embodiment, the polypeptide does not include an N-glycosylation site that includes N-X-S/T/C motif, wherein X is any amino acid residue. In one embodiment, the polypeptide does not include a modified amino acid sequence that introduces an O-linked glycosylation site. In one embodiment, the polypeptide does not include a deletion or substitution of any one of the amino acid residues selected from the group consisting of 154, 158, 159, 160, 230, 231, 232, 233, 234, 235, 236, 237, 238, 239, 241, and 242, according to the numbering of SEQ ID NO: 6. In one embodiment, the polypeptide does not include a mutation of any one of the amino acid residues: Y160, R236, S238, T239, and Y242, according to the numbering of SEQ ID NO: 6. In one embodiment, the polypeptide does not include the cytoplasmic tail of HCMV gB.

In one embodiment, the polypeptide does not contain an insect cell pattern of glycosylation. In one embodiment, the polypeptide is contacted with ethylenediaminetetraacetic acid (EDTA).

In one aspect, the invention relates to a composition that includes the polypeptide described herein, and a diluent.

In one aspect, the invention relates to a composition that includes the polypeptide described herein, and an adjuvant. In one embodiment, the composition is immunogenic. In one embodiment, the composition is for use in inducing an immune response against cytomegalovirus.

In one aspect, the invention relates to a recombinant nucleic acid molecule encoding the polypeptide described herein, wherein the polypeptide undergoes a structural conformation change in response to a pH change. In one embodiment, said recombinant nucleic acid (a) is not a self-replicating RNA molecule; (b) is not an alphavirus replicon; (c) does not encode any alphavirus nonstructural proteins, such as NSP1, NSP2, NSP3 and NSP4; (d) does not contain: an Internal Ribosomal Entry Site (IRES), such as EMCV or EV71; and/or (e) does not contain a viral 2A site, such as FMDV.

In one aspect, the invention relates to a method for raising antibodies using the polypeptide described herein. In one embodiment, said antibody is for use in a diagnostic assay. In one embodiment, said antibody is labelled directly or indirectly. In one embodiment, said antibody is for use in therapy.

In one aspect, the invention relates to a method of eliciting an immune response in a mammal, the method that includes administering to the mammal an effective amount of the polypeptide described herein.

BRIEF DESCRIPTION OF THE DRAWINGS

FIG. 2—sequence of HCMV gB705 (SEQ ID NO: 2).

FIG. 4B Binding of human anti-HCMV gB monoclonal antibodies to Sino gB protein (gB from Sino Biologicals, Inc.) (ELN #00710043-0177).

FIG. 8A-C—Sedimentation velocity analysis of EDTA-treated gB705 at pH 5.2 (FIG. 8A) and pH 8.7 (FIG. 8B); Cryo electron microscopy analysis of EDTA-treated gB705 proteins pH 5.2 (left) or pH 8.7 (right) (FIG. 8C)

FIG. 9B intrinsic fluorescence spectroscopy (ELN #00708337-0115, 0117) of gB705 at pH 5.2 and pH 8.7.

FIG. 12A-C—(A) ANS binding of gB705 at pH 5.2, pH 7.4 and pH 8.7 (ELN #00708337-0115, 0117); (B) ANS binding of gB705 at pH 8.7 and 5.2 and shifted from pH 8.7 to pH 5.2; (C) ANS binding of gB705 at pH 8.7 and 5.2 and shifted from pH 5.2 to pH 8.7 (ELN #00708329-0153)

SEQUENCE IDENTIFIERS

Figure 1:
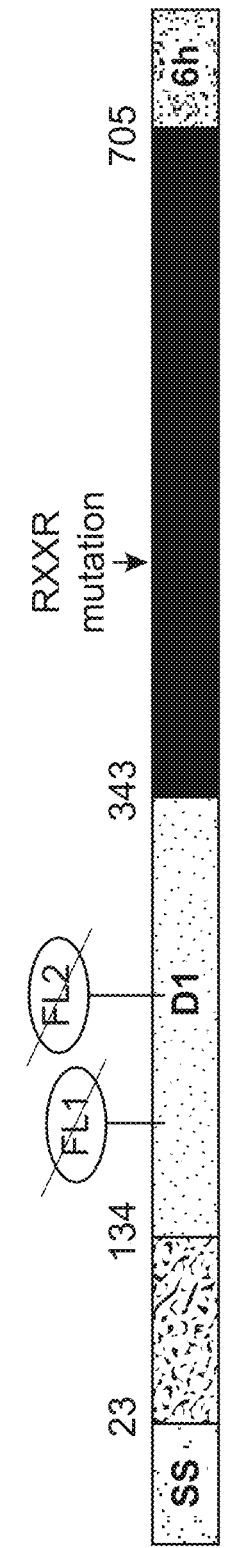
FIG. 1—illustration of HCMV gB705(SEQ ID NO: 1). SS represents a signal sequence; D1 represents the Domain I; FL represents a fusion loop; RxxR mutation represents knock-out mutations of the furin-like cleavage site; 6 h represents an optional 6× His tag.

SEQ ID NO: 1 sets forth the amino acid sequence for HCMV VR1814 gB705.

SEQ ID NO: 2 sets forth the amino acid sequence for HCMV VR1814 gB705, without an initial methionine. SEQ ID NO: 2 is identical to SEQ ID NO: 1 but for the absence of the initial methionine.

SEQ ID NO: 3 sets forth the amino acid sequence for a fragment of HCMV VR1814 gB705 (residues 25-705 OF SEQ ID NO: 1).

SEQ ID NO: 4 sets forth the amino acid sequence for the signal sequence of an HCMV VR1814 gB.

SEQ ID NO: 5 sets forth the amino acid sequence for HCMV VR1814 gB705 with linker SEQ ID NO: 6 sets forth the amino acid sequence for GenBank Accession # ACZ79977.1 for envelope glycoprotein B of strain VR1814 [Human beta-herpesvirus 5].

SEQ ID NO: 7 sets forth the amino acid sequence for an analogous construct of HCMV gB705 construct, named as RhCMV gB674, which was designed and tested in RhCMV (−) monkeys SEQ ID NO: 8 sets forth the amino acid sequence for an analogous construct of HCMV gB705 construct, named as RhCMV gB674, which was designed and tested in RhCMV (−) monkeys, without an initial methionine. SEQ ID NO: 8 is identical to SEQ ID NO: 7 but for the absence of the initial methionine.

SEQ ID NO: 9 sets forth the amino acid sequence for VVDPLPP$^{705}$, a part of the membrane proximal region (MPR) of HCMV gB.

SEQ ID NO: 10 sets forth the amino acid sequence for RA$^{457}$TKA$^{459}$S.

SEQ ID NO: 11 sets forth the amino acid sequence for GenBank Accession # GU552457.1 for macacine herpesvirus 3 isolate 21252 glycoprotein B (RhUL55).

SEQ ID NO: 12 sets forth the amino acid sequence for the predicted fusion loop 1 region of the envelope glycoprotein B of strain VR1814 [Human beta-herpesvirus 5], from GenBank Accession # ACZ79977.1.

SEQ ID NO: 13 sets forth the amino acid sequence for the predicted fusion loop 2 region of the envelope glycoprotein B of strain VR1814 [Human beta-herpesvirus 5], based on GenBank Accession # ACZ79977.1.

SEQ ID NO: 14 sets forth the amino acid sequence for the furin-like cleavage site of the envelope glycoprotein B of strain VR1814 [Human beta-herpesvirus 5], based on GenBank Accession # ACZ79977.1.

SEQ ID NO: 15: sets forth the amino acid sequence for the protease cleavage site of the envelope glycoprotein B of strain VR1814 [Human beta-herpesvirus 5], based on GenBank Accession # ACZ79977.1.

DETAILED DESCRIPTION

The inventors surprisingly discovered mutations that can be introduced into a cytomegalovirus (CMV) gB polypeptide, which can, among other things, greatly facilitate the production and subsequent purification of a stable gB antigen; significantly improve the efficiency of production of a gB polypeptide; maintain and/or increase antigenicity of a gB polypeptide, as compared to the wild-type gB polypeptide; facilitate a focused immune response to gB; and reduce and/or eliminate steric occlusion of neutralizing epitopes of gB. The modified gB polypeptide also surprisingly demonstrated strong structural integrity and a potential to undergo structural conformational changes in tertiary structure in response to significant pH changes. The structural changes were strictly pH-dependent. Without being bound by theory, the potential to undergo structural conformational changes in response to significant pH changes may be a newly recognized property of the HCMV gB ectodomain.

gB is an envelope glycoprotein B having numerous roles, one of which is the involvement in the fusion of the cytomegalovirus with host cells. It is encoded by the UL55 gene of HCMV genome.

In one aspect, the invention relates to a modified HCMV gB that is based on the VR1814 gB sequence (GenBank # ACZ79977.1, SEQ ID NO: 6). However, the present invention is applicable to gB proteins originating from any CMV strain. Unless otherwise stated, references to the numbering of amino acid residue positions of a CMV gB polypeptide as used herein are in relation to the amino acid sequence of the gB protein of SEQ ID NO: 6, from the clinical isolate VR1814 strain. Comparable amino acid positions in a gB protein of any other CMV strains can be determined by those of ordinary skill in the art. Accordingly, the term "CMV gB protein" or "HCMV gB protein" as used herein is to be understood as a HCMV gB protein from any human HCMV strain (not limited to the VR1814 strain). The actual residue position number may need to be adjusted for gB proteins from other human CMV strains depending on the actual sequence alignment.

In one embodiment, the modified HCMV gB polypeptide includes amino acids 1-705 of SEQ ID NO: 6. In another embodiment, the modified HCMV gB polypeptide includes at least one mutation in the fusion loop 1 region of an HCMV gB polypeptide. The precise boundaries of the fusion loop 1 region of a wild-type VR1814 gB polypeptide are currently not fully defined, however, the predicted sequence of the fusion loop 1 region of a wild-type VR1814 gB polypeptide is $Y^{153}AYIHT^{158}$ (SEQ ID NO: 12).

In another embodiment, the modified HCMV gB polypeptide includes at least one mutation in the fusion loop 2 region of an HCMV gB polypeptide. The precise boundaries of the fusion loop 2 region of a wild-type VR1814 gB polypeptide are currently not fully defined, however, the predicted sequence of the fusion loop 2 region of a wild-type VR1814 gB polypeptide is $G^{237}STWLYRE^{244}$ (SEQ ID NO: 13).

In a preferred embodiment, the modified HCMV gB polypeptide includes at least one mutation in the fusion loop 1 region and in the fusion loop 2 region of an HCMV gB polypeptide. In another preferred embodiment, the modified HCMV gB polypeptide includes a total of at most four mutations in the fusion loop 1 region and in the fusion loop 2 region of an HCMV gB polypeptide.

In another embodiment, the modified HCMV gB polypeptide includes at least one mutation in the furin-like cleavage site of an HCMV gB polypeptide. In a preferred embodiment, the modified HCMV gB polypeptide includes at most two mutations in the furin-like cleavage site of an HCMV gB polypeptide.

In another preferred embodiment, the modified HCMV gB polypeptide includes at least one mutation in the fusion loop 1 region, at least one mutation in the fusion loop 2 region, and at least one mutation in the furin-like cleavage site of an HCMV gB polypeptide. The sequence of the furin-like cleavage site of a wild-type VR1814 gB polypeptide is $R^{456}TKR^{459}$ (SEQ ID NO: 14).

In another preferred embodiment, the modified HCMV gB polypeptide includes at least two mutations in the fusion loop 1 region, at least one mutation in the fusion loop 2 region, and at least one mutation in the furin-like cleavage site of an HCMV gB polypeptide.

In one aspect, the invention relates to a CMV gB polypeptide or immunogenic fragment thereof having a mutation at position Y155, as compared to SEQ ID NO: 6.

In one aspect, the invention relates to a CMV gB polypeptide or immunogenic fragment thereof having a mutation at positions Y155 and I156, as compared to SEQ ID NO: 6.

In one aspect, the invention relates to a CMV gB polypeptide or immunogenic fragment thereof having a mutation at positions Y155, I156, and H157, as compared to SEQ ID NO: 6.

In one aspect, the invention relates to a CMV gB polypeptide or immunogenic fragment thereof having a mutation at positions I156 and H157, as compared to SEQ ID NO: 6.

In one aspect, the invention relates to a CMV gB polypeptide or immunogenic fragment thereof having a mutation at positions Y155, I156, H157, and W240, as compared to SEQ ID NO: 6.

In one aspect, the invention relates to a CMV gB polypeptide or immunogenic fragment thereof having a mutation at positions Y155 and W240, as compared to SEQ ID NO: 6.

In one aspect, the invention relates to a CMV gB polypeptide or immunogenic fragment thereof having a mutation at positions Y155, H157, and W240, as compared to SEQ ID NO: 6.

In one aspect, the invention relates to a CMV gB polypeptide or immunogenic fragment thereof having a mutation at positions Y155 and H157, as compared to SEQ ID NO: 6.

In one aspect, the invention relates to a CMV gB polypeptide or immunogenic fragment thereof having the mutation Y155G, as compared to SEQ ID NO: 6.

In one aspect, the invention relates to a CMV gB polypeptide or immunogenic fragment thereof having the mutations Y155G and I156H, as compared to SEQ ID NO: 6.

In one aspect, the invention relates to a CMV gB polypeptide or immunogenic fragment thereof having the mutations Y155G, I156H, and H157R, as compared to SEQ ID NO: 6.

In one aspect, the invention relates to a CMV gB polypeptide or immunogenic fragment thereof having the mutations I156H and H157R, as compared to SEQ ID NO: 6.

In one aspect, the invention relates to a CMV gB polypeptide or immunogenic fragment thereof having the mutations Y155G, I156H, H157R, and W240A, as compared to SEQ ID NO: 6.

In one aspect, the invention relates to a CMV gB polypeptide or immunogenic fragment thereof having the mutations Y155G and W240A, as compared to SEQ ID NO: 6.

In one aspect, the invention relates to a CMV gB polypeptide or immunogenic fragment thereof having the mutations Y155G, H157R, and W240A, as compared to SEQ ID NO: 6.

In one aspect, the invention relates to a CMV gB polypeptide or immunogenic fragment thereof having the mutations Y155G and H157R, as compared to SEQ ID NO: 6.

In one embodiment, the gB polypeptide does not include a mutation at any one of the following positions, individually or in combination: (i) R236, (ii) G237, (iii) T158; (iv) Y242.

For example, in one embodiment, the gB polypeptide does not include any one of the following mutations, individually or in combination: (i) R236N, (ii) G237N, (iii) T158N; (iv) Y242T, (v) Y242S; (vi) Y242C.

Exemplary Modified Human CMV gB Polypeptides

In one aspect, the invention relates to a polypeptide having the amino acid sequence that is at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% identical to SEQ ID NO: 1.

In one embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 1, includes the amino acid sequence $VVDPLPP^{705}$ (SEQ ID NO: 9) as a part of the polypeptide sequence.

Without being bound by theory, the sequence set forth in SEQ ID NO: 9 may be highly hydrophobic and structurally stiff, which facilitates immunogenicity of the polypeptide. Accordingly, in one embodiment, the sequence set forth in SEQ ID NO: 9 is hydrophobic.

In another embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 1, includes the amino acid sequence $RA^{457}TKA^{459}S$ (SEQ ID NO: 10) as a part of the polypeptide sequence.

Without being bound by theory, the sequence set forth in SEQ ID NO: 10 may prevent cleavage of the gB polypeptide by cellular proteases. Preferably, the polypeptide of the invention does not include a protease cleavage site. For example, in one embodiment, the polypeptide does not include a wild-type, natural CMV protease cleavage site, e.g., $RTKR^{459}$ (SEQ ID NO: 15) for the envelope glycoprotein B of strain VR1814 [Human beta-herpesvirus 5], based on GenBank Accession # ACZ79977.1. In another embodiment, the polypeptide does not include a non-naturally occurring protease cleavage site. In yet another embodiment, the polypeptide does not include a non-naturally occurring protease cleavage site that replaces the wild-type, natural CMV protease cleavage site. In one embodiment, the polypeptide does not include a protease cleavage site at or encompassing residue $R^{459}$ at position 459 of a human CMV gB, according to the numbering of SEQ ID NO: 6, wherein the protease cleavage site includes at most 20, 19, 18, 17, 16, 15, 14, 13, 12, 11, 10, 9, 8, 7, 6, 5, 4, or 3 amino acid residues in length. For example, the polypeptide does not include a protease cleavage site encompassing residue $R^{459}$ at position 459 of a human CMV gB, according to the numbering of SEQ ID NO: 6, wherein the protease cleavage site includes at most 6, more preferably at most 5, and most preferably at most 4 amino acid residues in length.

In another embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 1, includes both the amino acid sequence VVDPLPP$^{705}$ (SEQ ID NO: 9) and the amino acid sequence RA$^{457}$TKA$^{459}$S (SEQ ID NO: 10) as a part of the polypeptide sequence.

In one aspect, the invention relates to a polypeptide having the amino acid sequence that is at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% identical to SEQ ID NO: 2.

In one embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 2, includes the amino acid sequence VVDPLPP$^{705}$ (SEQ ID NO: 9) as a part of the polypeptide sequence.

In another embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 2, includes the amino acid sequence RA$^{457}$TKA$^{459}$S (SEQ ID NO: 10) as a part of the polypeptide sequence.

Preferably, the polypeptide does not include a protease cleavage site. For example, in one embodiment, the polypeptide does not include a wild-type, natural CMV protease cleavage site, e.g., RTKR$^{459}$ (SEQ ID NO: 15) for the envelope glycoprotein B of strain VR1814 [Human betaherpesvirus 5], based on GenBank Accession # ACZ79977.1. In another embodiment, the polypeptide does not include a non-naturally occurring protease cleavage site. In yet another embodiment, the polypeptide does not include a non-naturally occurring protease cleavage site that replaces the wild-type, natural CMV protease cleavage site.

In another embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 2, includes both the amino acid sequence VVDPLPP$^{705}$ (SEQ ID NO: 9) and the amino acid sequence RA$^{457}$TKA$^{459}$S (SEQ ID NO: 10) as a part of the polypeptide sequence.

In one aspect, the invention relates to a polypeptide having the amino acid sequence that is at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% identical to SEQ ID NO: 3.

In one embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 3, includes the amino acid sequence VVDPLPP$^{705}$ (SEQ ID NO: 9) as a part of the polypeptide sequence.

In another embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 3, includes the amino acid sequence RA$^{457}$TKA$^{459}$S (SEQ ID NO: 10) as a part of the polypeptide sequence.

Preferably, the polypeptide does not include a protease cleavage site. For example, in one embodiment, the polypeptide does not include a wild-type, natural CMV protease cleavage site, e.g., RTKR$^{459}$ (SEQ ID NO: 15) for the envelope glycoprotein B of strain VR1814 [Human betaherpesvirus 5], based on GenBank Accession # ACZ79977.1. In another embodiment, the polypeptide does not include a non-naturally occurring protease cleavage site. In yet another embodiment, the polypeptide does not include a non-naturally occurring protease cleavage site that replaces the wild-type, natural CMV protease cleavage site.

In another embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 3, includes both the amino acid sequence VVDPLPP$^{705}$ (SEQ ID NO: 9) and the amino acid sequence RA$^{457}$TKA$^{459}$S (SEQ ID NO: 10) as a part of the polypeptide sequence.

In one aspect, the invention relates to a polypeptide having the amino acid sequence that is at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% identical to SEQ ID NO: 5.

In one embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 5, includes the amino acid sequence VVDPLPP$^{705}$ (SEQ ID NO: 9) as a part of the polypeptide sequence.

In another embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 5, includes the amino acid sequence RA$^{457}$TKA$^{459}$S (SEQ ID NO: 10) as a part of the polypeptide sequence.

Preferably, the polypeptide does not include a protease cleavage site. For example, in one embodiment, the polypeptide does not include a wild-type, natural CMV protease cleavage site, e.g., RTKR$^{459}$ (SEQ ID NO: 15) for the envelope glycoprotein B of strain VR1814 [Human betaherpesvirus 5], based on GenBank Accession # ACZ79977.1. In another embodiment, the polypeptide does not include a non-naturally occurring protease cleavage site. In yet another embodiment, the polypeptide does not include a non-naturally occurring protease cleavage site that replaces the wild-type, natural CMV protease cleavage site.

In another embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 5, includes both the amino acid sequence VVDPLPP$^{705}$ (SEQ ID NO: 9) and the amino acid sequence RA$^{457}$TKA$^{459}$S (SEQ ID NO: 10) as a part of the polypeptide sequence.

Exemplary Modified Rhesus CMV gB Polypeptides

In one aspect, the invention relates to a polypeptide having the amino acid sequence that is at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% identical to SEQ ID NO: 7.

In one embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 7, includes the amino acid sequence WDPLPP (SEQ ID NO: 9) as a part of the polypeptide sequence.

In another embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 7, includes the amino acid sequence RATKAS (SEQ ID NO: 10) as a part of the polypeptide sequence. See, for example, residues 428-433 of SEQ ID NO: 7.

Preferably, the polypeptide does not include a protease cleavage site. For example, in one embodiment, the polypeptide does not include a wild-type, natural CMV protease cleavage site. In another embodiment, the polypeptide does not include a non-naturally occurring protease cleavage site. In yet another embodiment, the polypeptide does not include a non-naturally occurring protease cleavage site that replaces the wild-type, natural CMV protease cleavage site.

In another embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 7, includes both the amino acid sequence VVDPLPP (SEQ ID NO: 9) and the amino acid sequence RATKAS (SEQ ID NO: 10) as a part of the polypeptide sequence.

In one aspect, the invention relates to a polypeptide having the amino acid sequence that is at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% identical to SEQ ID NO: 8.

In one embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 8, includes the amino acid sequence VVDPLPP (SEQ ID NO: 9) as a part of the polypeptide sequence.

In another embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 8, includes the amino acid sequence RATKAS (SEQ ID NO: 10) as a part of the polypeptide sequence.

Preferably, the polypeptide does not include a protease cleavage site. For example, in one embodiment, the polypeptide does not include a wild-type, natural CMV protease cleavage site. In another embodiment, the polypeptide does not include a non-naturally occurring protease cleavage site. In yet another embodiment, the polypeptide does not include a non-naturally occurring protease cleavage site that replaces the wild-type, natural CMV protease cleavage site.

In another embodiment, the polypeptide having at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% sequence identity to SEQ ID NO: 8, includes both the amino acid sequence VVDPLPP (SEQ ID NO: 9) and the amino acid sequence RATKAS (SEQ ID NO: 10) as a part of the polypeptide sequence.

Glycosylation

Although CMV gB may be referred to as a glycoprotein, this nomenclature should not be taken to mean that the polypeptides described herein must be glycosylated when used with the invention. In some embodiments of the invention, the modified gB polypeptide is not glycosylated.

In one preferred embodiment, the gB polypeptide does not include a glycosylation site in the fusion loop regions of the gB polypeptide. That is, the gB polypeptide does not include a glycan moiety attached to the gB polypeptide within the fusion loop 1 region or within the fusion loop 2 region. The fusion loop 1 region of the VR1814 (SEQ ID NO: 6) is located at residues 153-158. The fusion loop 2 region of the VR1814 (SEQ ID NO: 6) is located at residues 237-244.

In one preferred embodiment, the gB polypeptide does not include a modified amino acid sequence that introduces an N-linked glycosylation site. For example, the modified gB polypeptide does not include an N-glycosylation site comprising N-X-S/T/C motif, wherein X is any amino acid residue.

In another preferred embodiment, the modified gB polypeptide does not include a modified amino acid sequence that introduces an O-linked glycosylation site. For example, the modified gB polypeptide does not include a carbohydrate moiety linked to the hydroxyl oxygen of serine and threonine. As another example, the modified gB polypeptide does not include an O-linked glycosylation at tyrosine, 5-hydroxylysine, or 4-hydroxyproline.

Unmodified Hydrophobic Surface Residues

In one preferred embodiment, the modified gB polypeptide does not include a deletion or substitution of any one of the amino acid residues selected from the group consisting of 154, 158, 159, 160, 230, 231, 232, 233, 234, 235, 236, 237, 238, 239, 241, and 242, according to the numbering of SEQ ID NO: 6, or any combination thereof. For example, the gB polypeptide does not include a mutation of any one of the amino acid residues selected from the group consisting of Y160, R236, S238, T239, and Y242, according to the numbering of SEQ ID NO: 6, or any combination thereof.

Deletion of C-Terminal Cytoplasmic Domain

The inventors further discovered that eliminating the cytoplasmic tail of HCMV gB may help to focus the mammal's immune response to the ectodomains of gB. Additionally, deletion of the cytoplasmic tail may reduce steric occlusion and facilitate access of antibodies to important neutralizing epitopes on gB.

Accordingly, in one embodiment, the native C-terminal cytoplasmic domain of the gB polypeptide (e.g., 100% of the amino acids of the cytoplasmic domain) is deleted. For example, the native C-terminal cytoplasmic domain is not deleted to a varying extent. That is, no less than 100% of the native C-terminal cytoplasmic domain is deleted. As used herein, the cytoplasmic tail of HCMV gB refers the amino acid sequence located at positions 771-905 of SEQ ID NO: 6.

Expression of gB

In one aspect, the invention relates to nucleic acids that encode a gB polypeptide of the invention. Preferably, the recombinant nucleic acid molecule: (a) is not a self-replicating RNA molecule; (b) is not an alphavirus replicon; (c) does not encode any alphavirus nonstructural proteins, such as NSP1, NSP2, NSP3 and NSP4; (d) does not contain: an Internal Ribosomal Entry Site (IRES), such as EIV1CV or EV71; and/or (e) does not contain a viral 2A site, such as FMDV.

In one embodiment, the invention relates to a nucleic acid sequence that encodes an amino acid sequence that is at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% identical to SEQ ID NO: 1.

In one embodiment, the invention relates to a nucleic acid sequence that encodes an amino acid sequence that is at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% identical to SEQ ID NO: 2.

In one embodiment, the invention relates to a nucleic acid sequence that encodes an amino acid sequence that is at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% identical to SEQ ID NO: 3.

In one embodiment, the invention relates to a nucleic acid sequence that encodes an amino acid sequence that is at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% identical to SEQ ID NO: 5.

In one embodiment, the invention relates to a nucleic acid sequence that encodes an amino acid sequence that is at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% identical to SEQ ID NO: 7.

In one embodiment, the invention relates to a nucleic acid sequence that encodes an amino acid sequence that is at least about 60%, 65%, 70%, 75%, 80%, 81%, 82%, 83%, 84%. 85%, 86%, 87%, 88%, 89%, 90%, 91%, 92%, 93%, 94%, 95%, 96%, 97%, 98%, 99%, or 100% identical to SEQ ID NO: 8.

The invention also provides a host cell comprising the nucleic acids described herein. When the host cell is cultured under a suitable condition, the nucleic acids can express a gB polypeptide. Preferably, said gB polypeptide forms a monodispersed trimer. For example, the gB polypeptide of the invention does not form a dimeric association of two trimers. In another exemplary embodiment, the gB polypeptide of the invention does not form a higher order association of trimers. Preferably, the monodispersed trimer can be secreted from the host cell.

Most preferably, the host cells are mammalian cells (e.g., human, non-human primate, horse, cow, sheep, dog, cat, and rodent (e.g., hamster). Suitable mammalian cells include, for example, Chinese hamster ovary (CHO) cells, human embryonic kidney cells (HEK-293 cells, typically transformed by sheared adenovirus type 5 DNA), NIH-3T3 cells, 293-T cells, Vera cells, HeLa cells, PERC.6 cells (ECACC deposit number 96022940), Hep G2 cells, MRC-5 (ATCC CCL-171), WI-38 (ATCC CCL-75), fetal rhesus lung cells (ATCC CL-160), Madin-Darby bovine kidney ("MDBK") cells, Madin-Darby canine kidney ("MDCK") cells (e.g., MDCK (NBL2), ATCC CCL34; or MDCK 33016, DSM ACC 2219), baby hamster kidney (BHK) cells, such as BHK21-F, HKCC cells, and the like.

In a most preferred embodiment, the host cell is EXP1293F™ (ThermoFisher Scientific) human cells, derived from the 293 cell line.

In certain embodiments, the host cell is a CHO cell. In certain embodiments, the polynucleotide encoding the gB polypeptide described herein is stably integrated into the genome of the CHO cell.

Various CHO cell lines are also available from European Collection of Cell Cultures (ECACC), or American Type Culture Collection (ATCC), such as CHO cell lines hCBE1 1 (ATCC® PTA-3357™), E77.4 (ATCC® PTA-3765™), hLT-B: R-hG1 CHO #14 (ATCC® CRL-1 1965™), MOR-CHO-MORAb-003-RCB (ATCC® PTA-7552™), AQ.C2 clone 1 1 B (ATCC® PTA-3274™), AQ.C2 clone 1 1 B (ATCC® PTA-3274™), hsAQC2 in CHO-DG44 (ATCC® PTA-3356™), xrs5 (ATCC® CRL-2348™), CHO-K1 (ATCC® CCL-61™), Led [originally named Pro-5WgaRI3C] (ATCC® CRL-1735™), Pro-5 (ATCC® CRL-1781™), ACY1-E (ATCC® 65421™) ACY1-E (ATCC® 65420™), pgsE-606 (ATCC® CRL-2246™), CHO-CD36 (ATCC® CRL-2092™), pgsC-605 (ATCC® CRL-2245™), MC2/3 (ATCC® CRL-2143™) CHO-ICAM-1 (ATCC® CRL-2093™), and pgsB-618 (ATCC® CRL-2241™). Any one of these CHO cell lines may be used.

Other commercially available CHO cell lines include, e.g., FREESTYLE™ CHO-S Cells and Flp-In™-CHO Cell Line from Life Technologies.

Alternative suitable host cells may also include, for example, insect cells (e.g., *Aedes aegypti, Autographa californica, Bombyx mori, Drosophila melanogaster, Spodoptera frugiperda*, and *Trichoplusia ni*), mammalian cells (e.g., human, non-human primate, horse, cow, sheep, dog, cat, and rodent (e.g., hamster)), avian cells (e.g., chicken, duck, and geese), bacteria (e.g., *E. coli, Bacillus subtilis*, and *Streptococcus* spp.), yeast cells (e.g., *Saccharomyces cerevisiae, Candida albicans, Candida maltose, Hansenual polymorpha, Kluyveromyces fragilis, Kluyveromyces lactis, Pichia guillerimondii, Pichia pastoris, Schizosaccharomyces pombe* and *Yarrowia lipolytica*), Tetrahymena cells (e.g., *Tetrahymena thermophila*) or combinations thereof.

Suitable insect cell expression systems, such as baculovirus systems, are known to those of skill in the art. Materials and methods for baculo virus/insect cell expression systems are commercially available. Suitable insect cells include, for example, Sf9 cells, Sf21 cells, Tn5 cells, Schneider S2 cells, and High Five cells (Invitrogen)).

In a most preferred embodiment, the host cell is a mammalian cell, not an insect cell. Accordingly in a preferred embodiment, the polypeptide does not have an insect cell pattern of glycosylation.

In certain embodiments, the recombinant nucleic acids are codon optimized for expression in a selected prokaryotic or eukaryotic host cell.

To facilitate replication and expression, the nucleic acids can be incorporated into a vector, such as a prokaryotic or a eukaryotic expression vector. Exemplary vectors include plasmids that are able to replicate autonomously or to be replicated in a host cell. Typical expression vectors contain suitable promoters, enhancers, and terminators that are useful for regulation of the expression of the coding sequence(s) in the expression construct. The vectors may also comprise selection markers to provide a phenotypic trait for selection of transformed host cells (such as conferring resistance to antibiotics such as ampicillin or neomycin).

Also provided herein is a process of producing cytomegalovirus (CMV) gB polypeptide comprising: (i) culturing the host cell described herein under a suitable condition, thereby expressing said gB polypeptide, or immunogenic fragment thereof; and (ii) harvesting said gB polypeptide, or immunogenic fragment thereof, from the culture.

In one embodiment, the gB polypeptide described herein is purified. The gB polypeptide can be purified using any suitable methods, such as HPLC, various types of chromatography (such as hydrophobic interaction, ion exchange, affinity, chelating, and size exclusion), electrophoresis, density gradient centrifugation, solvent extraction, or the like. As appropriate, the gB polypeptide may be further purified, as required, so as to remove substantially any polypeptides which are also secreted in the medium or result from lysis of host cells, so as to provide a product which is at least substantially free of host debris, e.g., polypeptides, lipids and polysaccharides.

As used herein, a "purified" protein or polypeptide is a protein or polypeptide which is recombinantly or synthetically produced, or produced by its natural host, and has been isolated from other components of the recombinant or synthetic production system or natural host such that the amount of the protein relative to other macromolecular components present in a composition is substantially higher than that present in a crude preparation. In general, a purified protein will be at least about 50% homogeneous and more preferably at least about 75%, at least about 80%, at least about 85%, at least about 90%, at least about 95% or substantially homogeneous.

In another embodiment, the process of purifying the modified gB polypeptide of the invention allows for production of the polypeptide at a purity of >85%, >86%, >87%, >88%, >89%, >90%, >91%, >92%, >93%, >94% or >95% of total protein by mass, as determined by gel electrophoresis. These high levels of purity make the modified gB polypeptide suitable for use as an immunogen in diagnostic applications or as an antigen in immunogenic compositions.

Preparation of Antibodies Against CMV Epitopes

The immunogenic polypeptides prepared as described above may be used to produce antibodies, both polyclonal and monoclonal. If polyclonal antibodies are desired, a selected mammal (e.g., mouse, rabbit, goat, guinea pig, horse, etc.) is immunized with an immunogenic polypeptide bearing a CMV epitope(s). Serum from the immunized animal is collected and treated according to known procedures. If serum containing polyclonal antibodies to a CMV epitope contains antibodies to other antigens, the polyclonal antibodies can be purified by immunoaffinity chromatography. Techniques for producing and processing polyclonal antisera are known in the art.

Monoclonal antibodies directed against CMV epitopes can also be readily produced by one skilled in the art. The general methodology for making monoclonal antibodies by hybridomas is known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against CMV epitopes can be screened for various properties; i.e., for isotype, epitope affinity, etc.

Antibodies, both monoclonal and polyclonal, which are directed against CMV epitopes are particularly useful in diagnosis, and those which are neutralizing are useful in passive immunotherapy. Monoclonal antibodies, in particular, may be used to raise anti-idiotype antibodies.

Immunoassay and Diagnostic Kits

Both the recombinant polypeptides which react immunologically with serum containing CMV antibodies, and the antibodies raised against these recombinant polypeptides, are useful in immunoassays to detect the presence of CMV antibodies, or the presence of the virus, in biological samples, including for example, blood or serum samples. Design of the immunoassays is subject to a great deal of variation, and a variety of these are known in the art. For example, the immunoassay may utilize the polypeptide having the sequence set forth in SEQ ID NO: 2. Alternatively, the immunoassay may use a combination of viral antigens derived from the gB polypeptides described herein. It may use, for example, a monoclonal antibody directed towards one modified gB polypeptides described herein, a combination of monoclonal antibodies directed towards the modified gB polypeptides described herein, monoclonal antibodies directed towards different viral antigens, polyclonal antibodies directed towards the modified gB polypeptides described herein, or polyclonal antibodies directed towards different viral antigens. Protocols may be based, for example, upon competition, or direct reaction, or may be sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the recombinant polypeptides of the invention containing CMV epitopes or antibodies directed against epitopes in suitable containers, along with the remaining reagents and materials required for the conduct of the assay, as well as a suitable set of assay instructions.

The polynucleotide probes can also be packaged into diagnostic kits. Diagnostic kits include the probe DNA, which may be labeled; alternatively, the probe DNA may be unlabeled and the ingredients for labeling may be included in the kit. The kit may also contain other suitably packaged reagents and materials needed for the particular hybridization protocol, for example, standards, as well as instructions for conducting the test.

Compositions and Methods of Treatment

The invention relates to compositions and methods of treatment using the cytomegalovirus gB polypeptide described herein, or a nucleic acid encoding such gB polypeptide described herein. For example, the polypeptide of the invention can be delivered directly as a component of an immunogenic composition. Alternatively, nucleic acids that encode the gB polypeptide of the invention can be administered to produce the CMV protein or immunogenic fragment in vivo. Certain preferred embodiments, such as protein formulations, recombinant nucleic acids (e.g., DNA, RNA, self-replicating RNA, or any variation thereof) and viral vectors (e.g., live, single-round, non-replicative assembled virions, or otherwise virus-like particles, or alphavirus VRP) that contain sequences encoding gB polypeptides are further described herein and may be included in the composition.

In one aspect, the invention provides an immunogenic composition comprising the recombinant CMV gB polypeptide described herein. The immunogenic composition can include additional CMV proteins, such as gO, gH, gL, pUL128, pUL130, pUL131, an immunogenic fragment thereof, or a combination thereof. For example, the gB polypeptide can be combined with CMV pentameric complex comprising: gH or a pentamer-forming fragment thereof, gL or a pentamer-forming fragment thereof, pUL128 or a pentamer-forming fragment thereof, pUL130 or a pentamer-forming fragment thereof, and pUL131 or a pentamer-forming fragment thereof. The gB polypeptide of the invention can also be combined with CMV trimeric complex comprising: gH or a trimer-forming fragment thereof, gL or a trimer-forming fragment thereof, and gO or a trimer-forming fragment thereof.

The immunogenic composition may include an adjuvant. Exemplary adjuvants to enhance effectiveness of the composition include: (1) aluminum salts (alum), such as aluminum hydroxide, aluminum phosphate, aluminum sulfate, etc.; (2) oil-in-water emulsion formulations (with or without other specific adjuvants such as muramyl peptides (see below) or bacterial cell wall components), such as for example (a) MF59 (PCT Publ. No. WO 90/14837), containing 5% Squalene, 0.5% TWEEN 80, and 0.5% Span 85 formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+ CWS (Detox™); (3) saponin adjuvants, such as QS-21, STIMULON™ (Cambridge Bioscience, Worcester, Mass.), which may be used or particles generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; and (6) other substances that act as adjuvants to enhance the effectiveness of the composition. In a preferred embodiment, the adjuvant is a saponin adjuvant, namely QS-21.

Each of the immunogenic compositions discussed herein may be used alone or in combination with one or more other antigens, the latter either from the same viral pathogen or from another pathogenic source or sources. These compositions may be used for prophylactic (to prevent infection) or therapeutic (to treat disease after infection) purposes.

In one embodiment, the composition may include a "pharmaceutically acceptable carrier," which includes any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as adjuvants. Furthermore, the antigen may be conjugated to a bacterial toxoid, such as a toxoid from diphtheria, tetanus, cholera, *H. pylori*, and etc. pathogens.

In one embodiment, the composition includes a diluent, such as water, saline, glycerol, ethanol, etc. Additionally, auxiliary substances, such as wetting or emulsifying agents, pH buffering substances, and the like, may be present in such vehicles.

The compositions described herein may include an immunologically effective amount of the polypeptide, as well as any other of the above-mentioned components, as needed. By "immunologically effective amount," it is meant that the administration of that amount to an individual, either in a single dose or as part of a series, is effective for eliciting an immune response. The immune response elicited may be sufficient, for example, for treatment and/or prevention and/or reduction in incidence of illness, infection or disease. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The composition may be administered parenterally, e.g., by injection, either so subcutaneously or intramuscularly. Additional formulations suitable for other modes of administration include oral and pulmonary formulations, suppositories, and transdermal applications. Oral formulations may be preferred for certain viral proteins. Dosage treatment may be a single dose schedule or a multiple dose schedule. The immunogenic composition may be administered in conjunction with other immunoregulatory agents.

In another aspect, the invention provides a method of eliciting an immune response against cytomegalovirus (CMV), comprising administering to a subject in need thereof an immunologically effective amount of a modified CMV gB polypeptide and/or an immunogenic composition described herein, which comprises the proteins, DNA molecules, RNA molecules (e.g., self-replicating RNA molecules), or VRPs as described above. In certain embodiments, the immune response comprises the production of neutralizing antibodies against CMV.

The immune response can comprise a humoral immune response, a cell-mediated immune response, or both. In some embodiments an immune response is induced against each delivered CMV protein. A cell-mediated immune response can comprise a Helper T-cell (Th) response, a CD8+ cytotoxic T-cell (CTL) response, or both. In some embodiments the immune response comprises a humoral immune response, and the antibodies are neutralizing antibodies.

Neutralizing antibodies block viral infection of cells. CMV infects epithelial cells and also fibroblast cells. In some embodiments the immune response reduces or prevents infection of both cell types. Neutralizing antibody responses can be complement-dependent or complement-independent. In some embodiments the neutralizing antibody response is complement-independent. In some embodiments the neutralizing antibody response is cross-neutralizing; i.e., an antibody generated against an administered composition neutralizes a CMV virus of a strain other than the strain used in the composition.

The modified CMV gB polypeptide and/or immunogenic composition described herein may also elicit an effective immune response to reduce the likelihood of a CMV infection of a non-infected mammal, or to reduce symptoms in an infected mammal, e.g., reduce the number of outbreaks, CMV shedding, and risk of spreading the virus to other mammals.

For example in one aspect, the modified CMV gB polypeptide and/or immunogenic composition described herein reduces viral shedding in a mammal. The term "viral shedding" is used herein according to its plain ordinary meaning in medicine and virology and refers to the production and release of virus from an infected cell. In some embodiments, the virus is released from a cell of a mammal. In some embodiments, virus is released into the environment from an infected mammal. In some embodiments the virus is released from a cell within a mammal.

In one aspect, the invention relates to a method for reducing CMV viral shedding in a mammal. The method includes administering the modified CMV gB polypeptide and/or immunogenic composition described herein to the mammal that is infected with or is at risk of a CMV infection. In one embodiment, the reduction in CMV viral shedding in a mammal is as compared to the viral shedding in mammals that were not administered the modified CMV gB. In another embodiment, the reduction in CMV viral shedding in a mammal is as compared to the viral shedding following an administration of a CMV pentamer alone or following an administration of a CMV pentamer in the absence of the modified CMV gB.

In one embodiment, the challenge cytomegalovirus strain is a human CMV strain. In one embodiment, the challenge cytomegalovirus strain is homologous to the CMV strain from which the modified CMV gB polypeptide is derived. In another embodiment, the challenge cytomegalovirus strain is homologous to the VR1814 CMV strain.

In one embodiment, the challenge cytomegalovirus strain is a human CMV strain that is heterologous to the CMV strain from which the modified CMV gB polypeptide is derived. In another embodiment, the challenge cytomegalovirus strain is a human CMV strain that is heterologous to the VR1814 CMV strain. In another embodiment, the challenge cytomegalovirus strain is the VR1814 CMV strain.

In another embodiment, the challenge cytomegalovirus strain is a rhesus CMV strain homologous to the macacine herpesvirus 3 isolate 21252 CMV strain. In another embodiment, the challenge cytomegalovirus strain is the macacine herpesvirus 3 isolate 21252 CMV strain.

A useful measure of antibody potency in the art is "50% neutralization titer." Another useful measure of antibody potency is any one of the following: a "60% neutralization titer"; a "70% neutralization titer"; a "80% neutralization titer"; and a "90% neutralization titer." To determine, for example, a 50% neutralizing titer, serum from immunized animals is diluted to assess how dilute serum can be yet retain the ability to block entry of 50% of infectious viruses into cells. For example, a titer of 700 means that serum retained the ability to neutralize 50% of infectious virus after being diluted 700-fold. Thus, higher titers indicate more potent neutralizing antibody responses. In some embodiments, this titer is in a range having a lower limit of about 200, about 400, about 600, about 800, about 1000, about 1500, about 2000, about 2500, about 3000, about 3500, about 4000, about 4500, about 5000, about 5500, about 6000, about 6500, or about 7000. The 50%, 60%, 70%, 80%, or 90% neutralization titer range can have an upper limit of about 400, about 600, about 800, about 1000, about 1500, about 2000, about 2500, about 3000, about 3500, about 4000, about 4500, about 5000, about 5500, about 6000, about 6500, about 7000, about 8000, about 9000, about 10000, about 1 1000, about 12000, about 13000, about 14000, about 15000, about 16000, about 17000, about 18000, about 19000, about 20000, about 21000, about 22000, about 23000, about 24000, about 25000, about 26000, about 27000, about 28000, about 29000, or about 30000. For example, the 50% neutralization titer can be about 3000 to about 6500. "About" means plus or minus 10% of the recited value. Neutralization titer can be measured as described in the specific examples, below.

An immune response can be stimulated by administering proteins, DNA molecules, RNA molecules (e.g., self-replicating RNA molecules), or VRPs to an individual, typically a mammal, including a human. In some embodiments the immune response induced is a protective immune response, i.e., the response reduces the risk or severity of or clinical consequences of a CMV infection. Stimulating a protective immune response is particularly desirable in some populations particularly at risk from CMV infection and disease. For example, at-risk populations include solid organ transplant (SOT) patients, bone marrow transplant patients, and hematopoietic stem cell transplant (HSCT) patients. VRPs can be administered to a transplant donor pre-transplant, or a transplant recipient pre- and/or post-transplant. Because vertical transmission from mother to child is a common source of infecting infants, administering VRPs to a woman who is pregnant or can become pregnant is particularly useful.

Any suitable route of administration can be used. For example, a composition can be administered intramuscularly, intraperitoneally, subcutaneously, or transdermally. Some embodiments will be administered through an intramucosal route such as intra-orally, intra-nasally, intra-vaginally, and intra-rectally. Compositions can be administered according to any suitable schedule.

Also provided herein is a method of inhibiting cytomegalovirus (CMV) entry into a cell, comprising contacting the cell with the immunogenic composition described herein.

The invention will be further described by reference to the following, non-limiting, examples.

EXAMPLES

The following Examples illustrate embodiments of the invention.

Example 1

Description of the gB705 Expression Construct

Pfizer's expression construct of HCMV gB705 (SEQ ID NO: 1) is based on the VR1814 gB sequence (GenBank # ACZ79977.1) that contains amino acids 1-705. A 6× His affinity tag is optionally included at the C-terminus in a pLH115 vector (Pfizer). Pfizer's gB705 contains four mutations ((Y155G/I156H/H157R/W240A) as well as mutations (R456A/R459A) in the furin-like cleavage site as illustrated in FIG. 1, wherein SS represents a signal sequence; D1 represents the Domain I, FL represents a fusion loop; 6h represents a 6× His tag. FIG. 2 shows the sequence of HCMV gB705 (SEQ ID NO: 2)

Example 2

Expression of gB705

Figure 3:
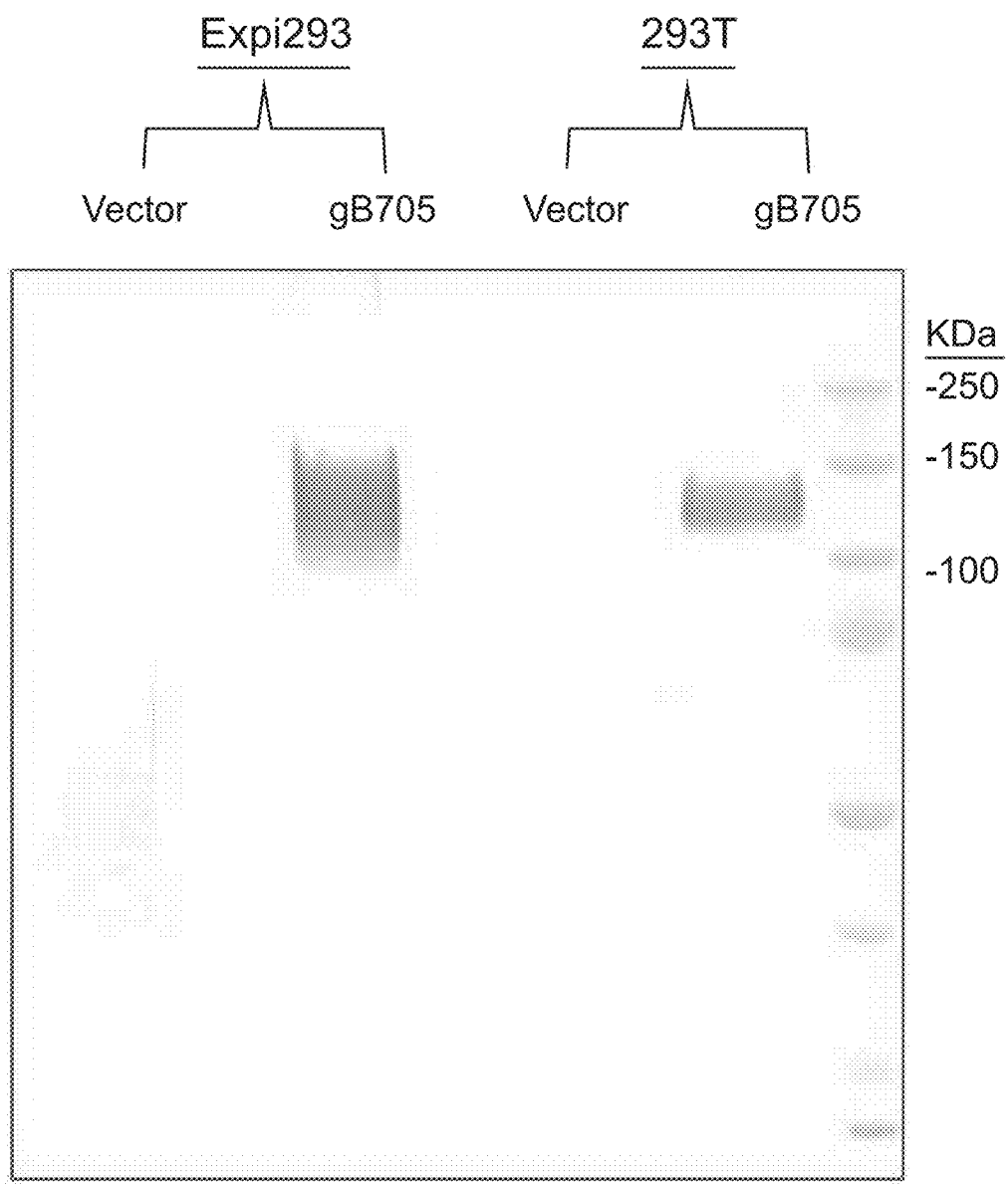
FIG. 3—The gB705 protein was transiently expressed in Expi293 and 293T cells after transfection respectively. The target protein was secreted into culture medium, precipitated by an affinity tag, and resolved on SDS-PAGE under reducing condition. The presence of the gB705 protein was visualized by a Western blot analysis using poly-clonal anti-gB serum. As shown, gB705 exhibited a single band with an apparent molecular weight about 130 kDa, consistent with the design of the furin-cleavage site being knocked out by mutations.

The initial assessment of gB705 expression was carried out by transfecting the construct DNA into HEK293T or Expi293F cells using Effectene Transfection Reagent (Qiagen) or Expifetamin 293 Transfection kit (Gibco), respectively. The culture supernatants were harvested ~48 hours after transfection. The gB705 protein was pulled down from the culture supernatant of transfected cells using a MAG-NEHIS™ Protein Purification System (Promega) and was analyzed on 4-12% Bis-Tris protein gel (NUPAGE® NOVEX®) under reducing condition. Presence of the target proteins was detected by Western blot using anti-HCMV polyclonal antibody (CytoGam). The result showed that recombinant gB705 existed as a single protein band with molecular weight about 120 kDa (FIG. 3). This apparent molecular weight is higher than that predicted from the peptide sequence of residues 25-705 [of SEQ ID NO: 1] from the mature gB705 polypeptide, indicating that the gB705 protein is heavily glycosylated. The gB705 protein is expressed efficiently as a homogeneous protein in transfection of HEK293 or Expi293F cells.

Example 3

Recombinant gB705 Contains Intact Neutralizing Epitopes Recognized by Human Anti-HCMV gB Monoclonal Antibodies (mAbs)

To evaluate the structural integrity of recombinant gB, a panel of five neutralizing human anti-HCMV gB mAbs were tested for the binding of gB705 (SEQ ID NO: 2). Briefly, the culture supernatants from gB705 transfected Expi293F cells were added on a pre-blocked HISGRAB™ Nickel Coated Plate (Pierce) and incubated for 1 hour at room temperature. After wash, serial diluted antibody solutions were added to the plate and incubated for 1 hour at room temperature, followed by addition of HRP-conjugated anti-human IgG secondary antibody. After 1 hour incubation, the plate was washed and the peroxidase substrate TMB was added to be read by a plate reader when the color was developed. The results showed all five human anti-gB mAbs bound efficiently to gB705 (FIG. 4A).

Recombinant gB705 binds to three anti-AD5 mAbs including 2611, 5F1 and 4H9 (each described in Table 1 of US patent publication no. 20160280770 and Table 1 of WIPO publication no. WO2010007533), whereas recombinant gB proteins from a commercial source (Sino gB, from Sino Biologicals, Inc.) did not (FIG. 4B). Similarly, these three mAbs did not bind to a recombinant gB protein expressed in insect cells from RedBiotech, Inc. (data not shown). The recombinant gB protein from the commercial source and from RedBiotec do not include any one of the following mutations: Y155G, I156H, H157R, and W240A, according to the numbering of SEQ ID NO: 6. Without being bound by theory, the inventive combination of mutations Y155G, I156H, H157R, and W240A include deletions of the cytoplasmic tail and mutations in hydrophobic fusion loops of gB. These mutations appear to relieve steric hindrance that potentially would have otherwise blocked antibody access to these sites in an unmodified gB protein or in a protein that does not include the inventive combination of mutations.

The 2B11 mAb has a sequence set forth in SEQ ID NO: 367 for the heavy chain and SEQ ID NO: 368 for the light chain; 5F1 mAb has a sequence set forth in SEQ ID NO: 290 for the heavy chain and SEQ ID NO: 291 for the light chain; and 4H9 mAb has a sequence set forth in SEQ ID NO: 308 for the heavy chain and SEQ ID NO: 309 for the light chain, as disclosed in US patent publication no. 20160280770 and WIPO publication no. WO2010007533, each sequence of which is incorporated by reference herein).

Figure 4A:
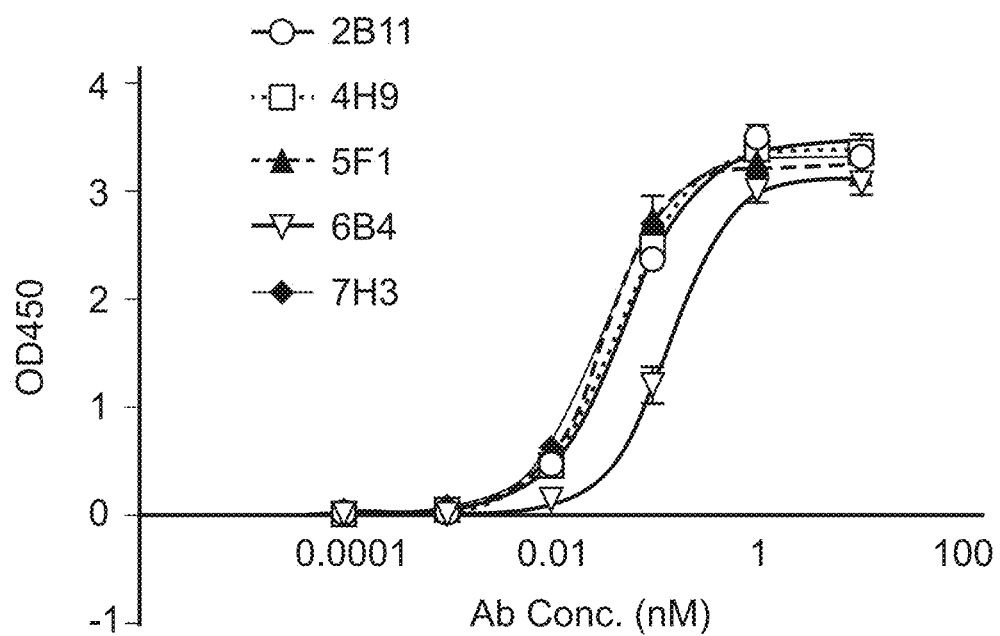
FIG. 4A-B—FIG. 4A Binding of human anti-HCMV gB monoclonal antibodies to gB705 protein.
Figure 4B:
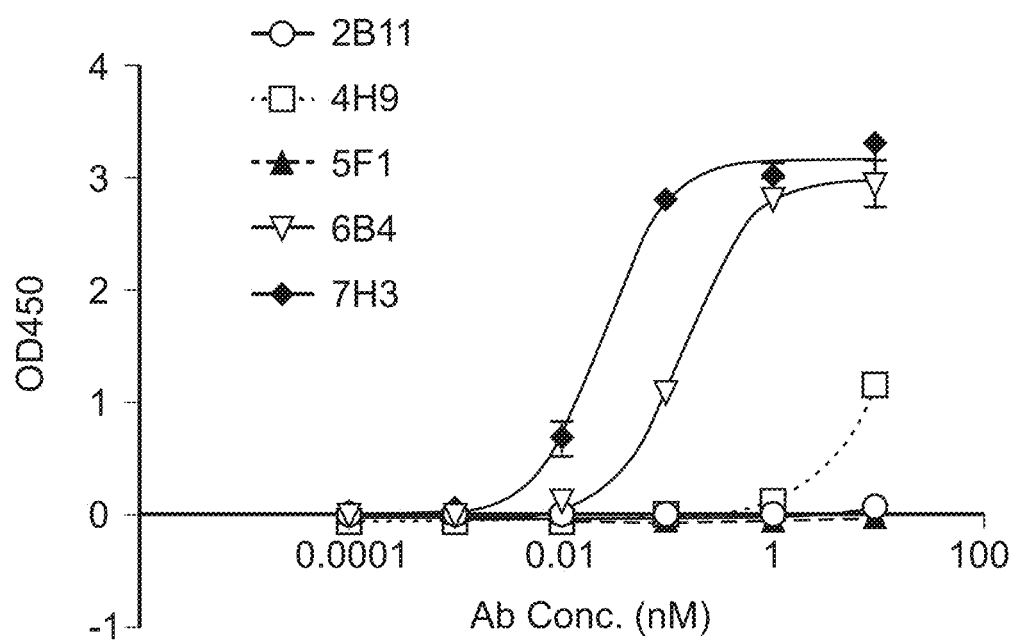

FIG. 4A Binding of human anti-HCMV gB monoclonal antibodies to gB705 protein. Culture supernatants from gB705 transfected Expi293F cells were captured on a pre-blocked HISGRAB™ Nickel Coated Plate (Pierce) and incubated serially diluted monoclonal antibodies followed by detection with HRP conjugated anti-human Ig secondary antibody (ELN #00710043-0177). FIG. 4B Binding of human anti-HCMV gB monoclonal antibodies to Sino gB protein (gB from Sino Biologicals, Inc.) (ELN #00710043-0177).

Example 4

Scale-Up Production and Purification of gB705

Figure 5:
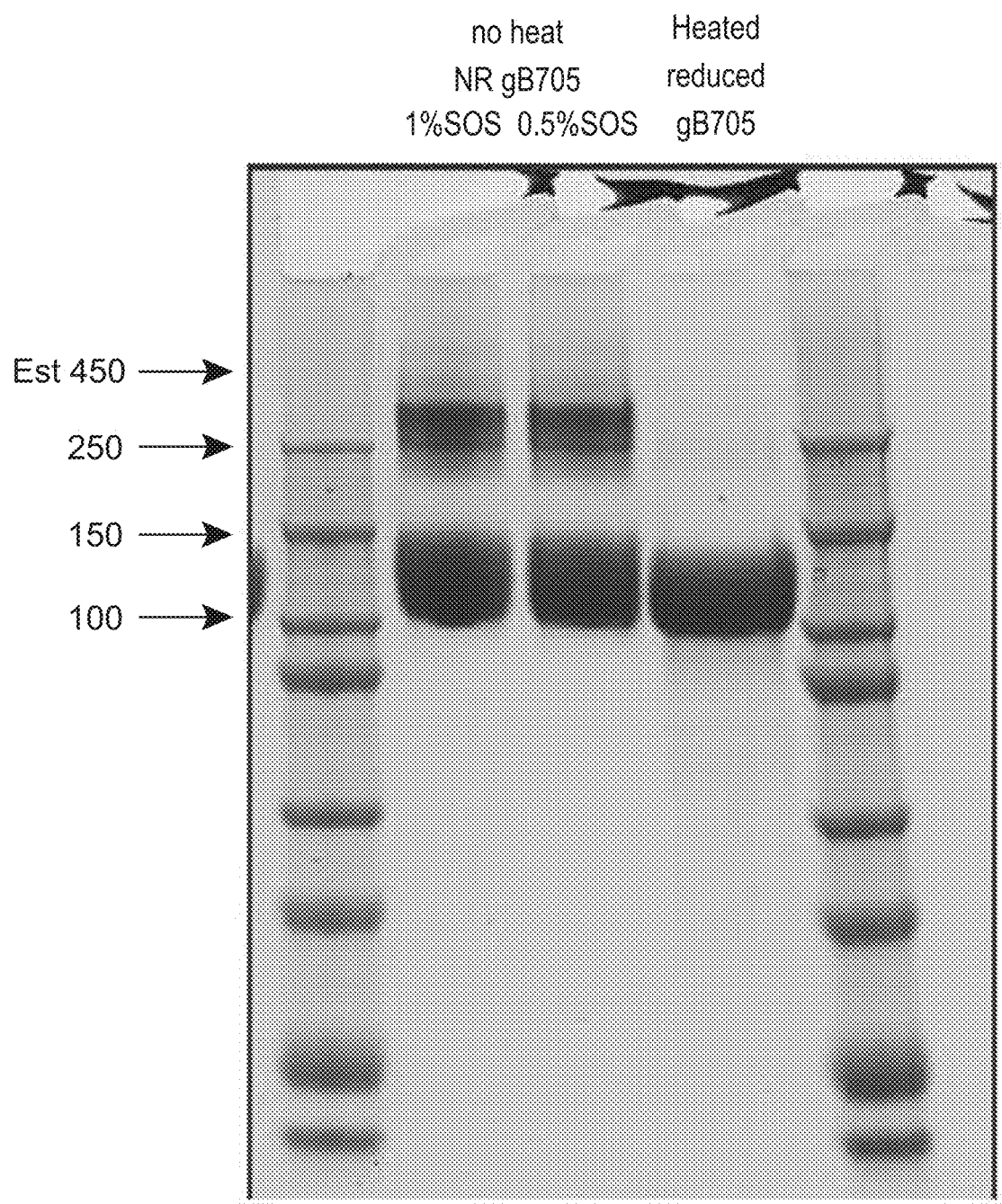
FIG. 5—HCMV gB705 protein (SEQ ID NO: 2) was analyzed on SDS-PAGE and exhibited a single band under a fully reduced condition and showed one additional high molecular weight band under partially reduced conditions, representing a trimer.

The gB705 construct was transiently transfected into 1.8 liters of Expi293F cells and about 95 mg of protein was purified from the conditioned media collected on day 4 through a series of processes of diafiltration, Ni-sepharose and size exclusion chromatography. The protein was analyzed on SDS-PAGE and exhibited a single band under reducing condition, as detected by Coomassie blue staining (FIG. 5). Under non-reducing conditions, there were higher molecular weight bands that may be corresponding to a trimeric form of the protein. FIG. 5 shows an SDS-PAGE of gB705 under reducing and non-reducing conditions (ELN #00709755-0086).

Example 5

Figure 6:
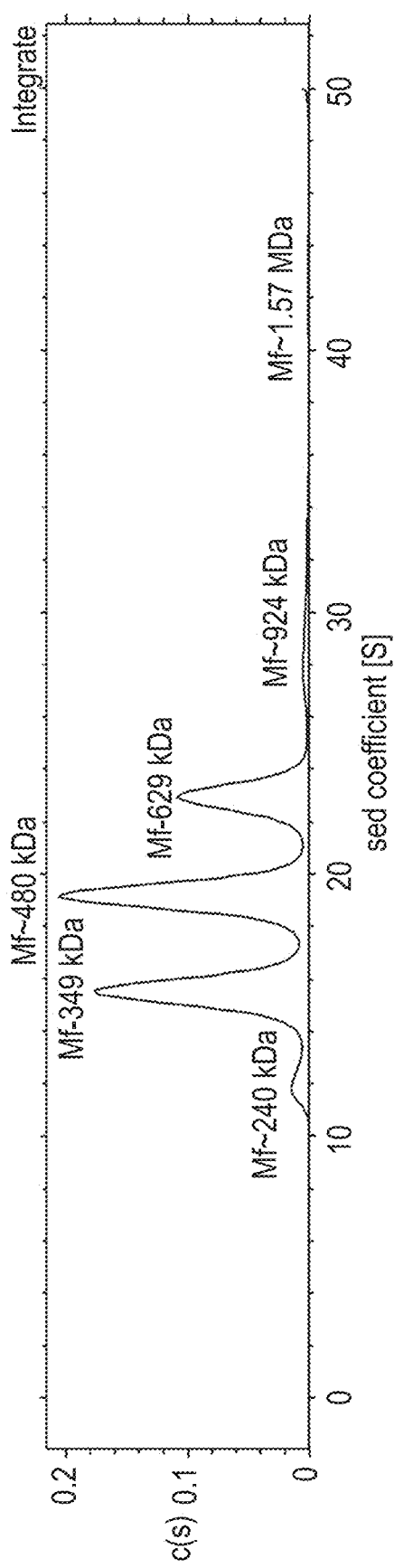
FIG. 6—Sedimentation Velocity analysis of gB705 (ELN #00708337-0110).
Figure 16:
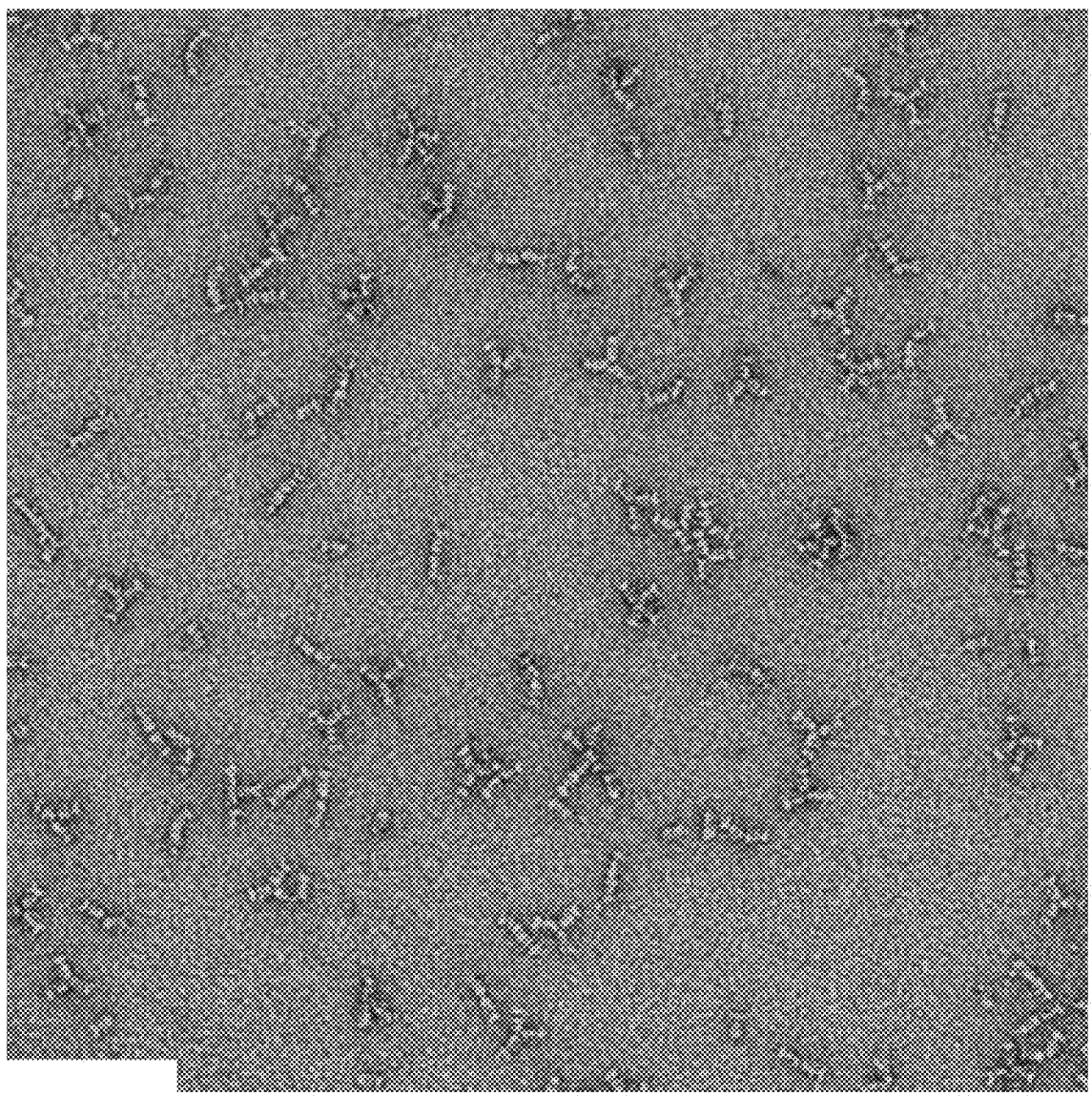
FIG. 16—TEM image of negative staining of gB705 (62000× magnification) (ELN #00702423-0124)

Structural Characterization of Recombinant gB705 Expressed in Expi293F Cells: Oligomer Formation and Stability Postfusion gB protein is in a trimer form. To characterize whether the gB705 forms higher order of oligomers, a series of experiments were carried out as summarized below.
Singular and Oligomeric Trimers of gB705 with Characteristics of Post-Fusion gB Observed by Transmission Electron Microscopy Recombinant gB705 protein was subjected to electron microscopy analysis after negative staining. The image (FIG. 16) shows that the protein forms a singular trimer as well as larger oligomeric complexes (that is, associations between trimers). The singular trimer of gB705 exhibited strong similarity in general morphology with the postfusion gB structure as published in Burke et al., *PLoS Pathog.* 2015 October; 11(10). In contrast to the singular trimer formed by the inventive gB705, a modified gB protein, termed "gB706," which does not include the inventive combination of fusion loop mutations, forms a dimer and trimer of trimers, as discussed in in Sharma et al., *Virology.* 2013 Jan. 20; 435(2):239-49, namely on page 243 and in FIG. 2C. More specifically, the gB706 protein of Sharma et al. is described as encoding the mature ectodomain of HCMV (strain AD169) gB, residues 25-706, with a signal sequence. Sharma et al. further describe gB706 as lacking the hydrophobic membrane-proximal region, the transmembrane region, and the cytoplasmic domain of gB.
Multiple Species of gB705 Observed in Velocity Analytical Ultracentrifugation Analysis The purified gB705 protein (SEQ ID NO: 2) was also subjected to velocity analytical ultracentrifugation analysis and the result showed that the protein formed multiple peaks corresponding to the sizes of singular trimer or larger/high-order complexes (FIG. 6). FIG. 6 velocity analytical ultracentrifugation analysis of gB705 (ELN #00708337-0110).
Transforming Recombinant gB705 to Homogeneous Singular Trimer by Treatment of Ethylenediaminetetraacetic Acid (EDTA)

Figure 7:
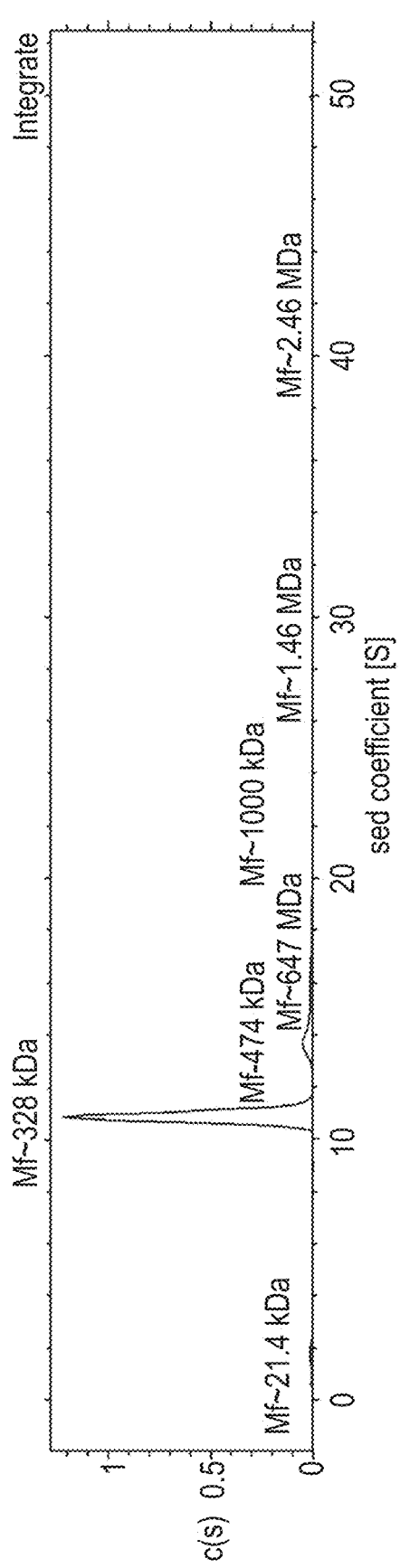
FIG. 7—Velocity sedimentation analysis of 10 mM EDTA-treated gB705 (ELN #00708337-0110).

To assess the stability of the gB705 higher order oligomers, the gB705 protein was subjected to various treatment including surfactants, chaotropes, heat, reductant and EDTA (data not shown). Among these conditions, it was observed that EDTA can break down the high molecular weight oligomers to homogenous monodispersed trimers. This was confirmed by velocity sedimentation analysis as shown in FIG. 7. This homogenous material establishes a strong base entity for studying its structural characteristics and its potential for change under biologically relevant conditions. FIG. 7 shows Velocity sedimentation analysis of 10 mM EDTA-treated gB705 (ELN #00708337-0110).

In the structure of a postfusion HCMV gB protein, a calcium ion (Ca++) was observed in the core of the central coiled coil, coordinated by residue D508. To evaluate whether Ca++ ion has an effect on the overall shape of the gB705 after EDTA treatment, sedimentation velocity analysis was performed on the EDTA-treated gB705 at pH 5.2 with and without adding back 10 mM Ca++ ion. The result showed that adding back Ca++ ion had no impact on hydrodynamic properties of gB705 at pH 5.2 (data not shown). Furthermore, adding back Ca++ ion did not cause the protein to form high molecular weight oligomers seen in the non-EDTA-treated gB705 protein. In contrast, adding back Ni+ or Cu++ ions led to formation of high-order oligomeric complexes of gB705 trimer (data not shown). Taken together, oligomer formation of gB705 trimer may be a result of the existence of the 6× His affinity tag, rather than due to some unknown intrinsic properties of gB705 trimer.

Example 6

Structural Characterization of gB705 Trimer at Different pH Conditions

Figure 8A:
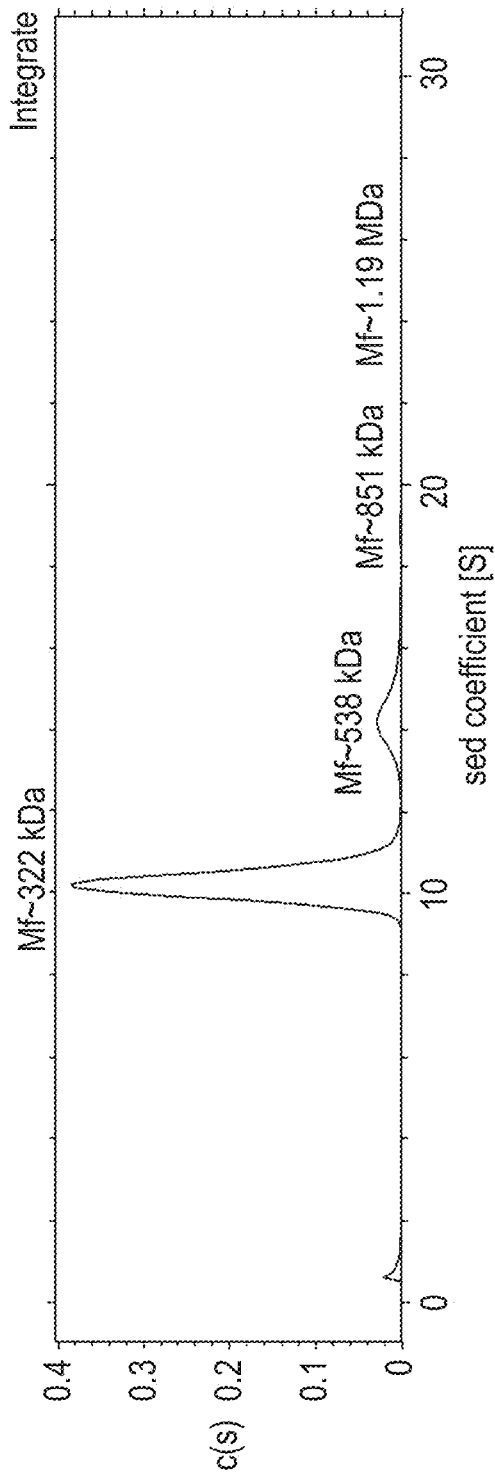
Figure 8B:
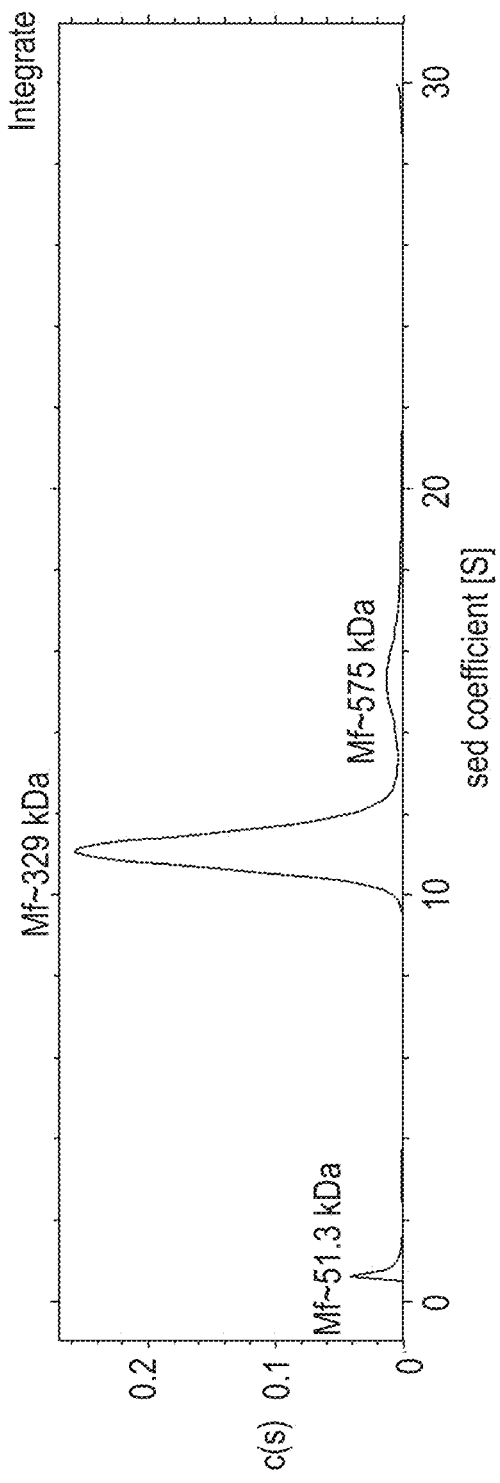
Figure 9A:
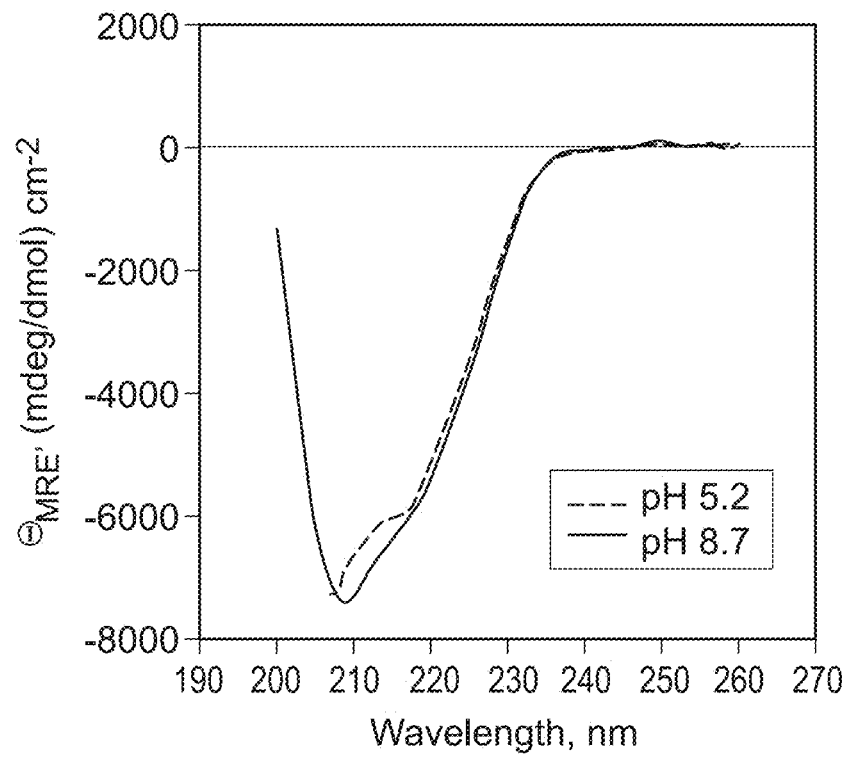
FIG. 9A-B—FIG. 9A Far UV CD analysis.
Figure 9B:
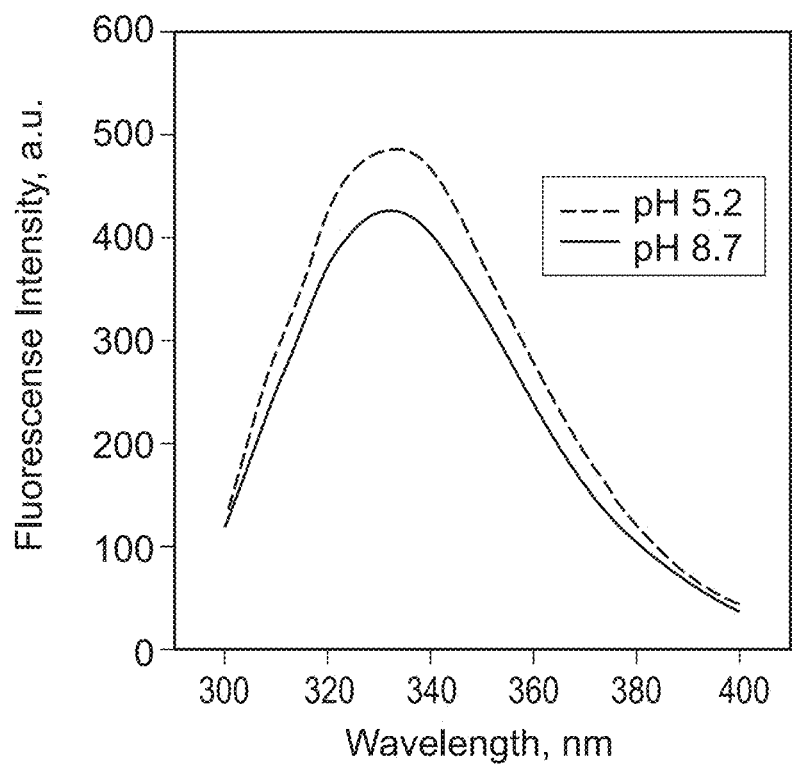
Figure 10:
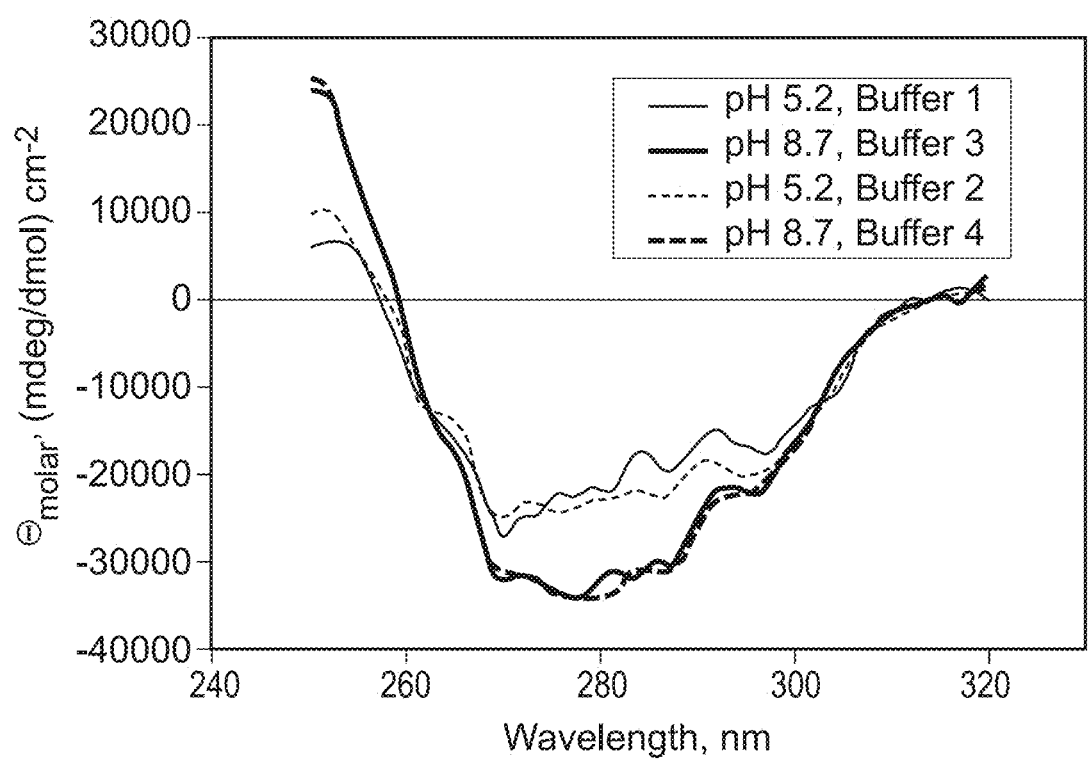
FIG. 10—Near UV CD spectroscopy analysis of gB705 at pH 5.2 and pH 8.7. Buffer 1, 50 mM citrate, 100 mM phosphate; Buffer 2, 50 mM NaOAc; Buffer 3, 100 mM Na carbonate/bicarbonate; Buffer 4, 50 mM Na borate (ELN #00708337-0115, 0117).
Figure 11A:
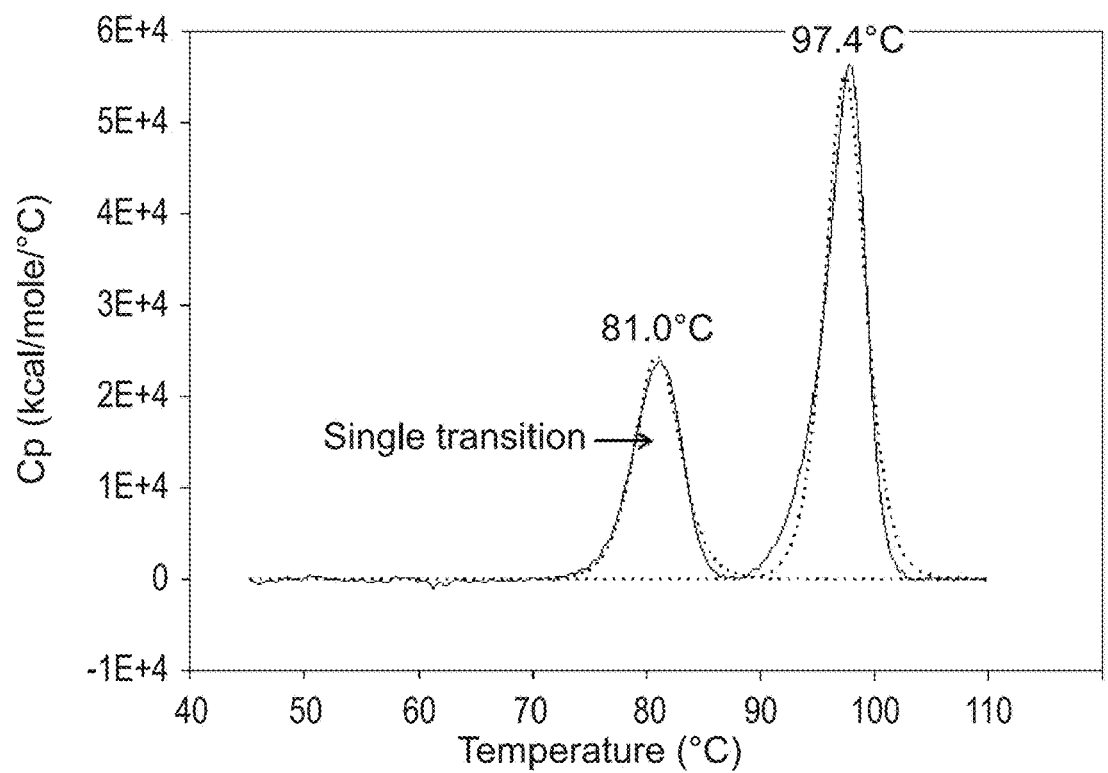
FIG. 11A-B—DSC analysis of gB705 at (FIG. 11A) pH 5.2 and (FIG. 11B) pH 8.7.
Figure 11B:
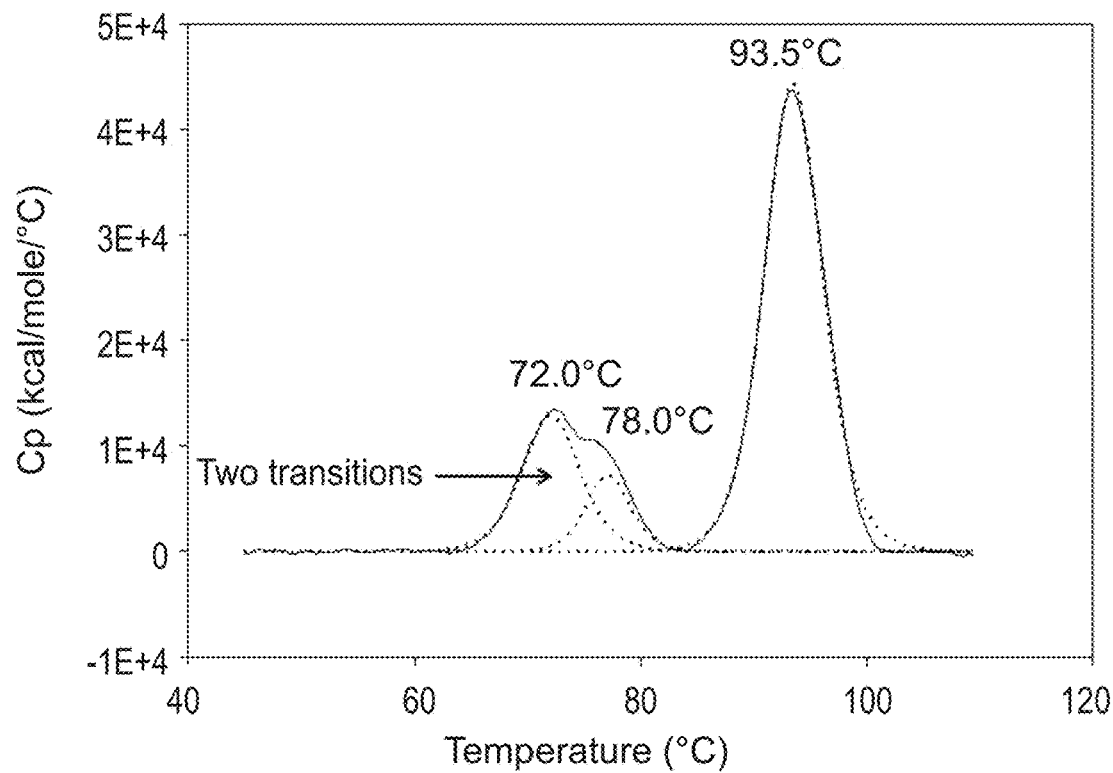
Figure 12A:
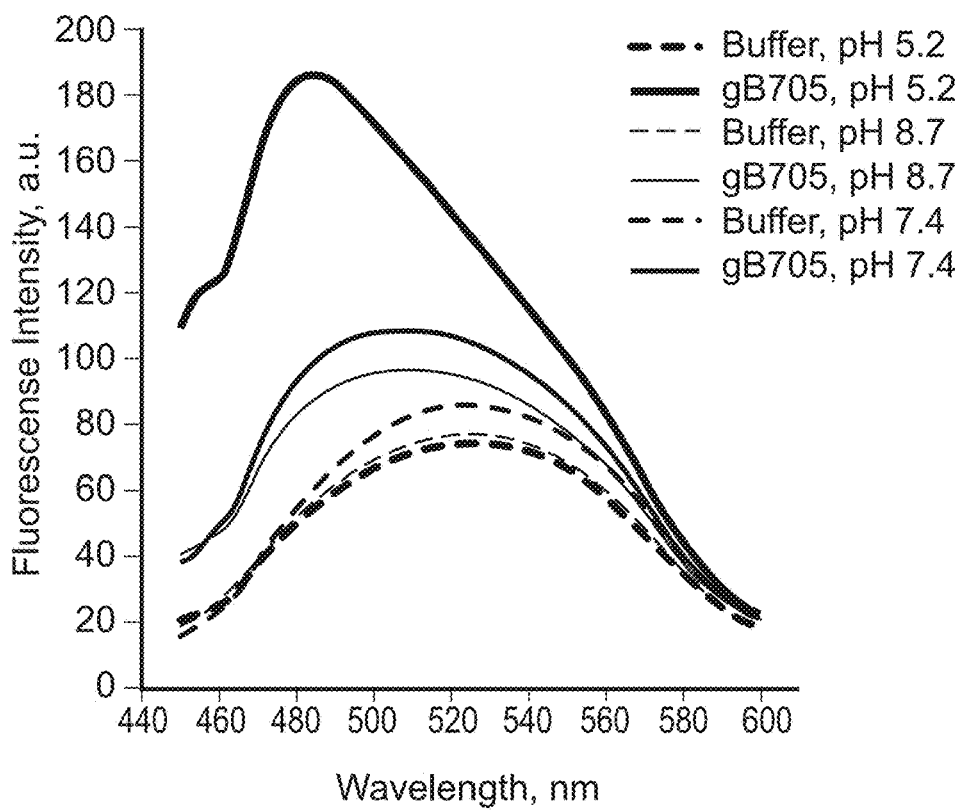

To evaluate the effect of pH on the HCMV gB705 protein, EDTA-treated gB705 protein was dialyzed into buffers at pH 5.2 and pH 8.7 and subjected to a series of biophysical characterization experiments to determine the changes, if any, in the secondary, tertiary and quaternary structure or hydrodynamic properties.
Sedimentation Velocity Analysis Sedimentation velocity analysis was performed on EDTA-treated gB705 at pH 5.2 and pH 8.7 (FIG. 8). No significant difference in migration or apparent molecular weight of the protein at different pHs was observed. FIG. 8A-B Sedimentation velocity analysis of EDTA-treated gB705 at pH 5.2 (A) and pH 8.7 (B).
Cryo Electron Microscopy Analysis Cryo electron microscopy analysis was performed on EDTA-treated gB705 proteins. The two images were collected on a Tecnia F20 electron microscope at the magnification of ×50,000 using low dose beam condition on a cryo frozen grid. The images showed that the gB705 was in monodispersed trimer form at either pH5.2 or pH 8.7 (FIG. 8C).
Far UV CD and Intrinsic Fluorescence Spectroscopy Both the Far UV CD (FIG. 9A) and intrinsic fluorescence spectroscopy (FIG. 9B) analyses suggest little change in the secondary structure of gB705 at pH 5.2 and pH 8.7. FIG. 9A Far UV CD analysis; FIG. 9B intrinsic fluorescence spectroscopy (ELN #00708337-0115, 0117)
Change in Tertiary Structure of gB705 Trimer at Different pHs Detected by Near-UV CD Spectroscopy Near-UV CD analysis was also performed to determine whether there is any difference in the tertiary structure of gB705 trimer at pH 5.2 and pH 8.7. The gB705 trimer exhibited differences in the spectroscopy profile under the two pH conditions (FIG. 10). This difference was strictly pH-dependent, because it was consistently observed when two different buffers were used at both pH 5.2 and pH 8.7. The lower fluorescence of gB705 in the normalized near-UV CD spectrum at pH 5.2 may be indicative of looser packing of the aromatic residues in gB705 trimer under acidic conditions. In short, change in environmental pH condition has a noticeable influence on the tertiary structure of gB705 trimer. FIG. 10 Near UV CD spectroscopy analysis of gB705 at pH 5.2 and pH 8.7. Buffer 1, 50 mM citrate, 100 mM phosphate; Buffer 2, 50 mM NaOAc; Buffer 3, 100 mM Na carbonate/bicarbonate; Buffer 4, 50 mM Na borate (ELN #00708337-0115, 0117).
Difference in Thermodynamic Melting at High and Low pH Conditions DSC analysis was performed to study the thermodynamic properties of gB705 at pH 5.2 and pH 8.7 (FIG. 11). The gB705 protein underwent a two-phase transition at pH 5.2, with a transitional melting temperature of 81.0° C. In stark contrast, the same protein prep demonstrated a three-phase transition at pH 8.7, with two transitional melting points at 72° C. and 78° C. respectively. The observed difference here indicates that there is significant structural difference, in terms of biophysical stability, in the gB705 trimer at pH 5.2 versus pH 8.7. FIG. 11 A-B: DSC analysis of gB705 at (FIG. 11A) pH 5.2 and (FIG. 11B) pH 8.7. At pH 8.7, the observed melting curve (in block line) was fit to the 4-state unfolding model and resolved to a three-phase transition pattern (in red lines) using the software provided by the DSC manufacturer. (ELN #00708337-0115, 0117).
Increase in Exposure of Hydrophobic Elements in gB705 Trimer at Acidic Condition
Difference in ANS Staining of gB705 at Different pH ANS is a fluorescent dye that binds to hydrophobic surfaces of protein, resulting in increased fluorescence intensity and shift in the emission maximum towards lower wavelengths. It was observed that ANS fluorescence intensity of gB705 was increased and its maximal emission was shifted to shorter wavelength of UV at pH 5.2, relative to those at pH 8.7 or pH 7.4 (FIG. 12A). These data are consistent with that hydrophobic surfaces of gB705 trimer are more exposed under acidic pH than under neutral or basic pH conditions.

The exposure of hydrophobic surfaces of gB705 trimer at different pH conditions is reversible To assess whether the difference in ANS binding ability of gB705 at different pHs is reversible or not, the gB705 protein at pH 5.2 was dialyzed into pH 8,7 buffer and vice versa, and then subjected to ANS analysis. The results showed that the protein gained ANS binding when shifted from high pH to low pH (FIG. 12B) and lost ANS binding when shifted from low pH to high pH (FIG. 12C). Therefore, the observed difference in ANS binding to gB705 are reversible.

Figure 12B:
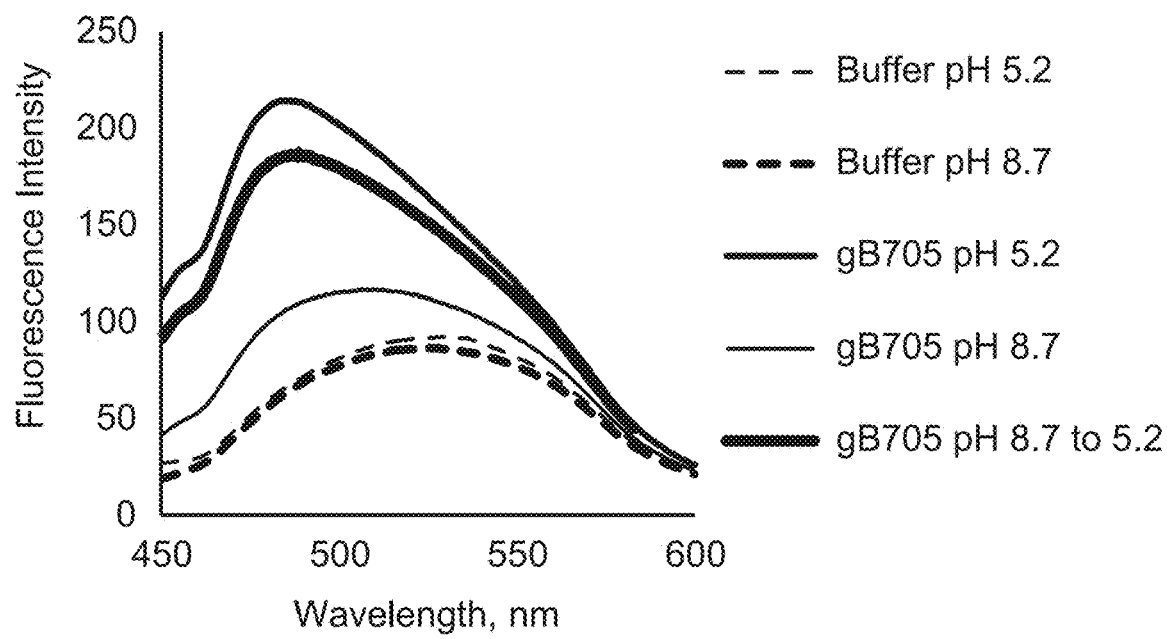
Figure 13:
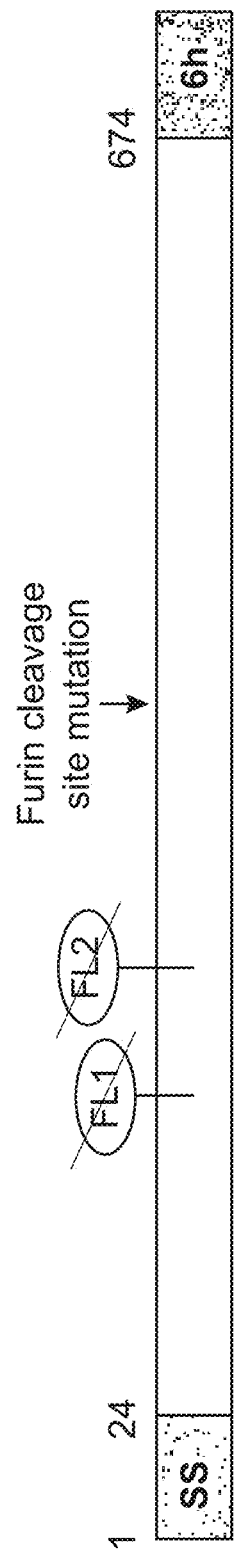
FIG. 13—illustration of RhCMV gB674 (SEQ ID NO: 7). SS represents a signal sequence; FL represents a fusion loop; 6h represents a 6× His tag FIG. 14—Graph showing anti-gB binding titers from six vaccines on week 9 after three doses of vaccination FIG. 15A-C—Six RhCMV(−) monkeys were immunized with placebo (A), recombinant RhCMV pentamer (B), or pentamer+RhCMV gB674 (C) intramuscularly in QS-21 adjuvant at week 0, 4 & 8. The animals were then challenged with live RhCMV (UCDE52 strain) orally for five times. Virus shedding in saliva samples were measured using qPCR (low limit of quantitation (LLOQ) is 125 DNA copy per ml) after virus challenge. Week 9 was one week after the third vaccination and one week prior to the first oral challenge. Week 15 was first sample at one week post the fifth virus challenge.

FIG. 12A-C: (A) ANS binding of gB705 at pH 5.2, pH 7.4 and pH 8.7 (ELN #00708337-0115, 0117); (B) ANS binding of gB705 at pH 8.7 and 5.2 and shifted from pH 8.7 to pH 5.2; (C) ANS binding of gB705 at pH 8.7 and 5.2 and shifted from pH 5.2 to pH 8.7 (ELN #00708329-0153)

Accordingly, a HCMV gB705 protein was produced. The protein contains the ectodomain of the VR1814 gB and mutations in the fusion loops and furin cleavage site. This protein may be in the postfusion conformation under neutral pH. The protein forms various oligomers after purification but can be transformed into homogenous singular trimer upon EDTA treatment.

No significant difference was observed in the secondary structure of EDTA-treated gB705 at pH 5.2 and pH 8.7, based on assays of far-UV CD spectroscopy, intrinsic fluorescence as well as sedimentation velocity analysis. However, significant differences in conformation of gB705 trimer are observed with various assays. Data from near-UV spectroscopy revealed significant difference in tertiary structure in gB705 trimer between pH 5.2 and pH 8.7. Data on extrinsic fluorescence after ANS staining suggest that the protein exhibits more exposed hydrophobic surfaces at pH 5.2, compared with at pH 8.7 and pH 7.2. The thermodynamic melting pattern of gB705 was significantly different between pH 5.2 and pH 8.7. Finally, the ANS staining analysis demonstrated that the conformational states of gB705 trimer exist in a reversible equilibrium, a property similar to VSV-G as a prototypic type III viral fusogen.

The gB705 protein exhibits a pH-dependent transition of conformation, which is a unique property and is biologically important. A non-postfusion conformation of gB (for example, gB705 at pH 8.7) may be a presented in a specific chemical/physical condition or by stabilizing its conformation with treatment of crosslinking agents. Such an immunogen may assume conformation state(s) that have a potential to elicit more robust nAb response than for example, recombinant gB protein in the postfusion conformation. Moreover, the pH-dependent transition of tertiary conformation of the gB705 trimer may be useful for improving solubility of the gB immunogen in an immunogenic composition, for improving stability of the immunogen, for improving binding of the immunogen to aluminum or other adjuvants, and/or for improving immunization of a vaccine comprising the immunogen, as compared, for example, to a recombinant gB protein that does not exhibit a pH-dependent transition of tertiary conformation, and/or as compared to a recombinant gB protein that does not include the following mutations Y155G, I156H, H157R, and W240A.

```
>HCMV VR1814 gB705
                                          (SEQ ID NO: 1)
MESRIWCLVVCVNLCIVCLGAVVSSSSTSHATSSAHNGSHTSRTTSAQTR

SVSSQHVTSSEAVSHRANETIYNTTLKYGDVVGVNTTKYPYRVCSMAQGT

DLIRFERNIVCTPMKPINEDLDEGIMVVYKRNIVAHTFKVRVYQKVLTFR

RSYAGHRTTYLLGSNTEYVAPPMWEIHHINRHSQCYSSYSRVIAGTVFVA

YHRDSYENKTMQLMLDDYSNTHSTRYVTVKDQWHSRGSTALYRETCNLNC

MVTITTARSKYPYHFFATSTGDWDISPFYNGTNRNTSYFGENADKFFIFP

NYTIVSDFGRANSAPETHRLVAFLERADSVISWDIQDEKNVTCQLTFWEA

SERTIRSEAEDSYHFSSAKMTATFLSKKQEVNMSDPVLDCVRDQALNKLQ

QIFNASYNQTYEKYGNVSVFETTGGLVVFWQGIKQKSLLELERLANSSGV

NSTRATKASTGNTTTLSLESESVRNVLYAQLQFTYDTLRSYINRALAQIA

EAWCVDQRRTLEVFKELSKINPSAILSAIYNKPIAARFMGDVLGLASCVT

INQTSVKVLRDMNVKESPGRCYSRPVVIFNFVNSSYVQYGQLGEDNEILL

GNHRTEECQFPSLKIFIAGNSAYEYVDYLFKRMIDLSSISTVDSMIALDI

DPLENTDFRVLELYSQKELRSSNVFDLEEIMREFNSYKQRVKYVEDKVVD

PLPP

>HCMV VR1814 gB705 (w/o Met)
                                          (SEQ ID NO: 2)
ESRIWCLVVCVNLCIVCLGAVVSSSSTSHATSSAHNGSHTSRTTSAQTRS

VSSQHVTSSEAVSHRANETIYNTTLKYGDWGVNTTKYPYRVCSMAQGTDL

IRFERNIVCTPMKPINEDLDEGIMWYKRNIVAHTFKVRVYQKVLTFRRSY

AGHRTTYLLGSNTEYVAPPMWEIHHINRHSQCYSSYSRVIAGTVFVAYHR

DSYENKTMQLMLDDYSNTHSTRYVTVKDQWHSRGSTALYRETCNLNCMVT

ITTARSKYPYHFFATSTGDWDISPFYNGTNRNTSYFGENADKFFIFPNYT

IVSDFGRANSAPETHRLVAFLERADSVISWDIQDEKNVTCQLTFWEASER

TIRSEAEDSYHFSSAKMTATFLSKKQEVNMSDPVLDCVRDQALNKLQQIF

NASYNQTYEKYGNVSVFETTGGLVVFWQGIKQKSLLELERLANSSGVNST

RATKASTGNTTTLSLESESVRNVLYAQLQFTYDTLRSYINRALAQIAEAW

CVDQRRTLEVFKELSKINPSAILSAIYNKPIAARFMGDVLGLASCVTINQ

TSVKVLRDMNVKESPGRCYSRPWIFNFVNSSYVQYGQLGEDNEILLGNHR

TEECQFPSLKIFIAGNSAYEYVDYLFKRMIDLSSISTVDSMIALDIDPLE

NTDFRVLELYSQKELRSSNVFDLEEIMREFNSYKQRVKYVEDKVVDPLPP

>HCMV VR1814 gB705 (residues 25-705 OF SEQ ID
NO: 1)
                                          (SEQ ID NO: 3)
SSSTSHATSSAHNGSHTSRTTSAQTRSVSSQHVTSSEAVSHRANETIYNT

TLKYGDWGVNTTKYPYRVCSMAQGTDLIRFERNIVCTPMKPINEDLDEGI

MWYKRNIVAHTFKVRVYQKVLTFRRSYAGHRTTYLLGSNTEYVAPPMWEI

HHINRHSQCYSSYSRVIAGTVFVAYHRDSYENKTMQLMLDDYSNTHSTRY

VTVKDQWHSRGSTALYRETCNLNCMVTITTARSKYPYHFFATSTGDVVDI

SPFYNGTNRNTSYFGENADKFFIFPNYTIVSDFGRANSAPETHRLVAFLE

RADSVISWDIQDEKNVTCQLTFWEASERTIRSEAEDSYHFSSAKMTATFL

SKKQEVNMSDPVLDCVRDQALNKLQQIFNASYNQTYEKYGNVSVFETTGG

LVVFWQGIKQKSLLELERLANSSGVNSTRATKASTGNTTTLSLESESVRN

VLYAQLQFTYDTLRSYINRALAQIAEAWCVDQRRTLEVFKELSKINPSAI

LSAIYNKPIAARFMGDVLGLASCVTINQTSVKVLRDMNVKESPGRCYSRP

VVIFNFVNSSYVQYGQLGEDNEILLGNHRTEECQFPSLKIFIAGNSAYEY

VDYLFKRMIDLSSISTVDSMIALDIDPLENTDFRVLELYSQKELRSSNVF

DLEEIMREFNSYKQRVKYVEDKWDPLPP

>signal sequence
                                          (SEQ ID NO: 4)
MESRIWCLVVCVNLCIVCLGAV >HCMV VR1814 gB705 with linker
                                          (SEQ ID NO: 5)
VSSSSTSHATSSAHNGSHTSRTTSAQTRSVSSQHVTSSEAVSHRANETI

YNTTLKYGDWGVNTTKYPYRVCSMAQGTDLIRFERNIVCTPMKPINEDL

DEGIMWYKRNIVAHTFKVRVYQKVLTFRRSYAGHRTTYLLGSNTEYVAP

PMWEIHHINRHSQCYSSYSRVIAGTVFVAYHRDSYENKTMQLMLDDYSN

THSTRYVTVKDQWHSRGSTALYRETCNLNCMVTITTARSKYPYHFFATS

TGDWDISPFYNGTNRNTSYFGENADKFFIFPNYTIVSDFGRANSAPETH

RLVAFLERADSVISWDIQDEKNVTCQLTFWEASERTIRSEAEDSYHFSS

AKMTATFLSKKQEVNMSDPVLDCVRDQALNKLQQIFNASYNQTYEKYGN

VSVFETTGGLWFWQGIKQKSLLELERLANSSGVNSTRATKASTGNTTTL

SLESESVRNVLYAQLQFTYDTLRSYINRALAQIAEAWCVDQRRTLEVFK

ELSKINPSAILSAIYNKPIAARFMGDVLGLASCVTINQTSVKVLRDMNV

KESPGRCYSRPWIFNFVNSSYVQYGQLGEDNEILLGNHRTEECQFPSLK

IFIAGNSAYEYVDYLFKRMIDLSSISTVDSMIALDIDPLENTDFRVLEL

YSQKELRSSNVFDLEEIMREFNSYKQRVKYVEDKVVDPLPPGSG
```

>ACZ79977.1 envelope glycoprotein B [Human betaherpesvirus 5]
(SEQ ID NO: 6)

MESRIWCLVVCVNLCIVCLGAVVSSSSTSHATSSAHNGSHTSRTTSAQT

RSVSSQHVTSSEAVSHRANETIYNTTLKYGDVVGVNTTKYPYRVCSMAQ

GTDLIRFERNIVCTPMKPINEDLDEGIMVVYKRNIVAHTFKVRVYQKVL

TFRRSYAYIHTTYLLGSNTEYVAPPMWEIHHINRHSQCYSSYSRVIAGT

VFVAYHRDSYENKTMQLMLDDYSNTHSTRYVTVKDQWHSRGSTWLYRET

CNLNCMVTITTARSKYPYHFFATSTGDWDISPFYNGTNRNTSYFGENAD

KFFIFPNYTIVSDFGRANSAPETHRLVAFLERADSVISWDIQDEKNVTC

QLTFWEASERTIRSEAEDSYHFSSAKMTATFLSKKQEVNMSDPVLDCVR

DQALNKLQQIFNASYNQTYEKYGNVSVFETTGGLVVFWQGIKQKSLLEL

ERLANSSGVNSTRRTKRSTGNTTTLSLESESVRNVLYAQLQFTYDTLRS

YINRALAQIAEAWCVDQRRTLEVFKELSKINPSAILSAIYNKPIAARFM

GDVLGLASCVTINQTSVKVLRDMNVKESPGRCYSRPVVIFNFVNSSYVQ

YGQLGEDNEILLGNHRTEECQFPSLKIFIAGNSAYEYVDYLFKRMIDLS

SISTVDSMIALDIDPLENTDFRVLELYSQKELRSSNVFDLEEIMREFNS

YKQRVKYVEDKVVDPLPPYLKGLDDLMSGLGAAGKAVGVAIGAVGGAVA

SVVEGVATFLKNPFGAFTIILVAIAVVIIIYLIYTRQRRLCMQPLQNLF

PYLVSADGTTVTSGNTKDTSLQAPPSYEESVYNSGRKGPGPPSSDASTA

APPYTNEQAYQMLLALARLDAEQRAQQNGTDSLDGQTGTQDKGQKPNLL

DRLRHRKNGYRHLKDSDEEENV

Example 7

CMV is a species-specific virus. Just has humans are infected by HCMV, rhesus macaques are infected by rhCMV, which has a biology similar to HCMV. This provides an animal model system for testing CMV vaccine inventions and technologies in ways that may be impractical or unethical in humans, such as certain infectious challenge experiments. Therefore, rhCMV analogues of HCMV antigens may be made to allow experimental investigation. RhCMV has a gB with a structure and function very similar to those of HCMV gB. A satisfactory correlation exists between effects in rhesus macaques relating to CMV and effects ultimately observed in humans. Accordingly, data from testing in rhesus macaques is reasonably predictive of the response in humans. Following this line reasoning, an analogous construct of HCMV gB705 construct, named as RhCMV gB674, was designed and tested in RhCMV(−) monkeys.

RhCMV gB674 Design

Following the same design of HCMV gB705, Pfizer's expression construct of RhCMV gB674 (SEQ ID NO: 7) was based on gB sequence of RhCMV strain UCD52, which contains amino acids 1-674 of the ectodomains and a 6× His affinity tag at the C-terminus. In addition, the gB674 protein contains three mutations (F128G, I129H, W213A) in the predicted fusion loops, because a fourth change in HCMV gB705 is pre-existing in the natural UCD52 sequence. Similarly, mutations (R429A/R430T/R432A) were introduced to totally inactivate the furin-like cleavage site, as illustrated.

Amino Acid Sequence:

>RhCMV gB674
(SEQ ID NO: 7)

```
  1  msknwfpllc asvlvvyvai assstgtasa vtpaptentt geiianttlr thevfrvnms
 61  kfpyrvcsma qgtdllrfeq nircdsfkpt kedfdegimv vykrdikpyt fkvhiyqkil
121  tfrqsysGHr enhllgfsqe rlavpmwevn yinrlnrcyn svvrnvagvt yvnyhkdsyv
181  netmhliedd ysnthsaryv tvkelwhkpg stAlyttscn vncmvtvtta rskypydffv
241  tsggevvdis pfyngsnneh fgenrdkfyi rrnysmvesy grdnaplvah elvafferpd
301  mlmswdivde anntceytfw eqsertirse adetyhftsh smtaffltlk kelnesdsdf
361  dcirdeaner lekifnttyn etyvksgnvs vyetsggliv fwlpvkekai wemqklateh
421  anntnatrAT kAstnsgnst kevlqnvvya qlqftydtlr nyinralrqi aeawckdqkr
481  tlevlkelsk inpsamlsai ydkpiaarfv gdvislarcv evdqnsvqvl rdmhtkekgl
541  cysrpvvlyt fvnsshvqyg qlgedneill grhrteaces pslkifiagn ssyeyvdyly
601  krmipldsis tvdtmisldi dplentdfra lelysrdelr ssnvfdledi mrefntykqr
661  mvhvegkvid nvpa gsghhhhhh
```

>RhCMV gB674
(SEQ ID NO: 8)

```
sknwfpllcasvlvvyvaiassstgtasavtpaptenttgeiianttlrthevfrvnmskfpyrvcsmaqgtdll
rfeqnircdsfkptkedfdegimvvykrdikpytfkvhiyqkiltfrqsysGHrenhllgfsqerlavpmwevny
inrlnrcynsvvrnvagvtyvnyhkdsyvnetmhlieddysnthsaryvtvkelwhkpgstAlyttscnvncmvt
vttarskypydffvtsggevvdispfyngsnnehfgenrdkfyirrnysmvesygrdnaplvahelvafferpdm
lmswdivdeanntceytfweqsertirseadetyhftshsmtatfltlkkelnesdsdfdcirdeanerlekifn
ttynetyvksgnvsvyetsggliwfwlpvkekaiwemqklatehanntnatrATkAstnsgnstkevlqnvvyaq
lqftydtlrnyinralrqiaeawckdqkrtlevlkelskinpsamlsaiydkpiaarfvgdvislarcvevdqns
```

-continued

```
vqvlrdmhtkekglcysrpvvlytfvnsshvqygqlgedneillgrhrteacespslkifiagnssyeyvdylyk
rmipldsistvdtmisldidplentdfralelysrdelrssnvfdledimrefntykqrmvhvegkvfdnvpags
ghhhhhh
```

>RhCMV gB (SEQ ID NO: 11)

```
MSKNWFPLLCASVLVVYVAIASSSTGTASAVTPAPTENTTGEIIANTTLRTHEVFRVN
MSKFPYRVCSMAQGTDLLRFEQNIRCDSFKPTKEDFDEGIMVVYKRDIKPYTFKVHI
YQKILTFRQSYSFIRENHLLGFSQERLAVPMWEVNYINRLNRCYNSVVRNVAGVTY
VNYHKDSYVNETMHLIEDDYSNTHSARYVTVKELWHKPGSTWLYTTSCNVNCMVT
VTTARSKYPYDFFVTSGGEVVDISPFYNGSNNEHFGENRDKFYIRRNYSMVESYGR
DNAPLVAHELVAFFERPDMLMSWDIVDEANNTCEYTFWEQSERTIRSEADETYHFT
SHSMTATFLTLKKELNESDSDFDCIRDEANERLEKIFNTTYNETYVKSGNVSVYETS
GGLIVFWLPVKEKAIWEMQKLATEHANNTNATRRRKRSTNSGNSTKEVLQNVVYA
QLQFTYDTLRNYINRALRQIAEAWCKDQKRTLEVLKELSKINPSAMLSAIYDKPIAAR
FVGDVISLARCVEVDQNSVQVLRDMHTKEKGLCYSRPVVLYTFVNSSHVQYGQLG
EDNEILLGRHRTEACESPSLKIFIAGNSSYEYVDYLYKRMIPLDSISTVDTMISLDIDPL
ENTDFRALELYSRDELRSSNVFDLEDIMREFNTYKQRMVHVEGKVFDNVPAYLRGL
DDMMSGLGSAGKALGVAIGAVGGAVASFVEGVVGFIENPFGSFTVILFLLAVLGVIY
LIYMRQKRAYEKPFEHFFPYVVPPTTVKEAPPSYEQSQYENIKEKAASATKEFSLEE
AYQMLLALQKLDQEKRRKAEADDEDFASNGQSAGFLDRLRNRRRGGYQKIQNEYE
V
```

Example 8

Analytics of RhCMV gB674

1. SDS-PAGE analysis of gB674 (ELN 00707788-0011)

Figure 17A:
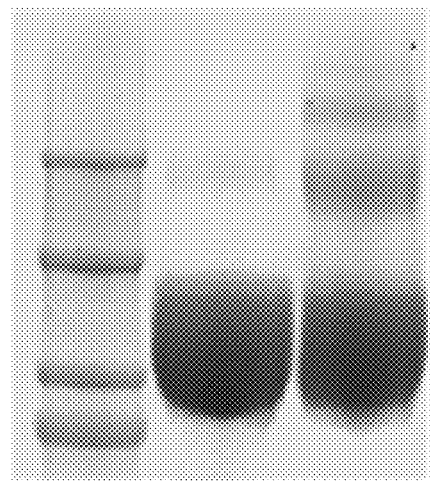
FIG. 17A-B—(A) SDS-PAGE analysis of rhesus gB674, demonstrating the lack of protease cleavage as designed and >95% purity, NR=non-reducing; R=reducing; (B) Size Exclusion chromatography of rhesus gB674 protein showing elution as a major peak (MW ~313 kDa), consistent with a homogenous individual trimer

The gB674 protein was transiently expressed in Expi293 cells and purified via the C-terminal 6× His tag. On SDS-PAGE, the protein exhibited a single band under reducing (R) conditions, demonstrating the lack of protease cleavage as designed and >98% purity. Some oligomeric forms were shown under a non-reducing condition. See FIG. 17A.

2. Size Exclusion chromatography (ELN 00707788-0011)

Figure 17B:
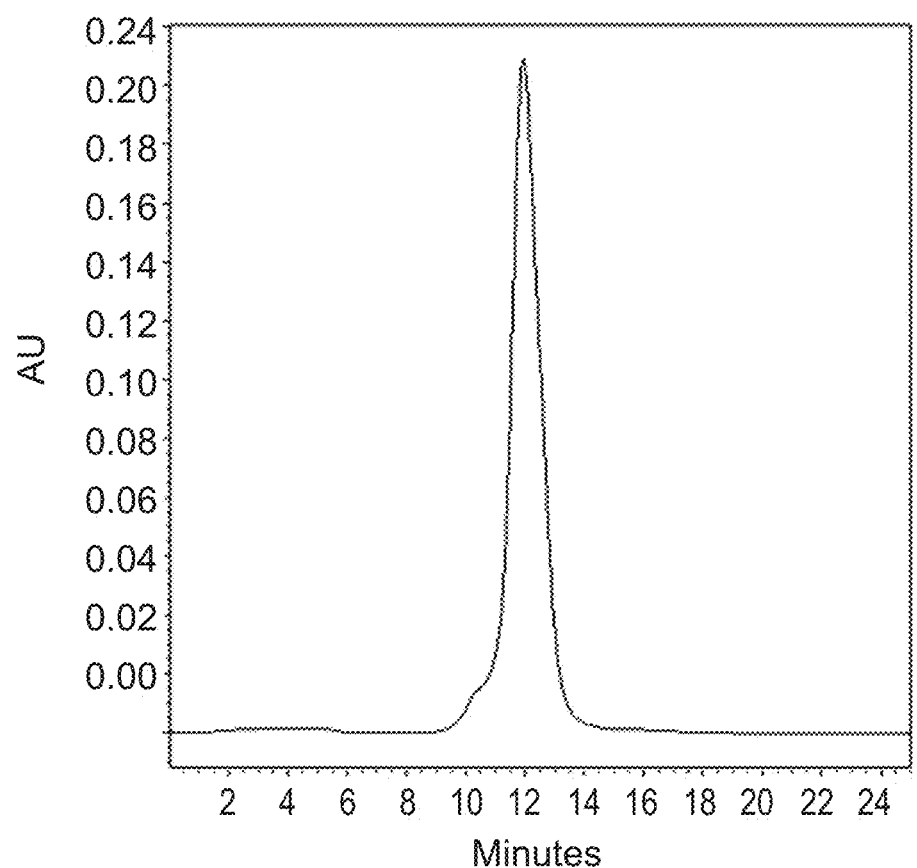

The gB674 protein was treated with EDTA after purification and analyzed on Superose-6 column. As observed with HCMV gB705, gB674 protein was eluted as a major peak, consistent with a homogenous individual trimer. See FIG. 17B.

Immunogenicity Testing:

RhCMV(−) rhesus monkeys were screened and proven as seronegative for anti-gB by an ELISA test (data not shown). Six animals were immunized intramuscularly with 100 ug of gB674 per dose and 50 vg of RhCMV pentamer in 50 ug of QS-21 adjuvant at week 0, 4 and 8. A group of six animals were injected with a placebo regimen lacking only the gB protein, as controls.

Figure 14:
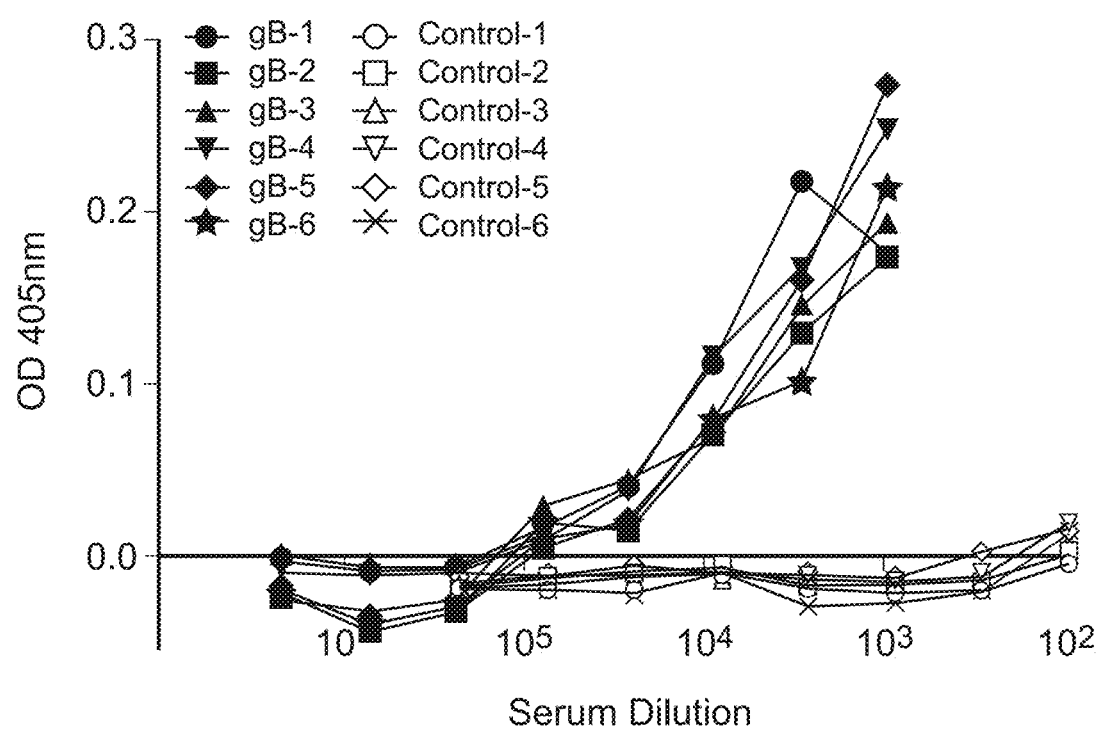

At week 9, anti-gB response was detected in an ELISA using recombinant RhCMV gB lacking a C-terminal 6× His tag. In so doing, the ELISA avoids detection of antibody responses to the 6His tags on the gB and pentamer antigens in the vaccine. Sera from all six animals in the control group (animals C1-C6 in FIG. 14) were negative of anti-gB at a 1:100 dilution on week 9, as expected. The anti-gB binding titers from the six vaccines (animals V1-V6 in FIG. 14) on week 9 after three doses of vaccination were detected. Thus, recombinant gB674 of RhCMV UCD52 is highly immunogenic. This provides supporting evidence of recombinant gB705 of HCMV as a vaccine antigen.

Example 9

Efficacy Testing of the Rhesus Equivalent of HCMV gB705

Figure 15A:
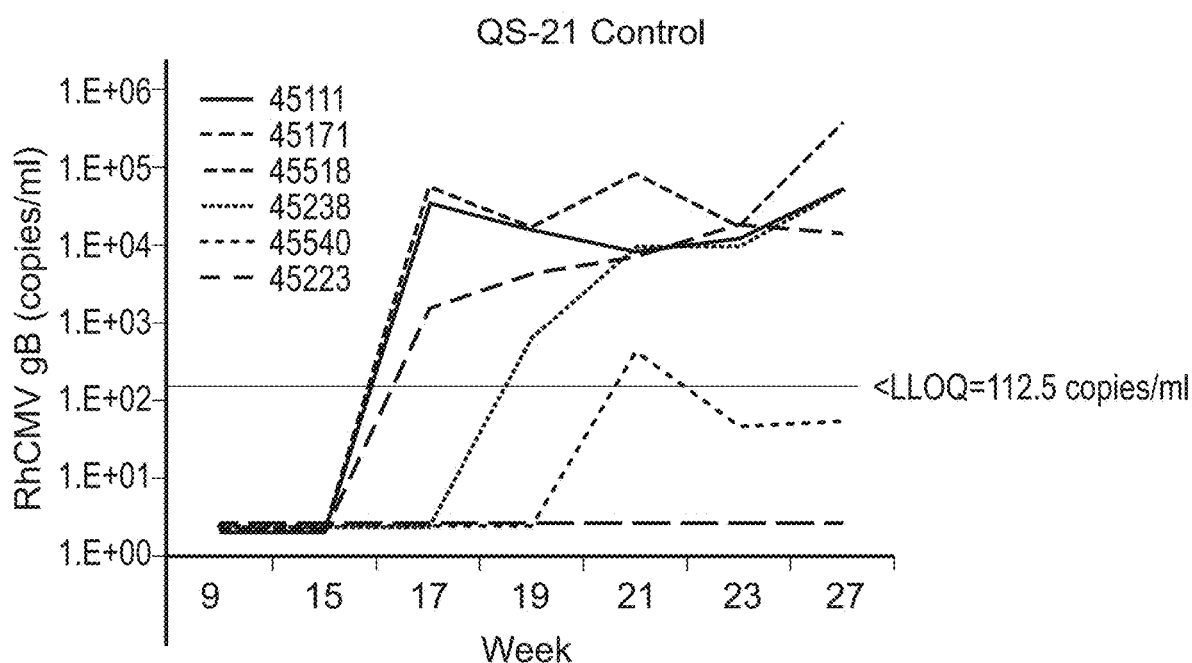
Figure 15B:
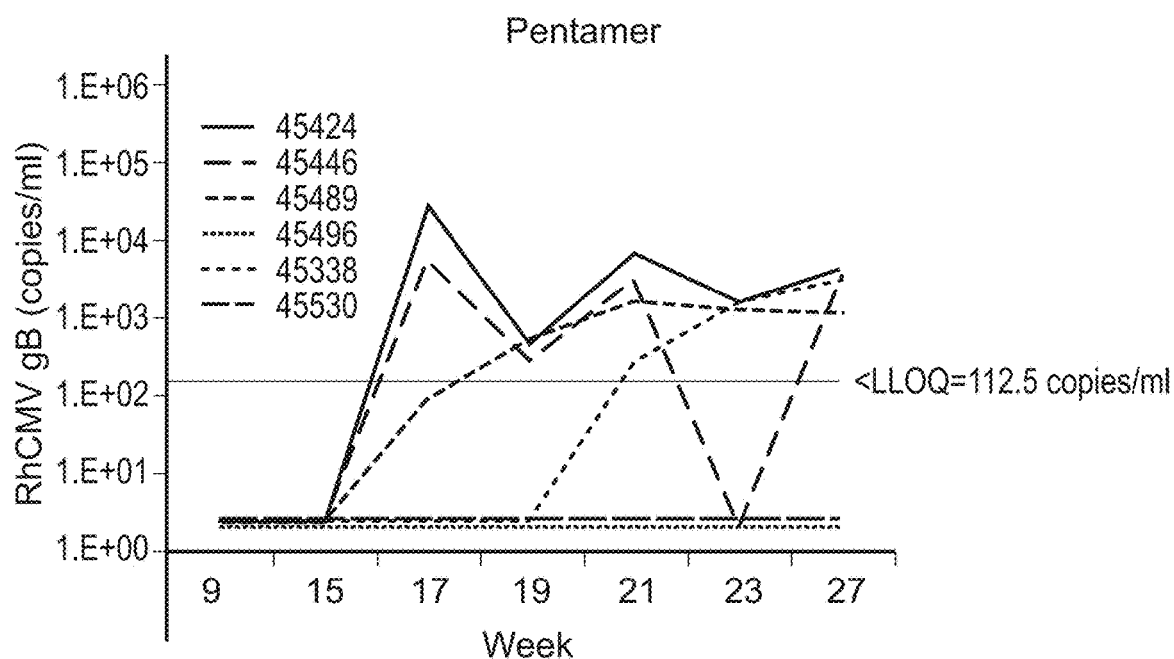
Figure 15C:
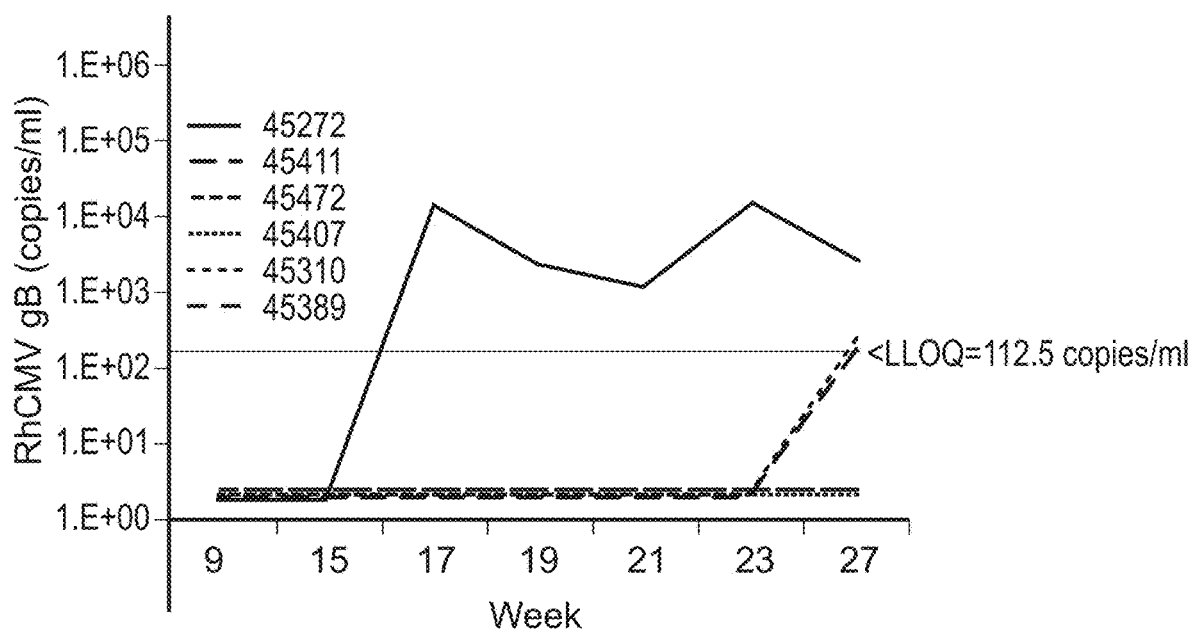

Utility of the new design of HCMV post-fusion gB705 was tested by evaluating the protective efficacy of immunization with RhCMV gB674 protein (SEQ ID NO: 7) in an oral RhCMV infectious challenge model in RhCMV(−) rhesus monkeys. The candidate monkeys were screened and proven seronegative for gB by an ELISA test (data not shown). Six animals in each of three experimental groups were immunized intramuscularly at weeks 0, 4 and 8. All formulations, including the control formulation, had a pH of 7.7 and contained 50 µg of the QS-21 adjuvant. Six animals in one group of six animals were injected with a placebo formulation, containing no antigen, as negative controls. Six animals in a second group were immunized with 50 µg each of a recombinant RhCMV pentamer complex (containing the gH, gL, pUL128, pUL130, and pUL131 RhCMV antigens). Six animals in a third group were each immunized with 100 µg of gB674+50 µg of recombinant RhCMV pentamer. Two weeks after the third vaccination, all animals were challenged with $8×10^5$ plaque-forming units (PFU) of UCD52 RhCMV viral stock by oral inoculation, and the challenge was repeated weekly for a total of 5 times. This study was designed to demonstrate whether recombinant gB674 would add extra protective efficacy to a vaccine formulation containing recombinant RhCMV pentamer as the sole antigen. Virus infection was monitored by the presence of viremia and by virus shedding in saliva and urine compartments. The presence of virus in these target samples was quantified by a qPCR assay with a limit of quantitation of 125 DNA copies/ml. As shown in FIG. 15 panel A, five oral challenges led to virus shedding in saliva in 5 of 6 animals in the control group. Week 9 and week 15 are one week prior to the first virus challenge and one week after the fifth virus challenge, respectively. The same five control animals had viremia and high level of virus shedding in urine (data not shown). Five of six animals in both the pentamer and the pentamer+gB groups of animals also acquired virus infection, but with modestly reduced levels of viremia and urine virus shedding (data not shown). Vaccination with pentamer alone led to some reduction of virus shedding in saliva, FIG. 15 panel B. Importantly, inclusion of gB674 in combination with the pentamer resulted in significant delay and reduction in saliva virus shedding, relative to immunization with the pentamer alone, FIG. 15 panel C. This result indicates that adding the gB674 to the pentamer reduced viral shedding in the urine. This likely reflects limitation of virus infection of the kidneys of the monkeys that received the combination of pentamer and gB antigens. This result demonstrates the utility of the rhCMV gB674 antigen as a protective vaccine antigen, and by extension, of the analogous HCMV gB705 antigen.

The Following Clauses Describe Additional Embodiments of the Invention:

C1. A polypeptide comprising at least one mutation in the fusion loop 1 (FL1) region of an HCMV gB polypeptide.
C2. A polypeptide comprising at least one mutation in the fusion loop 2 (FL2) region of an HCMV gB polypeptide.
C3. A polypeptide comprising at least one mutation in the fusion loop 1 (FL1) region and the fusion loop 2 (FL2) region of an HCMV gB polypeptide.
C4. A polypeptide comprising at least one mutation in the furin-like cleavage site of an HCMV gB polypeptide.
C5. A polypeptide comprising at least two mutations in the fusion loop 2 (FL2) region of an HCMV gB polypeptide.
C6. A polypeptide comprising at least two mutations in the fusion loop 1 (FL1) region and the fusion loop 2 (FL2) region of an HCMV gB polypeptide.
C7. A polypeptide comprising at least two mutations in the furin-like cleavage site of an HCMV gB polypeptide.
C8. A polypeptide comprising a mutation at position Y155, as compared to SEQ ID NO: 6.
C9. A polypeptide comprising a mutation at positions Y155 and I156, as compared to SEQ ID NO: 6.
C10. A polypeptide comprising a mutation at positions Y155, I156, and H157, as compared to SEQ ID NO: 6.
C11. A polypeptide comprising a mutation at positions I156 and H157, as compared to SEQ ID NO: 6.
C12. A polypeptide comprising a mutation at positions Y155, I156, H157, and W240, as compared to SEQ ID NO: 6.
C13. A polypeptide comprising a mutation at positions Y155 and W240, as compared to SEQ ID NO: 6.
C14. A polypeptide comprising a mutation at positions Y155, H157, and W240, as compared to SEQ ID NO: 6.
C15. A polypeptide comprising a mutation at positions Y155 and H157, as compared to SEQ ID NO: 6.
C16. A polypeptide comprising the mutation Y155G, as compared to SEQ ID NO: 6.
C17. A polypeptide comprising the mutations Y155G and I156H, as compared to SEQ ID NO: 6.
C18. A polypeptide comprising the mutations Y155G, I156H, and H157R, as compared to SEQ ID NO: 6.
C19. A polypeptide comprising the mutations I156H and H157R, as compared to SEQ ID NO: 6.
C20. A polypeptide comprising the mutations Y155G, I156H, H157R, and W240A, as compared to SEQ ID NO: 6.
C21. A polypeptide comprising the mutations Y155G and W240A, as compared to SEQ ID NO: 6.
C22. A polypeptide comprising the mutations Y155G, H157R, and W240A, as compared to SEQ ID NO: 6.
C23. A polypeptide comprising the mutations Y155G and H157R, as compared to SEQ ID NO: 6.
C24. A polypeptide comprising an amino acid sequence that is at least about 60% identical to SEQ ID NO: 1.
C25. A polypeptide comprising an amino acid sequence that is at least about 60% identical to SEQ ID NO: 2.
C26. A polypeptide comprising an amino acid sequence that is at least about 60% identical to SEQ ID NO: 3.
C27. A polypeptide comprising an amino acid sequence that is at least about 60% identical to SEQ ID NO: 5.
C28. A polypeptide comprising an amino acid sequence that is at least about 60% identical to SEQ ID NO: 7.
C29. A polypeptide comprising an amino acid sequence that is at least about 60% identical to SEQ ID NO: 8.
C30. A polypeptide comprising the amino acid sequence set forth in SEQ ID NO: 1.
C31. A polypeptide comprising the amino acid sequence set forth in SEQ ID NO: 2.
C32. A polypeptide comprising the amino acid sequence set forth in SEQ ID NO: 3.
C33. A polypeptide comprising the amino acid sequence set forth in SEQ ID NO: 5.
C34. A polypeptide comprising the amino acid sequence set forth in SEQ ID NO: 7.
C35. A polypeptide comprising the amino acid sequence set forth in SEQ ID NO: 8.
C36. The polypeptide according to any one of clauses C1-C35, wherein the polypeptide does not comprise a mutation at any one of the following positions: (i) R236, (ii) G237, (iii) T158; (iv) Y242.
C37. The polypeptide according to any one of clauses C1-C35, wherein the polypeptide does not comprise any one of the following mutations: (i) R236N, (ii) G237N, (iii) T158N; (iv) Y242T, (v) Y242S; (vi) Y242C.
C38. The polypeptide according to any one of clauses C1-C37, wherein the amino acid sequence SEQ ID NO: 9 is a part of the polypeptide sequence.
C39. The polypeptide according to any one of clauses C1-C37, wherein the amino acid sequence SEQ ID NO: 10 is a part of the polypeptide sequence.
C40. The polypeptide according to any one of clauses C1-C37, wherein the amino acid sequences of SEQ ID NO: 9 and SEQ ID NO: 10 is a part of the polypeptide sequence.
C41. The polypeptide according to any one of clauses C1-C40, wherein the polypeptide does not comprise a protease cleavage site.
C42. The polypeptide according to any one of clauses C1-C40, wherein the polypeptide does not comprise a wild-type CMV protease cleavage site.
C43. The polypeptide according to any one of clauses C1-C40, wherein the polypeptide does not comprise a non-naturally occurring protease cleavage site that replaces the wild-type CMV protease cleavage site.
C44. The polypeptide according to any one of clauses C1-C40, wherein the polypeptide does not comprise an N-glycosylation site comprising N-X-S/T/C motif, wherein X is any amino acid residue.
C45. The polypeptide according to any one of clauses C1-C40, wherein the polypeptide does not comprise a modified amino acid sequence that introduces an O-linked glycosylation site.
C46. The polypeptide according to any one of clauses C1-C45, wherein the polypeptide does not include a deletion or substitution of any one of the amino acid residues selected from the group consisting of 154, 158, 159, 160, 230, 231, 232, 233, 234, 235, 236, 237, 238, 239, 241, and 242, according to the numbering of SEQ ID NO: 6.
C47. The polypeptide according to any one of clauses C1-C46, wherein the polypeptide does not include a mutation of any one of the amino acid residues: Y160, R236, S238, T239, and Y242, according to the numbering of SEQ ID NO: 6.
C48. The polypeptide according to any one of clauses C1-C47, wherein the polypeptide does not include the cytoplasmic tail of HCMV gB.
C49. The polypeptide according to any one of clauses C1-C48, wherein the polypeptide does not contain an insect cell pattern of glycosylation.

C50. The polypeptide according to any one of clauses C1-C49, wherein the polypeptide is contacted with ethylenediaminetetraacetic acid (EDTA).

C51. The polypeptide according to any one of clauses C1-C50, wherein the polypeptide undergoes a structural conformation change in response to a pH change.

C52. The polypeptide according to clause C51, wherein the polypeptide exhibits improved solubility or stability, as compared to a recombinant gB protein that does not include the following mutations Y155G, I156H, H157R, and W240A.

C53. A composition comprising the polypeptide according to any one of clauses C1-C51, and a diluent.

C54. A composition comprising the polypeptide according to any one of clauses C1-C51, and an adjuvant.

C55. The composition according to any one of clauses C53-C54, wherein the composition is immunogenic.

C56. The composition of clause C55, for use in inducing an immune response against cytomegalovirus.

C57. A recombinant nucleic acid molecule encoding the polypeptide according to any one of clauses C1-C51, wherein the polypeptide undergoes a structural conformation change in response to a pH change.

C58. The recombinant nucleic acid molecule according to clause C57, wherein said recombinant nucleic acid (a) is not a self-replicating RNA molecule; (b) is not an alphavirus replicon; (c) does not encode any alphavirus nonstructural proteins, such as NSP1, NSP2, NSP3 and NSP4; (d) does not contain: an Internal Ribosomal Entry Site (IRES), such as EMCV or EV71 and/or (e) does not contain a viral 2A site, such as FMDV.

C59. A method for raising antibodies using the polypeptide according to any one of clauses C1-C51.

C60. The antibody according to clause C59, wherein said antibody is for use in a diagnostic assay.

C61. The antibody according to clause C59, wherein said antibody is labelled directly or indirectly.

C62. The antibody according to clause C59, wherein said antibody is for use in therapy.

C63. A method of eliciting an immune response in a mammal, the method comprising administering to the mammal an effective amount of the polypeptide according to any one of clauses C1-C51.

C64. A method for reducing cytomegalovirus viral shedding in a mammal, the method comprising administering to the mammal an effective amount of the polypeptide according to any one of clauses C1-C51.

C65. The method according to clause C64, wherein the reduction in viral shedding is as compared to the viral shedding following an administration of a CMV pentamer.

C66. The method according to clause C64, wherein the challenge virus is homologous to the VR1814 CMV strain.

C67. The method according to clause C64, wherein the challenge virus is homologous to the macacine herpesvirus 3 isolate 21252 CMV strain.

The invention claimed is:

1. A polypeptide comprising the amino acid sequence set forth in SEQ ID NO: 1.

2. A polypeptide comprising the amino acid sequence set forth in SEQ ID NO: 2.

3. A polypeptide comprising the amino acid sequence set forth in SEQ ID NO: 7.

4. The polypeptide according to any one of claims 1-3, wherein the polypeptide does not include the cytoplasmic tail of HCMV gB.

5. The polypeptide according to any one of claims 1-3, wherein the polypeptide does not contain an insect cell pattern of glycosylation.

6. The polypeptide according to any one of claims 1-3, wherein the polypeptide has been contacted with ethylenediaminetetraacetic acid (EDTA).

7. The polypeptide according to any one of claims 1-3, wherein the polypeptide undergoes a structural conformation change in response to a pH change.

8. A composition comprising the polypeptide according to any one of claims 1-3, and a diluent.

* * * * *

SEQUENCE LISTING

```
<160> NUMBER OF SEQ ID NOS: 15

<210> SEQ ID NO 1
<211> LENGTH: 705
<212> TYPE: PRT
<213> ORGANISM: Artificial Sequence
<220> FEATURE:
<223> OTHER INFORMATION: Synthetic amino acid sequence

<400> SEQUENCE: 1

Met Glu Ser Arg Ile Trp Cys Leu Val Val Cys Val Asn Leu Cys Ile
1               5                   10                  15

Val Cys Leu Gly Ala Val Val Ser Ser Ser Thr Ser His Ala Thr
            20                  25                  30

Ser Ser Ala His Asn Gly Ser His Thr Ser Arg Thr Thr Ser Ala Gln
        35                  40                  45

Thr Arg Ser Val Ser Ser Gln His Val Thr Ser Ser Glu Ala Val Ser
    50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Pro Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Gly His Arg Thr Thr Tyr
145                 150                 155                 160
```

-continued

```
Leu Leu Gly Ser Asn Thr Glu Tyr Val Ala Pro Pro Met Trp Glu Ile
            165                 170                 175
His His Ile Asn Arg His Ser Gln Cys Tyr Ser Ser Tyr Ser Arg Val
            180                 185                 190
Ile Ala Gly Thr Val Phe Val Ala Tyr His Arg Asp Ser Tyr Glu Asn
            195                 200                 205
Lys Thr Met Gln Leu Met Leu Asp Asp Tyr Ser Asn Thr His Ser Thr
            210                 215                 220
Arg Tyr Val Thr Val Lys Asp Gln Trp His Ser Arg Gly Ser Thr Ala
225                 230                 235                 240
Leu Tyr Arg Glu Thr Cys Asn Leu Asn Cys Met Val Thr Ile Thr Thr
            245                 250                 255
Ala Arg Ser Lys Tyr Pro Tyr His Phe Phe Ala Thr Ser Thr Gly Asp
            260                 265                 270
Val Val Asp Ile Ser Pro Phe Tyr Asn Gly Thr Asn Arg Asn Thr Ser
            275                 280                 285
Tyr Phe Gly Glu Asn Ala Asp Lys Phe Ile Phe Pro Asn Tyr Thr
            290                 295                 300
Ile Val Ser Asp Phe Gly Arg Ala Asn Ser Ala Pro Glu Thr His Arg
305                 310                 315                 320
Leu Val Ala Phe Leu Glu Arg Ala Asp Ser Val Ile Ser Trp Asp Ile
            325                 330                 335
Gln Asp Glu Lys Asn Val Thr Cys Gln Leu Thr Phe Trp Glu Ala Ser
            340                 345                 350
Glu Arg Thr Ile Arg Ser Glu Ala Glu Asp Ser Tyr His Phe Ser Ser
            355                 360                 365
Ala Lys Met Thr Ala Thr Phe Leu Ser Lys Lys Gln Glu Val Asn Met
            370                 375                 380
Ser Asp Pro Val Leu Asp Cys Val Arg Asp Gln Ala Leu Asn Lys Leu
385                 390                 395                 400
Gln Gln Ile Phe Asn Ala Ser Tyr Asn Gln Thr Tyr Glu Lys Tyr Gly
            405                 410                 415
Asn Val Ser Val Phe Glu Thr Thr Gly Gly Leu Val Val Phe Trp Gln
            420                 425                 430
Gly Ile Lys Gln Lys Ser Leu Leu Glu Leu Glu Arg Leu Ala Asn Ser
            435                 440                 445
Ser Gly Val Asn Ser Thr Arg Ala Thr Lys Ala Ser Thr Gly Asn Thr
450                 455                 460
Thr Thr Leu Ser Leu Glu Ser Glu Ser Val Arg Asn Val Leu Tyr Ala
465                 470                 475                 480
Gln Leu Gln Phe Thr Tyr Asp Thr Leu Arg Ser Tyr Ile Asn Arg Ala
            485                 490                 495
Leu Ala Gln Ile Ala Glu Ala Trp Cys Val Asp Gln Arg Arg Thr Leu
            500                 505                 510
Glu Val Phe Lys Glu Leu Ser Lys Ile Asn Pro Ser Ala Ile Leu Ser
            515                 520                 525
Ala Ile Tyr Asn Lys Pro Ile Ala Ala Arg Phe Met Gly Asp Val Leu
            530                 535                 540
Gly Leu Ala Ser Cys Val Thr Ile Asn Gln Thr Ser Val Lys Val Leu
545                 550                 555                 560
Arg Asp Met Asn Val Lys Glu Ser Pro Gly Arg Cys Tyr Ser Arg Pro
            565                 570                 575
Val Val Ile Phe Asn Phe Val Asn Ser Ser Tyr Val Gln Tyr Gly Gln
```

```
                    580                 585                 590
Leu Gly Glu Asp Asn Glu Ile Leu Leu Gly Asn His Arg Thr Glu Glu
            595                 600                 605

Cys Gln Phe Pro Ser Leu Lys Ile Phe Ile Ala Gly Asn Ser Ala Tyr
        610                 615                 620

Glu Tyr Val Asp Tyr Leu Phe Lys Arg Met Ile Asp Leu Ser Ser Ile
625                 630                 635                 640

Ser Thr Val Asp Ser Met Ile Ala Leu Asp Ile Asp Pro Leu Glu Asn
                645                 650                 655

Thr Asp Phe Arg Val Leu Glu Leu Tyr Ser Gln Lys Glu Leu Arg Ser
            660                 665                 670

Ser Asn Val Phe Asp Leu Glu Glu Ile Met Arg Glu Phe Asn Ser Tyr
        675                 680                 685

Lys Gln Arg Val Lys Tyr Val Glu Asp Lys Val Val Asp Pro Leu Pro
    690                 695                 700

Pro
705

<210> SEQ ID NO 2
<211> LENGTH: 704
<212> TYPE: PRT
<213> ORGANISM: Artificial Sequence
<220> FEATURE:
<223> OTHER INFORMATION: Synthetic amino acid sequence

<400> SEQUENCE: 2

Glu Ser Arg Ile Trp Cys Leu Val Val Cys Val Asn Leu Cys Ile Val
1               5                   10                  15

Cys Leu Gly Ala Val Val Ser Ser Ser Thr Ser His Ala Thr Ser
            20                  25                  30

Ser Ala His Asn Gly Ser His Thr Ser Arg Thr Thr Ser Ala Gln Thr
        35                  40                  45

Arg Ser Val Ser Ser Gln His Val Thr Ser Ser Glu Ala Val Ser His
    50                  55                  60

Arg Ala Asn Glu Thr Ile Tyr Asn Thr Thr Leu Lys Tyr Gly Asp Val
65                  70                  75                  80

Val Gly Val Asn Thr Thr Lys Tyr Pro Tyr Arg Val Cys Ser Met Ala
                85                  90                  95

Gln Gly Thr Asp Leu Ile Arg Phe Glu Arg Asn Ile Val Cys Thr Pro
            100                 105                 110

Met Lys Pro Ile Asn Glu Asp Leu Asp Glu Gly Ile Met Val Val Tyr
        115                 120                 125

Lys Arg Asn Ile Val Ala His Thr Phe Lys Val Arg Val Tyr Gln Lys
    130                 135                 140

Val Leu Thr Phe Arg Arg Ser Tyr Ala Gly His Arg Thr Thr Tyr Leu
145                 150                 155                 160

Leu Gly Ser Asn Thr Glu Tyr Val Ala Pro Pro Met Trp Glu Ile His
                165                 170                 175

His Ile Asn Arg His Ser Gln Cys Tyr Ser Ser Tyr Ser Arg Val Ile
            180                 185                 190

Ala Gly Thr Val Phe Val Ala Tyr His Arg Asp Ser Tyr Glu Asn Lys
        195                 200                 205

Thr Met Gln Leu Met Leu Asp Asp Tyr Ser Asn Thr His Ser Thr Arg
    210                 215                 220

Tyr Val Thr Val Lys Asp Gln Trp His Ser Arg Gly Ser Thr Ala Leu
```

```
                225                 230                 235                 240
Tyr Arg Glu Thr Cys Asn Leu Asn Cys Met Val Thr Ile Thr Thr Ala
                245                 250                 255
Arg Ser Lys Tyr Pro Tyr His Phe Phe Ala Thr Ser Thr Gly Asp Val
                260                 265                 270
Val Asp Ile Ser Pro Phe Tyr Asn Gly Thr Asn Arg Asn Thr Ser Tyr
                275                 280                 285
Phe Gly Glu Asn Ala Asp Lys Phe Phe Ile Phe Pro Asn Tyr Thr Ile
                290                 295                 300
Val Ser Asp Phe Gly Arg Ala Asn Ser Ala Pro Glu Thr His Arg Leu
305                 310                 315                 320
Val Ala Phe Leu Glu Arg Ala Asp Ser Val Ile Ser Trp Asp Ile Gln
                325                 330                 335
Asp Glu Lys Asn Val Thr Cys Gln Leu Thr Phe Trp Glu Ala Ser Glu
                340                 345                 350
Arg Thr Ile Arg Ser Glu Ala Glu Asp Ser Tyr His Phe Ser Ser Ala
                355                 360                 365
Lys Met Thr Ala Thr Phe Leu Ser Lys Lys Gln Glu Val Asn Met Ser
                370                 375                 380
Asp Pro Val Leu Asp Cys Val Arg Asp Gln Ala Leu Asn Lys Leu Gln
385                 390                 395                 400
Gln Ile Phe Asn Ala Ser Tyr Asn Gln Thr Tyr Glu Lys Tyr Gly Asn
                405                 410                 415
Val Ser Val Phe Glu Thr Thr Gly Gly Leu Val Val Phe Trp Gln Gly
                420                 425                 430
Ile Lys Gln Lys Ser Leu Leu Glu Leu Glu Arg Leu Ala Asn Ser Ser
                435                 440                 445
Gly Val Asn Ser Thr Arg Ala Thr Lys Ala Ser Thr Gly Asn Thr Thr
                450                 455                 460
Thr Leu Ser Leu Glu Ser Glu Ser Val Arg Asn Val Leu Tyr Ala Gln
465                 470                 475                 480
Leu Gln Phe Thr Tyr Asp Thr Leu Arg Ser Tyr Ile Asn Arg Ala Leu
                485                 490                 495
Ala Gln Ile Ala Glu Ala Trp Cys Val Asp Gln Arg Arg Thr Leu Glu
                500                 505                 510
Val Phe Lys Glu Leu Ser Lys Ile Asn Pro Ser Ala Ile Leu Ser Ala
                515                 520                 525
Ile Tyr Asn Lys Pro Ile Ala Ala Arg Phe Met Gly Asp Val Leu Gly
                530                 535                 540
Leu Ala Ser Cys Val Thr Ile Asn Gln Thr Ser Val Lys Val Leu Arg
545                 550                 555                 560
Asp Met Asn Val Lys Glu Ser Pro Gly Arg Cys Tyr Ser Arg Pro Val
                565                 570                 575
Val Ile Phe Asn Phe Val Asn Ser Ser Tyr Val Gln Tyr Gly Gln Leu
                580                 585                 590
Gly Glu Asp Asn Glu Ile Leu Leu Gly Asn His Arg Thr Glu Glu Cys
                595                 600                 605
Gln Phe Pro Ser Leu Lys Ile Phe Ile Ala Gly Asn Ser Ala Tyr Glu
                610                 615                 620
Tyr Val Asp Tyr Leu Phe Lys Arg Met Ile Asp Leu Ser Ser Ile Ser
625                 630                 635                 640
Thr Val Asp Ser Met Ile Ala Leu Asp Ile Asp Pro Leu Glu Asn Thr
                645                 650                 655
```

```
Asp Phe Arg Val Leu Glu Leu Tyr Ser Gln Lys Glu Leu Arg Ser Ser
            660                 665                 670

Asn Val Phe Asp Leu Glu Glu Ile Met Arg Glu Phe Asn Ser Tyr Lys
            675                 680                 685

Gln Arg Val Lys Tyr Val Glu Asp Lys Val Val Asp Pro Leu Pro Pro
            690                 695                 700

<210> SEQ ID NO 3
<211> LENGTH: 681
<212> TYPE: PRT
<213> ORGANISM: Artificial Sequence
<220> FEATURE:
<223> OTHER INFORMATION: Synthetic amino acid sequence

<400> SEQUENCE: 3

Ser Ser Ser Thr Ser His Ala Thr Ser Ser Ala His Asn Gly Ser His
1               5                   10                  15

Thr Ser Arg Thr Thr Ser Ala Gln Thr Arg Ser Val Ser Ser Gln His
            20                  25                  30

Val Thr Ser Ser Glu Ala Val Ser His Arg Ala Asn Glu Thr Ile Tyr
        35                  40                  45

Asn Thr Thr Leu Lys Tyr Gly Asp Val Val Gly Val Asn Thr Thr Lys
    50                  55                  60

Tyr Pro Tyr Arg Val Cys Ser Met Ala Gln Gly Thr Asp Leu Ile Arg
65                  70                  75                  80

Phe Glu Arg Asn Ile Val Cys Thr Pro Met Lys Pro Ile Asn Glu Asp
                85                  90                  95

Leu Asp Glu Gly Ile Met Val Val Tyr Lys Arg Asn Ile Val Ala His
            100                 105                 110

Thr Phe Lys Val Arg Val Tyr Gln Lys Val Leu Thr Phe Arg Arg Ser
            115                 120                 125

Tyr Ala Gly His Arg Thr Thr Tyr Leu Leu Gly Ser Asn Thr Glu Tyr
        130                 135                 140

Val Ala Pro Pro Met Trp Glu Ile His His Ile Asn Arg His Ser Gln
145                 150                 155                 160

Cys Tyr Ser Ser Tyr Ser Arg Val Ile Ala Gly Thr Val Phe Val Ala
                165                 170                 175

Tyr His Arg Asp Ser Tyr Glu Asn Lys Thr Met Gln Leu Met Leu Asp
            180                 185                 190

Asp Tyr Ser Asn Thr His Ser Thr Arg Tyr Val Thr Val Lys Asp Gln
        195                 200                 205

Trp His Ser Arg Gly Ser Thr Ala Leu Tyr Arg Glu Thr Cys Asn Leu
    210                 215                 220

Asn Cys Met Val Thr Ile Thr Thr Ala Arg Ser Lys Tyr Pro Tyr His
225                 230                 235                 240

Phe Phe Ala Thr Ser Thr Gly Asp Val Val Asp Ile Ser Pro Phe Tyr
                245                 250                 255

Asn Gly Thr Asn Arg Asn Thr Ser Tyr Phe Gly Glu Asn Ala Asp Lys
            260                 265                 270

Phe Phe Ile Phe Pro Asn Tyr Thr Ile Val Ser Asp Phe Gly Arg Ala
        275                 280                 285

Asn Ser Ala Pro Glu Thr His Arg Leu Val Ala Phe Leu Glu Arg Ala
    290                 295                 300

Asp Ser Val Ile Ser Trp Asp Ile Gln Asp Glu Lys Asn Val Thr Cys
305                 310                 315                 320
```

-continued

```
Gln Leu Thr Phe Trp Glu Ala Ser Glu Arg Thr Ile Arg Ser Glu Ala
            325                 330                 335

Glu Asp Ser Tyr His Phe Ser Ser Ala Lys Met Thr Ala Thr Phe Leu
            340                 345                 350

Ser Lys Lys Gln Glu Val Asn Met Ser Asp Pro Val Leu Asp Cys Val
            355                 360                 365

Arg Asp Gln Ala Leu Asn Lys Leu Gln Gln Ile Phe Asn Ala Ser Tyr
            370                 375                 380

Asn Gln Thr Tyr Glu Lys Tyr Gly Asn Val Ser Val Phe Glu Thr Thr
385                 390                 395                 400

Gly Gly Leu Val Val Phe Trp Gln Gly Ile Lys Gln Lys Ser Leu Leu
            405                 410                 415

Glu Leu Glu Arg Leu Ala Asn Ser Ser Gly Val Asn Ser Thr Arg Ala
            420                 425                 430

Thr Lys Ala Ser Thr Gly Asn Thr Thr Thr Leu Ser Leu Glu Ser Glu
            435                 440                 445

Ser Val Arg Asn Val Leu Tyr Ala Gln Leu Gln Phe Thr Tyr Asp Thr
            450                 455                 460

Leu Arg Ser Tyr Ile Asn Arg Ala Leu Ala Gln Ile Ala Glu Ala Trp
465                 470                 475                 480

Cys Val Asp Gln Arg Thr Leu Glu Val Phe Lys Glu Leu Ser Lys
            485                 490                 495

Ile Asn Pro Ser Ala Ile Leu Ser Ala Ile Tyr Asn Lys Pro Ile Ala
            500                 505                 510

Ala Arg Phe Met Gly Asp Val Leu Gly Leu Ala Ser Cys Val Thr Ile
            515                 520                 525

Asn Gln Thr Ser Val Lys Val Leu Arg Asp Met Asn Val Lys Glu Ser
            530                 535                 540

Pro Gly Arg Cys Tyr Ser Arg Pro Val Val Ile Phe Asn Phe Val Asn
545                 550                 555                 560

Ser Ser Tyr Val Gln Tyr Gly Gln Leu Gly Glu Asp Asn Glu Ile Leu
            565                 570                 575

Leu Gly Asn His Arg Thr Glu Glu Cys Gln Phe Pro Ser Leu Lys Ile
            580                 585                 590

Phe Ile Ala Gly Asn Ser Ala Tyr Glu Tyr Val Asp Tyr Leu Phe Lys
            595                 600                 605

Arg Met Ile Asp Leu Ser Ser Ile Ser Thr Val Asp Ser Met Ile Ala
            610                 615                 620

Leu Asp Ile Asp Pro Leu Glu Asn Thr Asp Phe Arg Val Leu Glu Leu
625                 630                 635                 640

Tyr Ser Gln Lys Glu Leu Arg Ser Ser Asn Val Phe Asp Leu Glu Glu
            645                 650                 655

Ile Met Arg Glu Phe Asn Ser Tyr Lys Gln Arg Val Lys Tyr Val Glu
            660                 665                 670

Asp Lys Val Val Asp Pro Leu Pro Pro
            675                 680
```

<210> SEQ ID NO 4
<211> LENGTH: 22
<212> TYPE: PRT
<213> ORGANISM: Artificial Sequence
<220> FEATURE:
<223> OTHER INFORMATION: Synthetic amino acid sequence

<400> SEQUENCE: 4

Met Glu Ser Arg Ile Trp Cys Leu Val Val Cys Val Asn Leu Cys Ile
1               5                   10                  15

Val Cys Leu Gly Ala Val
            20

<210> SEQ ID NO 5
<211> LENGTH: 686
<212> TYPE: PRT
<213> ORGANISM: Artificial Sequence
<220> FEATURE:
<223> OTHER INFORMATION: Synthetic amino acid sequence

<400> SEQUENCE: 5

Val Ser Ser Ser Thr Ser His Ala Thr Ser Ser Ala His Asn Gly
1               5                   10                  15

Ser His Thr Ser Arg Thr Thr Ser Ala Gln Thr Arg Ser Val Ser Ser
                20                  25                  30

Gln His Val Thr Ser Ser Glu Ala Val Ser His Arg Ala Asn Glu Thr
            35                  40                  45

Ile Tyr Asn Thr Thr Leu Lys Tyr Gly Asp Val Val Gly Val Asn Thr
        50                  55                  60

Thr Lys Tyr Pro Tyr Arg Val Cys Ser Met Ala Gln Gly Thr Asp Leu
65                  70                  75                  80

Ile Arg Phe Glu Arg Asn Ile Val Cys Thr Pro Met Lys Pro Ile Asn
                85                  90                  95

Glu Asp Leu Asp Glu Gly Ile Met Val Val Tyr Lys Arg Asn Ile Val
            100                 105                 110

Ala His Thr Phe Lys Val Arg Val Tyr Gln Lys Val Leu Thr Phe Arg
        115                 120                 125

Arg Ser Tyr Ala Gly His Arg Thr Thr Tyr Leu Leu Gly Ser Asn Thr
    130                 135                 140

Glu Tyr Val Ala Pro Pro Met Trp Glu Ile His His Ile Asn Arg His
145                 150                 155                 160

Ser Gln Cys Tyr Ser Ser Tyr Ser Arg Val Ile Ala Gly Thr Val Phe
                165                 170                 175

Val Ala Tyr His Arg Asp Ser Tyr Glu Asn Lys Thr Met Gln Leu Met
            180                 185                 190

Leu Asp Asp Tyr Ser Asn Thr His Ser Thr Arg Tyr Val Thr Val Lys
        195                 200                 205

Asp Gln Trp His Ser Arg Gly Ser Thr Ala Leu Tyr Arg Glu Thr Cys
    210                 215                 220

Asn Leu Asn Cys Met Val Thr Ile Thr Thr Ala Arg Ser Lys Tyr Pro
225                 230                 235                 240

Tyr His Phe Phe Ala Thr Ser Thr Gly Asp Val Val Asp Ile Ser Pro
                245                 250                 255

Phe Tyr Asn Gly Thr Asn Arg Asn Thr Ser Tyr Phe Gly Glu Asn Ala
            260                 265                 270

Asp Lys Phe Phe Ile Phe Pro Asn Tyr Thr Ile Val Ser Asp Phe Gly
        275                 280                 285

Arg Ala Asn Ser Ala Pro Glu Thr His Arg Leu Val Ala Phe Leu Glu
    290                 295                 300

Arg Ala Asp Ser Val Ile Ser Trp Asp Ile Gln Asp Glu Lys Asn Val
305                 310                 315                 320

Thr Cys Gln Leu Thr Phe Trp Glu Ala Ser Glu Arg Thr Ile Arg Ser
                325                 330                 335

```
Glu Ala Glu Asp Ser Tyr His Phe Ser Ser Ala Lys Met Thr Ala Thr
            340                 345                 350

Phe Leu Ser Lys Lys Gln Glu Val Asn Met Ser Asp Pro Val Leu Asp
            355                 360                 365

Cys Val Arg Asp Gln Ala Leu Asn Lys Leu Gln Ile Phe Asn Ala
            370                 375                 380

Ser Tyr Asn Gln Thr Tyr Glu Lys Tyr Gly Asn Val Ser Val Phe Glu
385                 390                 395                 400

Thr Thr Gly Gly Leu Val Val Phe Trp Gln Gly Ile Lys Gln Lys Ser
                405                 410                 415

Leu Leu Glu Leu Glu Arg Leu Ala Asn Ser Ser Gly Val Asn Ser Thr
            420                 425                 430

Arg Ala Thr Lys Ala Ser Thr Gly Asn Thr Thr Thr Leu Ser Leu Glu
            435                 440                 445

Ser Glu Ser Val Arg Asn Val Leu Tyr Ala Gln Leu Gln Phe Thr Tyr
            450                 455                 460

Asp Thr Leu Arg Ser Tyr Ile Asn Arg Ala Leu Ala Gln Ile Ala Glu
465                 470                 475                 480

Ala Trp Cys Val Asp Gln Arg Arg Thr Leu Glu Val Phe Lys Glu Leu
                485                 490                 495

Ser Lys Ile Asn Pro Ser Ala Ile Leu Ser Ala Ile Tyr Asn Lys Pro
            500                 505                 510

Ile Ala Ala Arg Phe Met Gly Asp Val Leu Gly Leu Ala Ser Cys Val
            515                 520                 525

Thr Ile Asn Gln Thr Ser Val Lys Val Leu Arg Asp Met Asn Val Lys
            530                 535                 540

Glu Ser Pro Gly Arg Cys Tyr Ser Arg Pro Val Val Ile Phe Asn Phe
545                 550                 555                 560

Val Asn Ser Ser Tyr Val Gln Tyr Gly Gln Leu Gly Glu Asp Asn Glu
                565                 570                 575

Ile Leu Leu Gly Asn His Arg Thr Glu Glu Cys Gln Phe Pro Ser Leu
            580                 585                 590

Lys Ile Phe Ile Ala Gly Asn Ser Ala Tyr Glu Tyr Val Asp Tyr Leu
            595                 600                 605

Phe Lys Arg Met Ile Asp Leu Ser Ser Ile Ser Thr Val Asp Ser Met
            610                 615                 620

Ile Ala Leu Asp Ile Asp Pro Leu Glu Asn Thr Asp Phe Arg Val Leu
625                 630                 635                 640

Glu Leu Tyr Ser Gln Lys Glu Leu Arg Ser Ser Asn Val Phe Asp Leu
                645                 650                 655

Glu Glu Ile Met Arg Glu Phe Asn Ser Tyr Lys Gln Arg Val Lys Tyr
            660                 665                 670

Val Glu Asp Lys Val Val Asp Pro Leu Pro Pro Gly Ser Gly
            675                 680                 685

<210> SEQ ID NO 6
<211> LENGTH: 905
<212> TYPE: PRT
<213> ORGANISM: Human cytomegalovirus

<400> SEQUENCE: 6

Met Glu Ser Arg Ile Trp Cys Leu Val Val Cys Val Asn Leu Cys Ile
1               5                   10                  15

Val Cys Leu Gly Ala Val Val Ser Ser Ser Ser Thr Ser His Ala Thr
```

-continued

```
                20                  25                  30
    Ser Ser Ala His Asn Gly Ser His Thr Ser Arg Thr Thr Ser Ala Gln
                35                  40                  45

Thr Arg Ser Val Ser Ser Gln His Val Thr Ser Ser Glu Ala Val Ser
                50                  55                  60

His Arg Ala Asn Glu Thr Ile Tyr Asn Thr Thr Leu Lys Tyr Gly Asp
    65                  70                  75                  80

Val Val Gly Val Asn Thr Thr Lys Tyr Pro Tyr Arg Val Cys Ser Met
                    85                  90                  95

Ala Gln Gly Thr Asp Leu Ile Arg Phe Glu Arg Asn Ile Val Cys Thr
                   100                 105                 110

Pro Met Lys Pro Ile Asn Glu Asp Leu Asp Glu Gly Ile Met Val Val
                   115                 120                 125

Tyr Lys Arg Asn Ile Val Ala His Thr Phe Lys Val Arg Val Tyr Gln
                   130                 135                 140

Lys Val Leu Thr Phe Arg Arg Ser Tyr Ala Tyr Ile His Thr Thr Tyr
    145                 150                 155                 160

Leu Leu Gly Ser Asn Thr Glu Tyr Val Ala Pro Pro Met Trp Glu Ile
                   165                 170                 175

His His Ile Asn Arg His Ser Gln Cys Tyr Ser Ser Tyr Ser Arg Val
                   180                 185                 190

Ile Ala Gly Thr Val Phe Val Ala Tyr His Arg Asp Ser Tyr Glu Asn
                   195                 200                 205

Lys Thr Met Gln Leu Met Leu Asp Asp Tyr Ser Asn Thr His Ser Thr
                   210                 215                 220

Arg Tyr Val Thr Val Lys Asp Gln Trp His Ser Arg Gly Ser Thr Trp
    225                 230                 235                 240

Leu Tyr Arg Glu Thr Cys Asn Leu Asn Cys Met Val Thr Ile Thr Thr
                   245                 250                 255

Ala Arg Ser Lys Tyr Pro Tyr His Phe Phe Ala Thr Ser Thr Gly Asp
                   260                 265                 270

Val Val Asp Ile Ser Pro Phe Tyr Asn Gly Thr Asn Arg Asn Thr Ser
                   275                 280                 285

Tyr Phe Gly Glu Asn Ala Asp Lys Phe Phe Ile Phe Pro Asn Tyr Thr
                   290                 295                 300

Ile Val Ser Asp Phe Gly Arg Ala Asn Ser Ala Pro Glu Thr His Arg
    305                 310                 315                 320

Leu Val Ala Phe Leu Glu Arg Ala Asp Ser Val Ile Ser Trp Asp Ile
                   325                 330                 335

Gln Asp Glu Lys Asn Val Thr Cys Gln Leu Thr Phe Trp Glu Ala Ser
                   340                 345                 350

Glu Arg Thr Ile Arg Ser Glu Ala Glu Asp Ser Tyr His Phe Ser Ser
                   355                 360                 365

Ala Lys Met Thr Ala Thr Phe Leu Ser Lys Lys Gln Glu Val Asn Met
                   370                 375                 380

Ser Asp Pro Val Leu Asp Cys Val Arg Asp Gln Ala Leu Asn Lys Leu
    385                 390                 395                 400

Gln Gln Ile Phe Asn Ala Ser Tyr Asn Gln Thr Tyr Glu Lys Tyr Gly
                   405                 410                 415

Asn Val Ser Val Phe Glu Thr Thr Gly Gly Leu Val Val Phe Trp Gln
                   420                 425                 430

Gly Ile Lys Gln Lys Ser Leu Leu Glu Leu Glu Arg Leu Ala Asn Ser
                   435                 440                 445
```

```
Ser Gly Val Asn Ser Thr Arg Arg Thr Lys Arg Ser Thr Gly Asn Thr
    450                 455                 460

Thr Thr Leu Ser Leu Glu Ser Glu Ser Val Arg Asn Val Leu Tyr Ala
465                 470                 475                 480

Gln Leu Gln Phe Thr Tyr Asp Thr Leu Arg Ser Tyr Ile Asn Arg Ala
                485                 490                 495

Leu Ala Gln Ile Ala Glu Ala Trp Cys Val Asp Gln Arg Arg Thr Leu
                500                 505                 510

Glu Val Phe Lys Glu Leu Ser Lys Ile Asn Pro Ser Ala Ile Leu Ser
                515                 520                 525

Ala Ile Tyr Asn Lys Pro Ile Ala Ala Arg Phe Met Gly Asp Val Leu
530                 535                 540

Gly Leu Ala Ser Cys Val Thr Ile Asn Gln Thr Ser Val Lys Val Leu
545                 550                 555                 560

Arg Asp Met Asn Val Lys Glu Ser Pro Gly Arg Cys Tyr Ser Arg Pro
                565                 570                 575

Val Val Ile Phe Asn Phe Val Asn Ser Ser Tyr Val Gln Tyr Gly Gln
                580                 585                 590

Leu Gly Glu Asp Asn Glu Ile Leu Leu Gly Asn His Arg Thr Glu Glu
                595                 600                 605

Cys Gln Phe Pro Ser Leu Lys Ile Phe Ile Ala Gly Asn Ser Ala Tyr
610                 615                 620

Glu Tyr Val Asp Tyr Leu Phe Lys Arg Met Ile Asp Leu Ser Ser Ile
625                 630                 635                 640

Ser Thr Val Asp Ser Met Ile Ala Leu Asp Ile Asp Pro Leu Glu Asn
                645                 650                 655

Thr Asp Phe Arg Val Leu Glu Leu Tyr Ser Gln Lys Glu Leu Arg Ser
                660                 665                 670

Ser Asn Val Phe Asp Leu Glu Glu Ile Met Arg Glu Phe Asn Ser Tyr
                675                 680                 685

Lys Gln Arg Val Lys Tyr Val Glu Asp Lys Val Val Asp Pro Leu Pro
    690                 695                 700

Pro Tyr Leu Lys Gly Leu Asp Asp Leu Met Ser Gly Leu Gly Ala Ala
705                 710                 715                 720

Gly Lys Ala Val Gly Val Ala Ile Gly Ala Val Gly Gly Ala Val Ala
                725                 730                 735

Ser Val Val Glu Gly Val Ala Thr Phe Leu Lys Asn Pro Phe Gly Ala
                740                 745                 750

Phe Thr Ile Ile Leu Val Ala Ile Ala Val Ile Ile Tyr Leu
755                 760                 765

Ile Tyr Thr Arg Gln Arg Arg Leu Cys Met Gln Pro Leu Gln Asn Leu
    770                 775                 780

Phe Pro Tyr Leu Val Ser Ala Asp Gly Thr Thr Val Thr Ser Gly Asn
785                 790                 795                 800

Thr Lys Asp Thr Ser Leu Gln Ala Pro Pro Ser Tyr Glu Glu Ser Val
                805                 810                 815

Tyr Asn Ser Gly Arg Lys Gly Pro Gly Pro Pro Ser Ser Asp Ala Ser
                820                 825                 830

Thr Ala Ala Pro Pro Tyr Thr Asn Glu Gln Ala Tyr Gln Met Leu Leu
                835                 840                 845

Ala Leu Ala Arg Leu Asp Ala Glu Gln Arg Ala Gln Gln Asn Gly Thr
850                 855                 860
```

```
Asp Ser Leu Asp Gly Gln Thr Gly Thr Gln Asp Lys Gly Gln Lys Pro
865                 870                 875                 880

Asn Leu Leu Asp Arg Leu Arg His Arg Lys Asn Gly Tyr Arg His Leu
                885                 890                 895

Lys Asp Ser Asp Glu Glu Glu Asn Val
                900                 905

<210> SEQ ID NO 7
<211> LENGTH: 683
<212> TYPE: PRT
<213> ORGANISM: Artificial Sequence
<220> FEATURE:
<223> OTHER INFORMATION: Synthetic amino acid sequence

<400> SEQUENCE: 7

Met Ser Lys Asn Trp Phe Pro Leu Leu Cys Ala Ser Val Leu Val Val
1               5                   10                  15

Tyr Val Ala Ile Ala Ser Ser Thr Gly Thr Ala Ser Ala Val Thr
                20                  25                  30

Pro Ala Pro Thr Glu Asn Thr Thr Gly Glu Ile Ile Ala Asn Thr Thr
                35                  40                  45

Leu Arg Thr His Glu Val Phe Arg Val Asn Met Ser Lys Phe Pro Tyr
50                  55                  60

Arg Val Cys Ser Met Ala Gln Gly Thr Asp Leu Leu Arg Phe Glu Gln
65                  70                  75                  80

Asn Ile Arg Cys Asp Ser Phe Lys Pro Thr Lys Glu Asp Phe Asp Glu
                85                  90                  95

Gly Ile Met Val Val Tyr Lys Arg Asp Ile Lys Pro Tyr Thr Phe Lys
                100                 105                 110

Val His Ile Tyr Gln Lys Ile Leu Thr Phe Arg Gln Ser Tyr Ser Gly
                115                 120                 125

His Arg Glu Asn His Leu Leu Gly Phe Ser Gln Glu Arg Leu Ala Val
                130                 135                 140

Pro Met Trp Glu Val Asn Tyr Ile Asn Arg Leu Asn Arg Cys Tyr Asn
145                 150                 155                 160

Ser Val Val Arg Asn Val Ala Gly Val Thr Tyr Val Asn Tyr His Lys
                165                 170                 175

Asp Ser Tyr Val Asn Glu Thr Met His Leu Ile Glu Asp Asp Tyr Ser
                180                 185                 190

Asn Thr His Ser Ala Arg Tyr Val Thr Val Lys Glu Leu Trp His Lys
                195                 200                 205

Pro Gly Ser Thr Ala Leu Tyr Thr Thr Ser Cys Asn Val Asn Cys Met
                210                 215                 220

Val Thr Val Thr Thr Ala Arg Ser Lys Tyr Pro Tyr Asp Phe Phe Val
225                 230                 235                 240

Thr Ser Gly Gly Glu Val Val Asp Ile Ser Pro Phe Tyr Asn Gly Ser
                245                 250                 255

Asn Asn Glu His Phe Gly Glu Asn Arg Asp Lys Phe Tyr Ile Arg Arg
                260                 265                 270

Asn Tyr Ser Met Val Glu Ser Tyr Gly Arg Asp Asn Ala Pro Leu Val
                275                 280                 285

Ala His Glu Leu Val Ala Phe Phe Glu Arg Pro Asp Met Leu Met Ser
                290                 295                 300

Trp Asp Ile Val Asp Glu Ala Asn Asn Thr Cys Glu Tyr Thr Phe Trp
305                 310                 315                 320
```

```
Glu Gln Ser Glu Arg Thr Ile Arg Ser Glu Ala Asp Glu Thr Tyr His
            325                 330                 335

Phe Thr Ser His Ser Met Thr Ala Thr Phe Leu Thr Leu Lys Lys Glu
        340                 345                 350

Leu Asn Glu Ser Asp Ser Asp Phe Asp Cys Ile Arg Asp Glu Ala Asn
    355                 360                 365

Glu Arg Leu Glu Lys Ile Phe Asn Thr Thr Tyr Asn Glu Thr Tyr Val
370                 375                 380

Lys Ser Gly Asn Val Ser Val Tyr Glu Thr Ser Gly Gly Leu Ile Val
385                 390                 395                 400

Phe Trp Leu Pro Val Lys Glu Lys Ala Ile Trp Glu Met Gln Lys Leu
                405                 410                 415

Ala Thr Glu His Ala Asn Asn Thr Asn Ala Thr Arg Ala Thr Lys Ala
            420                 425                 430

Ser Thr Asn Ser Gly Asn Ser Thr Lys Glu Val Leu Gln Asn Val Val
        435                 440                 445

Tyr Ala Gln Leu Gln Phe Thr Tyr Asp Thr Leu Arg Asn Tyr Ile Asn
450                 455                 460

Arg Ala Leu Arg Gln Ile Ala Glu Ala Trp Cys Lys Asp Gln Lys Arg
465                 470                 475                 480

Thr Leu Glu Val Leu Lys Glu Leu Ser Lys Ile Asn Pro Ser Ala Met
                485                 490                 495

Leu Ser Ala Ile Tyr Asp Lys Pro Ile Ala Ala Arg Phe Val Gly Asp
            500                 505                 510

Val Ile Ser Leu Ala Arg Cys Val Glu Val Asp Gln Asn Ser Val Gln
        515                 520                 525

Val Leu Arg Asp Met His Thr Lys Glu Lys Gly Leu Cys Tyr Ser Arg
530                 535                 540

Pro Val Val Leu Tyr Thr Phe Val Asn Ser Ser His Val Gln Tyr Gly
545                 550                 555                 560

Gln Leu Gly Glu Asp Asn Glu Ile Leu Leu Gly Arg His Arg Thr Glu
                565                 570                 575

Ala Cys Glu Ser Pro Ser Leu Lys Ile Phe Ile Ala Gly Asn Ser Ser
            580                 585                 590

Tyr Glu Tyr Val Asp Tyr Leu Tyr Lys Arg Met Ile Pro Leu Asp Ser
        595                 600                 605

Ile Ser Thr Val Asp Thr Met Ile Ser Leu Asp Ile Asp Pro Leu Glu
610                 615                 620

Asn Thr Asp Phe Arg Ala Leu Glu Leu Tyr Ser Arg Asp Glu Leu Arg
625                 630                 635                 640

Ser Ser Asn Val Phe Asp Leu Glu Asp Ile Met Arg Glu Phe Asn Thr
                645                 650                 655

Tyr Lys Gln Arg Met Val His Val Glu Gly Lys Val Phe Asp Asn Val
            660                 665                 670

Pro Ala Gly Ser Gly His His His His His
        675                 680

<210> SEQ ID NO 8
<211> LENGTH: 682
<212> TYPE: PRT
<213> ORGANISM: Artificial Sequence
<220> FEATURE:
<223> OTHER INFORMATION: Synthetic amino acid sequence

<400> SEQUENCE: 8
```

```
Ser Lys Asn Trp Phe Pro Leu Leu Cys Ala Ser Val Leu Val Val Tyr
1               5                   10                  15

Val Ala Ile Ala Ser Ser Thr Gly Thr Ala Ser Ala Val Thr Pro
            20                  25                  30

Ala Pro Thr Glu Asn Thr Thr Gly Glu Ile Ile Ala Asn Thr Thr Leu
                35                  40                  45

Arg Thr His Glu Val Phe Arg Val Asn Met Ser Lys Phe Pro Tyr Arg
            50                  55                  60

Val Cys Ser Met Ala Gln Gly Thr Asp Leu Leu Arg Phe Glu Gln Asn
65                  70                  75                  80

Ile Arg Cys Asp Ser Phe Lys Pro Thr Lys Glu Asp Phe Asp Glu Gly
                85                  90                  95

Ile Met Val Val Tyr Lys Arg Asp Ile Lys Pro Tyr Thr Phe Lys Val
                100                 105                 110

His Ile Tyr Gln Lys Ile Leu Thr Phe Arg Gln Ser Tyr Ser Gly His
                115                 120                 125

Arg Glu Asn His Leu Leu Gly Phe Ser Gln Glu Arg Leu Ala Val Pro
            130                 135                 140

Met Trp Glu Val Asn Tyr Ile Asn Arg Leu Asn Arg Cys Tyr Asn Ser
145                 150                 155                 160

Val Val Arg Asn Val Ala Gly Val Thr Tyr Val Asn Tyr His Lys Asp
                165                 170                 175

Ser Tyr Val Asn Glu Thr Met His Leu Ile Glu Asp Tyr Ser Asn
            180                 185                 190

Thr His Ser Ala Arg Tyr Val Thr Val Lys Glu Leu Trp His Lys Pro
            195                 200                 205

Gly Ser Thr Ala Leu Tyr Thr Thr Ser Cys Asn Val Asn Cys Met Val
    210                 215                 220

Thr Val Thr Thr Ala Arg Ser Lys Tyr Pro Tyr Asp Phe Phe Val Thr
225                 230                 235                 240

Ser Gly Gly Glu Val Val Asp Ile Ser Pro Phe Tyr Asn Gly Ser Asn
                245                 250                 255

Asn Glu His Phe Gly Glu Asn Arg Asp Lys Phe Tyr Ile Arg Arg Asn
            260                 265                 270

Tyr Ser Met Val Glu Ser Tyr Gly Arg Asp Asn Ala Pro Leu Val Ala
            275                 280                 285

His Glu Leu Val Ala Phe Phe Glu Arg Pro Asp Met Leu Met Ser Trp
    290                 295                 300

Asp Ile Val Asp Glu Ala Asn Asn Thr Cys Glu Tyr Thr Phe Trp Glu
305                 310                 315                 320

Gln Ser Glu Arg Thr Ile Arg Ser Glu Ala Asp Glu Thr Tyr His Phe
            325                 330                 335

Thr Ser His Ser Met Thr Ala Thr Phe Leu Thr Leu Lys Lys Glu Leu
            340                 345                 350

Asn Glu Ser Asp Ser Asp Phe Asp Cys Ile Arg Asp Glu Ala Asn Glu
            355                 360                 365

Arg Leu Glu Lys Ile Phe Asn Thr Thr Tyr Asn Glu Thr Tyr Val Lys
    370                 375                 380

Ser Gly Asn Val Ser Val Tyr Glu Thr Ser Gly Gly Leu Ile Val Phe
385                 390                 395                 400

Trp Leu Pro Val Lys Glu Lys Ala Ile Trp Glu Met Gln Lys Leu Ala
                405                 410                 415

Thr Glu His Ala Asn Asn Thr Asn Ala Thr Arg Ala Thr Lys Ala Ser
```

```
                420             425             430
Thr Asn Ser Gly Asn Ser Thr Lys Glu Val Leu Gln Asn Val Val Tyr
            435             440             445

Ala Gln Leu Gln Phe Thr Tyr Asp Thr Leu Arg Asn Tyr Ile Asn Arg
450             455             460

Ala Leu Arg Gln Ile Ala Glu Ala Trp Cys Lys Asp Gln Lys Arg Thr
465             470             475             480

Leu Glu Val Leu Lys Glu Leu Ser Lys Ile Asn Pro Ser Ala Met Leu
            485             490             495

Ser Ala Ile Tyr Asp Lys Pro Ile Ala Ala Arg Phe Val Gly Asp Val
            500             505             510

Ile Ser Leu Ala Arg Cys Val Glu Val Asp Gln Asn Ser Val Gln Val
            515             520             525

Leu Arg Asp Met His Thr Lys Glu Lys Gly Leu Cys Tyr Ser Arg Pro
530             535             540

Val Val Leu Tyr Thr Phe Val Asn Ser Ser His Val Gln Tyr Gly Gln
545             550             555             560

Leu Gly Glu Asp Asn Glu Ile Leu Leu Gly Arg His Arg Thr Glu Ala
            565             570             575

Cys Glu Ser Pro Ser Leu Lys Ile Phe Ile Ala Gly Asn Ser Ser Tyr
            580             585             590

Glu Tyr Val Asp Tyr Leu Tyr Lys Arg Met Ile Pro Leu Asp Ser Ile
            595             600             605

Ser Thr Val Asp Thr Met Ile Ser Leu Asp Ile Asp Pro Leu Glu Asn
610             615             620

Thr Asp Phe Arg Ala Leu Glu Leu Tyr Ser Arg Asp Glu Leu Arg Ser
625             630             635             640

Ser Asn Val Phe Asp Leu Glu Asp Ile Met Arg Glu Phe Asn Thr Tyr
            645             650             655

Lys Gln Arg Met Val His Val Glu Gly Lys Val Phe Asp Asn Val Pro
            660             665             670

Ala Gly Ser Gly His His His His His His
        675             680

<210> SEQ ID NO 9
<211> LENGTH: 7
<212> TYPE: PRT
<213> ORGANISM: Artificial Sequence
<220> FEATURE:
<223> OTHER INFORMATION: Synthetic amino acid sequence

<400> SEQUENCE: 9

Val Val Asp Pro Leu Pro Pro
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic amino acid sequence

<400> SEQUENCE: 10

Arg Ala Thr Lys Ala Ser
1               5

<210> SEQ ID NO 11
<211> LENGTH: 849
```

<212> TYPE: PRT
<213> ORGANISM: Rhesus cytomegalovirus

<400> SEQUENCE: 11

```
Met Ser Lys Asn Trp Phe Pro Leu Leu Cys Ala Ser Val Leu Val
1               5                   10                  15

Tyr Val Ala Ile Ala Ser Ser Thr Gly Thr Ala Ser Ala Val Thr
                20                  25                  30

Pro Ala Pro Thr Glu Asn Thr Thr Gly Glu Ile Ile Ala Asn Thr Thr
            35                  40                  45

Leu Arg Thr His Glu Val Phe Arg Val Asn Met Ser Lys Phe Pro Tyr
        50                  55                  60

Arg Val Cys Ser Met Ala Gln Gly Thr Asp Leu Leu Arg Phe Glu Gln
65                  70                  75                  80

Asn Ile Arg Cys Asp Ser Phe Lys Pro Thr Lys Glu Asp Phe Asp Glu
                85                  90                  95

Gly Ile Met Val Val Tyr Lys Arg Asp Ile Lys Pro Tyr Thr Phe Lys
                100                 105                 110

Val His Ile Tyr Gln Lys Ile Leu Thr Phe Arg Gln Ser Tyr Ser Phe
            115                 120                 125

Ile Arg Glu Asn His Leu Leu Gly Phe Ser Gln Glu Arg Leu Ala Val
130                 135                 140

Pro Met Trp Glu Val Asn Tyr Ile Asn Arg Leu Asn Arg Cys Tyr Asn
145                 150                 155                 160

Ser Val Val Arg Asn Val Ala Gly Val Thr Tyr Val Asn Tyr His Lys
                165                 170                 175

Asp Ser Tyr Val Asn Glu Thr Met His Leu Ile Glu Asp Asp Tyr Ser
            180                 185                 190

Asn Thr His Ser Ala Arg Tyr Val Thr Val Lys Glu Leu Trp His Lys
            195                 200                 205

Pro Gly Ser Thr Trp Leu Tyr Thr Thr Ser Cys Asn Val Asn Cys Met
210                 215                 220

Val Thr Val Thr Thr Ala Arg Ser Lys Tyr Pro Tyr Asp Phe Phe Val
225                 230                 235                 240

Thr Ser Gly Gly Glu Val Val Asp Ile Ser Pro Phe Tyr Asn Gly Ser
                245                 250                 255

Asn Asn Glu His Phe Gly Glu Asn Arg Asp Lys Phe Tyr Ile Arg Arg
            260                 265                 270

Asn Tyr Ser Met Val Glu Ser Tyr Gly Arg Asp Asn Ala Pro Leu Val
            275                 280                 285

Ala His Glu Leu Val Ala Phe Phe Glu Arg Pro Asp Met Leu Met Ser
290                 295                 300

Trp Asp Ile Val Asp Glu Ala Asn Asn Thr Cys Glu Tyr Thr Phe Trp
305                 310                 315                 320

Glu Gln Ser Glu Arg Thr Ile Arg Ser Glu Ala Asp Glu Thr Tyr His
                325                 330                 335

Phe Thr Ser His Ser Met Thr Ala Thr Phe Leu Thr Leu Lys Lys Glu
            340                 345                 350

Leu Asn Glu Ser Asp Ser Asp Phe Asp Cys Ile Arg Asp Glu Ala Asn
        355                 360                 365

Glu Arg Leu Glu Lys Ile Phe Asn Thr Thr Tyr Asn Glu Thr Tyr Val
370                 375                 380

Lys Ser Gly Asn Val Ser Val Tyr Glu Thr Ser Gly Gly Leu Ile Val
385                 390                 395                 400
```

-continued

```
Phe Trp Leu Pro Val Lys Glu Lys Ala Ile Trp Glu Met Gln Lys Leu
                405                 410                 415

Ala Thr Glu His Ala Asn Asn Thr Asn Ala Thr Arg Arg Arg Lys Arg
            420                 425                 430

Ser Thr Asn Ser Gly Asn Ser Thr Lys Glu Val Leu Gln Asn Val Val
            435                 440                 445

Tyr Ala Gln Leu Gln Phe Thr Tyr Asp Thr Leu Arg Asn Tyr Ile Asn
450                 455                 460

Arg Ala Leu Arg Gln Ile Ala Glu Ala Trp Cys Lys Asp Gln Lys Arg
465                 470                 475                 480

Thr Leu Glu Val Leu Lys Glu Leu Ser Lys Ile Asn Pro Ser Ala Met
                485                 490                 495

Leu Ser Ala Ile Tyr Asp Lys Pro Ile Ala Ala Arg Phe Val Gly Asp
                500                 505                 510

Val Ile Ser Leu Ala Arg Cys Val Glu Val Asp Gln Asn Ser Val Gln
            515                 520                 525

Val Leu Arg Asp Met His Thr Lys Glu Lys Gly Leu Cys Tyr Ser Arg
            530                 535                 540

Pro Val Val Leu Tyr Thr Phe Val Asn Ser Ser His Val Gln Tyr Gly
545                 550                 555                 560

Gln Leu Gly Glu Asp Asn Glu Ile Leu Leu Gly Arg His Arg Thr Glu
                565                 570                 575

Ala Cys Glu Ser Pro Ser Leu Lys Ile Phe Ile Ala Gly Asn Ser Ser
                580                 585                 590

Tyr Glu Tyr Val Asp Tyr Leu Tyr Lys Arg Met Ile Pro Leu Asp Ser
            595                 600                 605

Ile Ser Thr Val Asp Thr Met Ile Ser Leu Asp Ile Asp Pro Leu Glu
            610                 615                 620

Asn Thr Asp Phe Arg Ala Leu Glu Leu Tyr Ser Arg Asp Glu Leu Arg
625                 630                 635                 640

Ser Ser Asn Val Phe Asp Leu Glu Asp Ile Met Arg Glu Phe Asn Thr
                645                 650                 655

Tyr Lys Gln Arg Met Val His Val Glu Gly Lys Val Phe Asp Asn Val
                660                 665                 670

Pro Ala Tyr Leu Arg Gly Leu Asp Asp Met Met Ser Gly Leu Gly Ser
            675                 680                 685

Ala Gly Lys Ala Leu Gly Val Ala Ile Gly Ala Val Gly Gly Ala Val
            690                 695                 700

Ala Ser Phe Val Glu Gly Val Val Gly Phe Ile Glu Asn Pro Phe Gly
705                 710                 715                 720

Ser Phe Thr Val Ile Leu Phe Leu Leu Ala Val Leu Gly Val Ile Tyr
                725                 730                 735

Leu Ile Tyr Met Arg Gln Lys Arg Ala Tyr Glu Lys Pro Phe Glu His
                740                 745                 750

Phe Phe Pro Tyr Val Val Pro Pro Thr Thr Val Lys Glu Ala Pro Pro
            755                 760                 765

Ser Tyr Glu Gln Ser Gln Tyr Glu Asn Ile Lys Glu Lys Ala Ala Ser
770                 775                 780

Ala Thr Lys Glu Phe Ser Leu Glu Glu Ala Tyr Gln Met Leu Leu Ala
785                 790                 795                 800

Leu Gln Lys Leu Asp Gln Glu Lys Arg Arg Lys Ala Glu Ala Asp Asp
                805                 810                 815
```

```
Glu Asp Phe Ala Ser Asn Gly Gln Ser Ala Gly Phe Leu Asp Arg Leu
            820                 825                 830

Arg Asn Arg Arg Gly Gly Tyr Gln Lys Ile Gln Asn Glu Tyr Glu
        835                 840                 845

Val

<210> SEQ ID NO 12
<211> LENGTH: 6
<212> TYPE: PRT
<213> ORGANISM: Artificial Sequence
<220> FEATURE:
<223> OTHER INFORMATION: Synthetic amino acid sequence

<400> SEQUENCE: 12

Tyr Ala Tyr Ile His Thr
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic amino acid sequence

<400> SEQUENCE: 13

Gly Ser Thr Trp Leu Tyr Arg Glu
1               5

<210> SEQ ID NO 14
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 14

Arg Thr Lys Arg
1

<210> SEQ ID NO 15
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 15

Arg Thr Lys Arg
1
```